US008456629B2

(12) United States Patent
Jalali et al.

(10) Patent No.: US 8,456,629 B2
(45) Date of Patent: Jun. 4, 2013

(54) APPARATUS AND METHOD FOR MULTIPLE-PULSE IMPULSIVE STIMULATED RAMAN SPECTROSCOPY

(75) Inventors: Bahram Jalali, Los Angeles, CA (US); Keisuke Goda, Los Angeles, CA (US); Akira Sato, Tokyo (JP); Kenji Taira, Tokyo (JP)

(73) Assignees: The Regents of the University of California, Oakland, CA (US); Olympus Corporation, Tokyo (JP)

( * ) Notice: Subject to any disclaimer, the term of this patent is extended or adjusted under 35 U.S.C. 154(b) by 390 days.

(21) Appl. No.: 12/945,030

(22) Filed: Nov. 12, 2010

(65) Prior Publication Data

US 2011/0122407 A1    May 26, 2011

Related U.S. Application Data

(60) Provisional application No. 61/262,220, filed on Nov. 18, 2009.

(51) Int. Cl.
*G01J 3/44* (2006.01)

(52) U.S. Cl.
USPC ........................................................ 356/301

(58) Field of Classification Search
USPC ........................................................ 356/301
See application file for complete search history.

(56) References Cited

U.S. PATENT DOCUMENTS

| | | | | |
|---|---|---|---|---|
| 4,512,660 A * | 4/1985 | Goldberg | ........................ | 356/301 |
| 2004/0042006 A1 * | 3/2004 | Chen et al. | ..................... | 356/301 |
| 2005/0228594 A1 | 10/2005 | Pryce-Lewis et al. | | |
| 2006/0066848 A1 * | 3/2006 | Frankel | ........................ | 356/301 |
| 2006/0192969 A1 | 8/2006 | Marks | | |
| 2008/0170218 A1 | 7/2008 | Dantus et al. | | |
| 2009/0212769 A1 | 8/2009 | Stoica et al. | | |
| 2010/0046039 A1 * | 2/2010 | Xie et al. | ...................... | 356/301 |

OTHER PUBLICATIONS

Fayer, M.D.—"Fast Protein Dynamics Probed with Infrared Vibrational Echo Experiments"—Annu. Rev. Phys. Chem, 2001, vol. 52, pp. 315-356.
Weiner, A.M et al.—"Femtosecond multiple-pulse impulsive stimulated Raman scattering spectroscopy" J. Opt. Soc. Am. B, vol. 8, No. 6, Jun. 1991, pp. 1264-1275.
USPTO, ISA/US, International Search Report and Written Opinion issued on Mar. 1, 2011 for PCT International patent application No. PCT/US10/56475, filed on Nov. 12, 2010, counterpart to U.S. Appl. No. 12/945,030, pp. 1-9.
Weinacht, T.C. et al.—"Using feedback for coherent control of quantum systems"—Jour. Optics B: Quantum Semiclass. Opt. 4, 2002, pp. R35-R52.

(Continued)

*Primary Examiner* — Kara E Geisel
(74) *Attorney, Agent, or Firm* — John P. O'Banion

(57) ABSTRACT

Spectroscopic measurements are described based on light-molecule interaction in response to a resonant rate optical pulse train so that a Raman spectrum is reflected containing at least two types of vibrational mode information (e.g., vibrational frequency, and vibrational phase relaxation) on the molecules comprising the object. A pump optical pulse train generation means is configured for generating an optical pulse train having an arbitrary repetition rate which is directed through irradiation means to the sample object. Light from the sample object is collected and vibrational coherence is detected for the sample object. The sample is tested across a plurality of different repetition frequencies. The detected information can be compared with data from other known samples from within a database when analyzing the information collected.

20 Claims, 31 Drawing Sheets

OTHER PUBLICATIONS

Weiner, A.M. et al.—Femtosecond multiple-pulse impulsive stimulated Raman scattering spectroscopy—Jour. Optics Soc. Am. B, vol. 8, No. 6, Jun. 1991, pp. 1264-1275.

Efimov, A.—"Adaptive Control of Lasers and Their Interactions with Matter Using Femtosecond Pulse Shaping" Dissertation (online), Dec. 2000, p. 31, fig. 5.11, retrieved online on Feb. 9, 2011 from http://citeseerx.ist.psu.edu/viewdoc/download?doi=10.1.1.8.5343&rep=rep1&type=pdf.

Weiner, A.M.—"Programmable Femtosecond Pulse Shaping"—Presentation (online) May 2001, p. 35, retrieved online on Feb. 9, 2011 from http://cobweb.ecn.purdue.edu/~fsoptics/presentations/CLEO_5-01_final.pdf.

* cited by examiner

APPARATUS AND METHOD FOR MULTIPLE-PULSE IMPULSIVE STIMULATED RAMAN SPECTROSCOPY

CROSS-REFERENCE TO RELATED APPLICATIONS

This application claims priority from U.S. provisional patent application Ser. No. 61/262,220 filed on Nov. 18, 2009, which is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

The present invention pertains generally to spectroscopic measurement apparatus, and more particularly to spectroscopic measurements based on light-molecule interaction in response to a resonant rate optical pulse train.

2. Description of Related Art

Performing biological analysis typically requires invasive procedures, such as in discriminating between healthy tissue and cancerous tissue. It is, therefore, an object of some investigation to provide an ability to study a biological samples acquired in a non-pharmaceutical and low-invasive, such as in response to vibrational spectrum data derived from a molecule. A vibrational spectrum in the fingerprint region has been used in analysis of a biological sample, while using a vibrational spectrum in a far infrared region lower than or equal to several terahertz in analysis of a biological sample is more recently under study. A terahertz vibrational spectrum derived from a biological macromolecule, which reflects a vibrational form in which a large number of atoms undergo collective displacement (collective mode) and a hydration structure, can be sensitive to global motion specific to a molecular structure and structural change in function expression. A terahertz vibrational spectrum is therefore expected to provide information complementary to vibrational spectroscopic information in the fingerprint region in analysis of a biological sample.

Terahertz absorption spectroscopy and spontaneous Raman scattering spectroscopy have been known as technologies for observing a terahertz vibrational spectrum derived from a biological sample. Since terahertz absorption spectroscopy involves irradiating a biological sample with far infrared light and measuring an absorption spectrum, the fact that water and biological macromolecules absorb and attenuate the diagnostic light impedes the spectrum measurement. In Raman scattering, narrow-band near infrared or visible light is typically used to excite a biological sample and non-elastically scattered light from the sample is measured. When a spectrum in a low-energy region lower than or equal to several terahertz is observed in the spontaneous Raman scattering spectroscopy, background light including elastically scattered light impedes the measurement.

Another terahertz vibrational spectrum observation approach other than the methods described above is coherent vibrational spectroscopy performed in a temporal region. Impulsive stimulated Raman scattering (ISRS) spectroscopy involves irradiating a sample with femtosecond pulse light to coherently excite a plurality of molecular vibrations in a stimulated Raman scattering process. The temporal profile representing the change in probe light due to the coherently excited molecular vibrations is Fourier transformed so that a frequency spectrum is acquired. In ISRS, since near infrared light, which is not greatly absorbed by a biological sample, can be used and a directional signal light is detected, the influence of background light resulting from a linear process can be minimized. The method described above has been applied to limited applications, such as studies on physical properties of solid and liquid molecules.

However, when terahertz spectroscopic information is used to analyze a biological sample, any of the detection methods described above, which allows change in the hydration state of the sample or any other macroscopic state change to be observed, hardly allows any information on a molecule or a group of molecules in a protein or any other biological substance to be extracted. The reason for this is that a terahertz vibrational spectrum derived from a biological molecule under physiological conditions has a shape that lacks any band structure because of mode denseness and damping, and that bands derived from a plurality of molecules in a biological sample are superimposed, resulting in a dull spectrum. Therefore, to acquire information on a molecule in a biological sample, it is necessary to use an approach for extracting mode information that characterizes the structure of the molecule from a structureless spectrum.

Further, as an application of ISRS to a field other than spectroscopic analysis, using the method described above to control a vibrational quantum state of a molecule is under study. In a biological application, when a biological macromolecule in a biological sample is excited in an ISRS process to vibrate in a collective mode, it is conceivable that higher-order structural change of the molecule may be induced and a physiological function in the organism may change. It has been pointed out that the viruses are possibly inactivated because the collective mode of a coat protein is excited in a stimulated Raman scattering process excited by the femtosecond pulse light and the structure of the protein is changed. It will be appreciated therefore, that excitation of a biological macromolecule in the collective mode affects an organism.

Accordingly, a need exists for a system and method of obtaining detailed molecular information in a non-invasive manner.

BRIEF SUMMARY OF THE INVENTION

In performing a Raman spectrum measurement on a target object containing a plurality of different molecules, such as a biological sample, there is provided a spectroscopic measurement apparatus capable of observing a Raman spectrum reflecting at least two types of vibrational mode information in a vibrational mode of any of the molecules in the object, vibrational frequency information and vibrational phase relaxation time information, and extracting band information reflecting the structure of the molecule from the Raman spectrum having featureless structure.

The invention is amenable to being embodied in a number of ways, including but not limited to the following descriptions. To achieve the object described above, at least one embodiment of the spectroscopic measurement apparatus comprises: (a) pump optical pulse train generation means for generating a pump optical pulse train having an arbitrary repetition rate; (b) irradiation means for irradiating a single location in an object to be measured (volume to be measured) with the pump optical pulse train and probe light so that impulsive stimulated Raman scattering is excited; (c) detection means for using the probe light to detect vibrational coherence information of the object to be measured in which the pump optical pulse train excites impulsive stimulated Raman scattering; and (d) spectrum acquisition means for acquiring a Raman spectrum of the object that reflects at least two types of information, vibrational frequency information and vibrational phase relaxation time information, from the vibrational coherence information of the object detected by the detection means for each of a plurality of different repetition frequencies of the pump optical pulse train.

When a molecule is excited by an optical pulse train so that impulsive stimulated Raman scattering occurs, it is known that when the repetition rate of the optical pulse train coincides with the frequency of a vibrational mode of the molecule and stimulated Raman scattering is excited by a plurality of optical pulses within the vibrational phase relaxation time of the vibrational mode, the band intensity of the vibrational mode is enhanced. The spectroscopic measurement apparatus according to the invention uses the fact that the vibrational phase relaxation time of a vibrational mode of a protein or any other substance in a biological sample depends on the vibrational mode and the viscosity to achieve the enhancement in the biological sample, whereby band information reflecting the molecular structure and the molecular environment can be extracted from a structureless spectrum. Therefore, the spectroscopic measurement apparatus according to the invention advantageously observes a Raman spectrum of a biological sample that cannot be observed by a Raman spectroscopy technique of related art.

In at least one implementation, the spectroscopic measurement apparatus further comprises: (e) memorizing means for memorizing (e.g., storage in a computer database) Raman spectra of a plurality of different molecules, the Raman spectra reflecting at least two types of vibrational information, vibrational frequency information and vibrational phase relaxation time information, and (f) operating means for performing chemometric analysis on the Raman spectrum of the object by using the Raman spectra memorized in the memorizing means. The spectroscopic measurement apparatus further including the two means performs chemometric analysis on a Raman spectrum of an object to be observed to classify the biochemical state of the object, estimate the concentration of each of the molecules contained in the object, or identify the molecules contained in the object.

In at least one implementation, the spectroscopic measurement apparatus further comprises: (g) spectrum comparing means for comparing the Raman spectrum of a molecule detected in the object by the operating means from the Raman spectrum of the object with a Raman spectrum of a desired target molecule having at least two types of known information, vibrational frequency information and vibrational phase relaxation time information.

In at least one implementation, the spectroscopic measurement apparatus further comprises: (h) frequency selecting means for selecting a band frequency of a desired Raman band from the Raman spectrum of the target molecule based on the comparison result obtained by the spectrum comparing means, and (i) frequency setting means for setting the repetition rate of the pump optical pulse train at the band frequency selected by the frequency selecting means. The apparatus further including the means described above can irradiate the object with the optical pulse train after a target molecule present in the object has been detected based on the Raman spectrum information of the object. In this way, only a specific molecular vibration in a target molecule contained in the object or a small group of molecules containing the target molecule contained in the object can be excited so that impulsive stimulated Raman scattering occurs, and the change in the molecular structure of the target molecule is advantageously induced.

In at least one implementation, the pump optical pulse train and probe pulse are generated in response to optical elements comprising: a laser source; a splitter coupled to said laser source for creating a first optical beam and a second optical beam; a variable optical delay configured for receiving said first optical beam and outputting a probe light; and a multiple optical pulse generator configured for receiving said second optical beam through multiple translation stages and outputting at least one said pump optical pulse train having an arbitrary repetition rate. In at least one implementation, the laser source comprises a single femtosecond laser source that outputs Transform Limit (TL) pulses which each have a temporal width shorter than 100 femtoseconds. In at least one implementation, said irradiation means comprises delivery optics for directing said probe light and said pump optical pulse train to an object volume containing a plurality of different molecules. In at least one implementation, wherein said detection means comprises: a light collection element configured for receiving light interacting with said object volume; and an optical detector configured for registering light collected by said light collection element.

In at least one implementation said spectrum acquisition means comprises: a computer processor with associated memory, electrically coupled to said pump optical pulse train generation means, irradiation means, detection means; programming executable on said computer processor and memory for, performing sweeping of repetition rate of said pump optical pulse train generation means, controlling delay within said probe light, and determining a Raman spectrum of the object volume including at least vibrational frequency information and vibrational phase relaxation time information, in response to vibrational coherence information determined in response to registration of light by said detection means for each of a plurality of different repetition frequencies of the pump optical pulse train.

One embodiment of the invention is a spectroscopic measurement apparatus for measuring a Raman spectrum of an object volume containing a plurality of molecules, comprising: (a) a laser source; (b) a splitter coupled to said laser source for creating a first optical beam and a second optical beam; (c) a variable optical delay configured for receiving said first optical beam and outputting an optical probe signal to excite impulsive stimulated Raman scattering; (d) a multiple optical pulse generator configured for receiving said second optical beam through multiple translation stages and outputting at least one pump optical pulse train having an arbitrary repetition rate; (e) delivery optics for directing said optical probe signal and at least one pump optical pulse train to an object volume containing a plurality of different molecules; (f) light collection element configured for receiving light interacting with said object volume; (g) optical detector configured for registering light collected by said light collection element; (h) a computer processor, and associated memory, coupled to said variable optical delay, said multiple optical pulse generator, and said optical detector; (i) programming executable on said computer processor and memory for, (i)(1) performing sweeping of repetition rate of said pump optical pulse train and translating stages within said multiple optical pulse generator, (i)(2) controlling delay within said variable optical delay, (i)(3) determining a Raman spectrum of the object volume including at least vibrational frequency information and vibrational phase relaxation time information, in response to vibrational coherence information determined in response to registration of light by said optical detector for each of a plurality of different repetition frequencies of the pump optical pulse train.

One embodiment of the invention is a method of performing spectroscopic measurements in response to light-molecule interaction on the molecules within an object, comprising the steps of: (a) generating pump optical pulse trains from a laser source; (b) generating a probe pulse; (c) guiding the pump optical pulse trains and probe pulse to an object having molecular species being measured; (d) obtaining vibrational coherence spectrum at arbitrary repetition frequency of the optical pulse trains; (e) scanning repetition rate of the pump optical pulse trains; (f) performing iterations of the above steps; and (g) obtaining Raman spectrum of the target from vibrational coherence spectra.

The present invention provides a number of beneficial elements which can be implemented either separately or in any desired combination without departing from the present teachings.

An element of the invention is a method, apparatus and system for performing spectroscopic measurements in response to light-molecule interaction on the molecules.

Another element of the invention is the generation of at least one optical probe signal and at least one pump optical pulse train configured for irradiating a molecular sample.

Another element of the invention is generation of the pump optical pulse train with an arbitrary repetition rate and capable of being swept.

Another element of the invention is obtaining spectroscopic measurements in response to Raman spectra captured from the molecular sample (e.g., transmissive and/or reflective) which includes at least two types of vibrational information including vibrational frequency information and vibrational phase relaxation time information.

Another element of the invention is the ability to generate the probe signal and pump optical probe pulse trains using a single laser.

Another element of the invention is the ability to compare Raman spectra captured in the device against a database of molecular information.

A still further element of the invention is the ability to test molecular and biological samples in a minimally invasive manner.

Further elements of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Embodiments of a spectroscopic measurement apparatus according to the invention will be described below in detail with reference to the drawings. It is noted that the embodiments do not intend to limit the invention.

Figure 1:
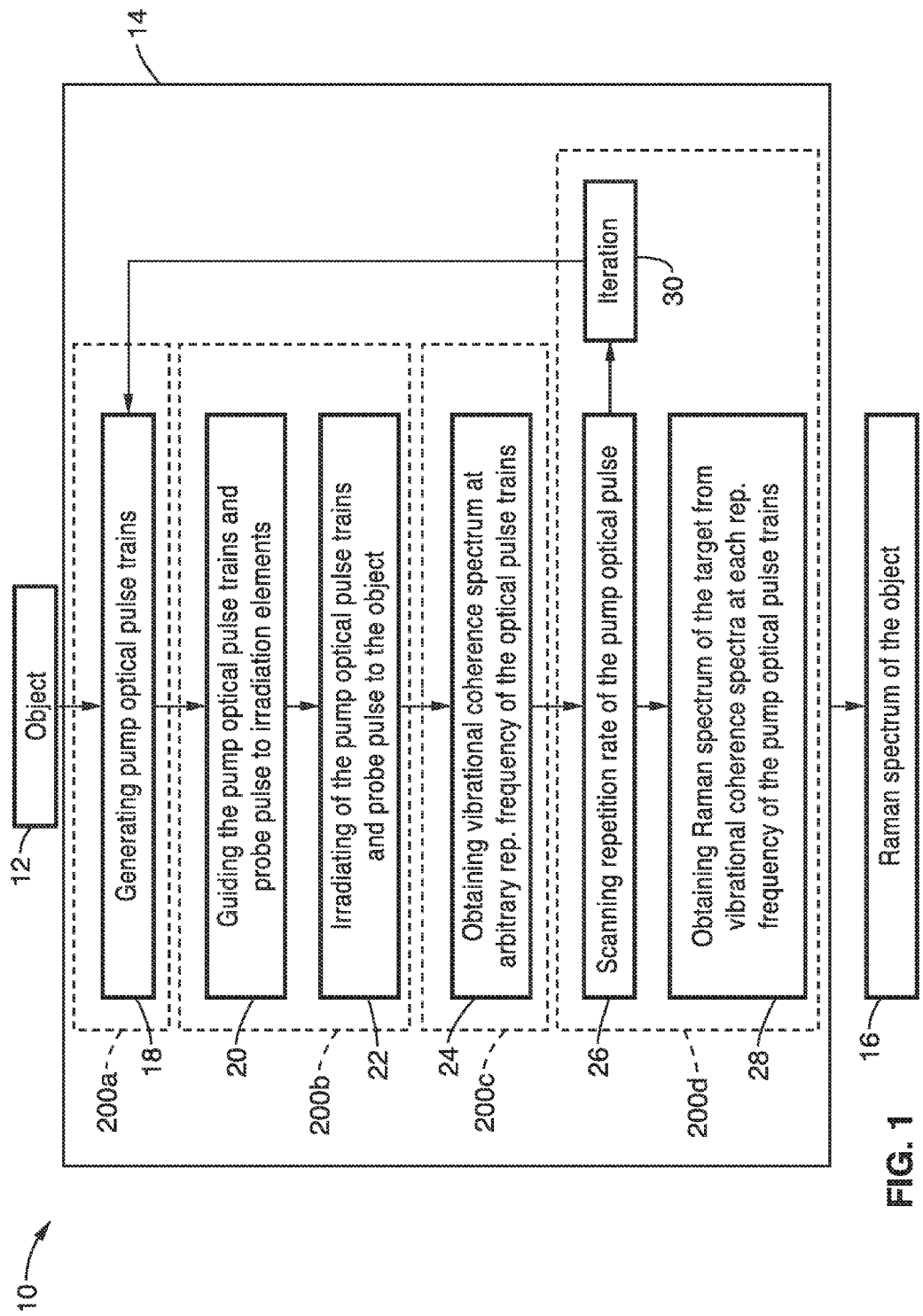
FIG. 1 is a flowchart of obtaining Raman spectra of a sample by a spectroscopic measurement apparatus according to an embodiment of the present invention.

FIG. 1 illustrates an example embodiment 10 of the present invention showing the operation of the spectroscopic apparatus 14 outputting Raman spectra 16 of an object 12 in a range from the sub-terahertz band to the terahertz band. An optical pulse train is generated from femtosecond optical pulses in step 18 which have an arbitrary repetition rate (any desired repetition rate) in a range from the sub-terahertz band to the terahertz band. Guiding of the optical pulse train (multiple optical pulses) and at least another single optical pulse (probe light) to irradiation elements as depicted in step 20. A single spatial location of a sample to be measured is irradiated in block 22 with the optical pulse train and probe light. A vibrational coherence signal from the object is obtained 24 when the arbitrary repetition rate optical pulse train excites impulsive stimulated Raman scattering, and the frequency spectrum of the vibrational coherence signal is acquired. Sweeping of the optical pulse repetition rate in a range from the sub-terahertz band to the terahertz band is performed in step 26 and iterations 30 performed for steps 18, 20, 22 and 24. A Raman spectrum of the sample is generated in step 28 from the frequency spectrum of the vibrational coherence signal detected for each of the swept repetitive frequencies of the optical pulse train to create the Raman spectrum 16 of the object.

By way of example and not limitation, the steps illustrated in FIG. 1 can be carried out by means elements 200a, 200b, 200c and 200d shown by the dotted lines for observing Raman spectra of the object according to an example embodiment of the invention. Hardware associated with these means elements are depicted in the block diagram of FIG. 2A and FIG. 2B. It should be appreciated that the steps can be grouped in different ways and performed by differing sets of hardware without departing from the teachings of the present invention. In the described implementation means element 200a comprises a pump optical pulse train generation means which is configured to performs step 18 of FIG. 1. Irradiation means element 200b is configured for carrying out steps 20, 22 shown in FIG. 1. Detection means element 200c is configured for performing step 24 shown in FIG. 1. Spectrum acquisition means 200d is configured for carrying out steps 26, 28 and 30 of FIG. 1.

Figure 2A:
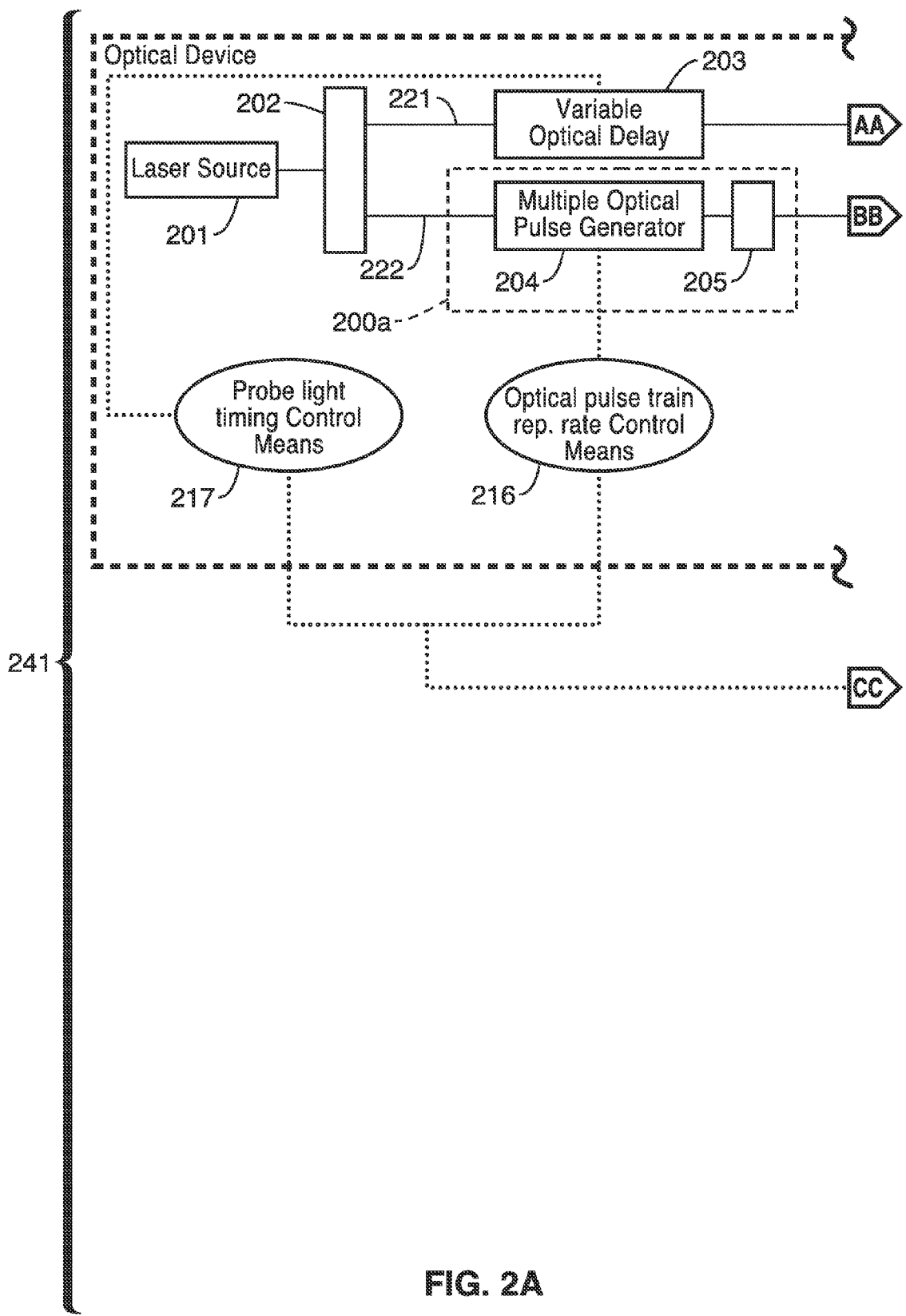
FIG. 2A and FIG. 2B are schematics of a spectroscopic measurement apparatus according to an embodiment of the present invention.
Figure 2B:
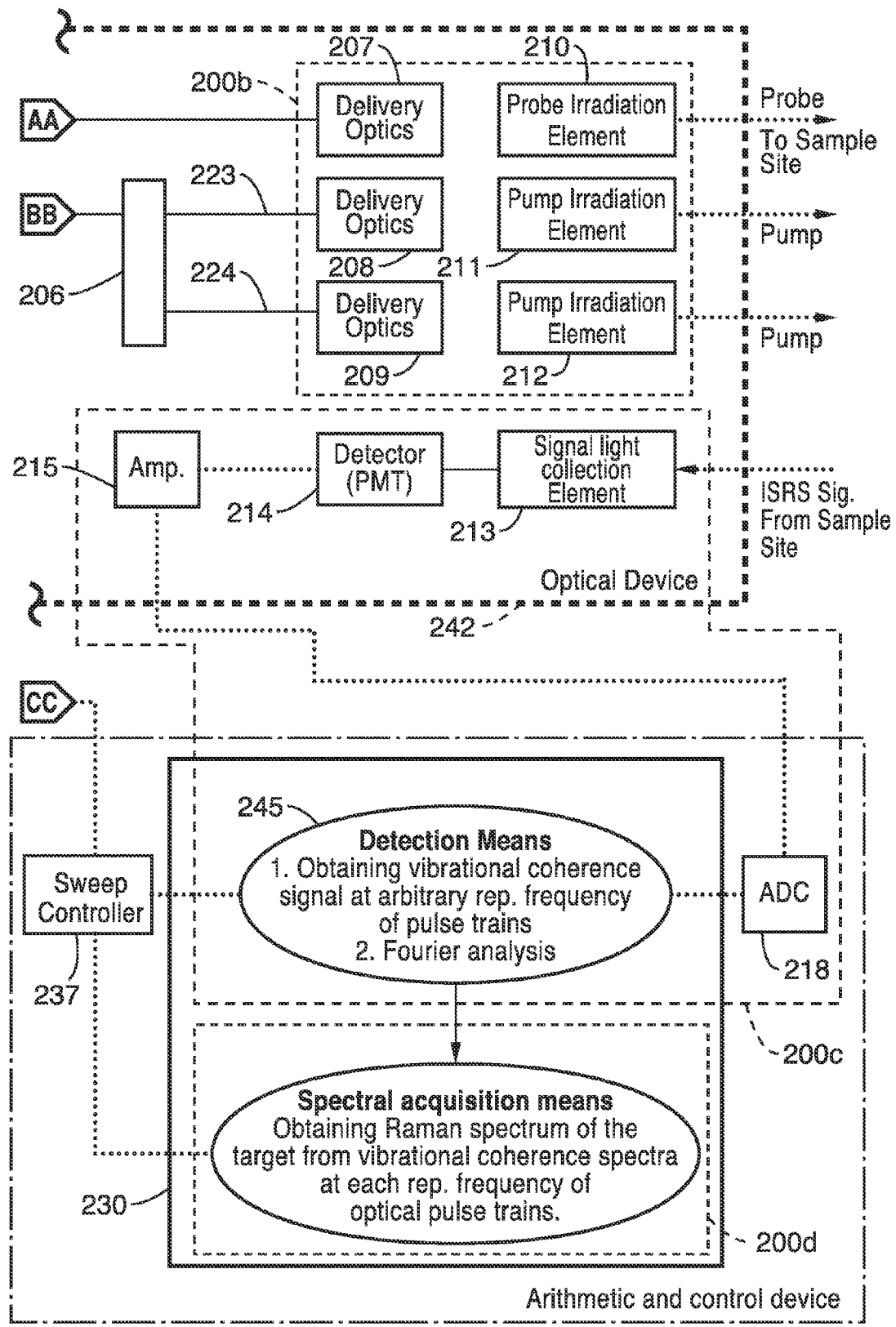

FIG. 2A and FIG. 2B illustrate an example embodiment of a spectroscopic measurement apparatus according to the invention. An example of the object to be measured by the spectroscopic measurement apparatus is liquid or solid formed of cells, tissue, or biochemical components, and a biological sample including an organism. It should be noted that connection blocks (e.g., marked "AA", "BB", "CC" and so forth) are used in a number of the figures to detail the interconnection of signals from one sheet to the associated sheet, and will not be described in regard to traversing between drawing sheets.

The following section describes in more detail the method of measuring a Raman spectrum of a sample with reference to FIG. 2A and FIG. 2B. A spectroscopic measurement apparatus 241 comprises an optical device 242 in combination with an arithmetic and control device 243.

The optical device 242 can be configured in a variety of different ways, as described in the following sections. A single laser source 201 can be used, such as by way of example comprising a femtosecond titanium-sapphire laser that outputs TL pulses which each have a temporal width shorter than 100 femtoseconds, with the average laser output being on the order of several hundreds of milliwatts. The wavelength of the pulse light which is output from the laser preferably falls within a near infrared band, for example, ranging from 750 nm to 850 nm. Laser output is shown coupled to a splitter 202 from which are optical paths 221 and 222 derive. The pulse light being output from the laser is split, such as into two beams by a splitter 202 from which one of the pulse light fluxes are then guided along optical path 221. The pulse light flux is used as the probe light for detecting the state of molecular vibration of the object to be excited so that stimulated Raman scattering occurs. The other pulse light flux from the splitter is guided along optical path 222 for generating excitation pulse light for exciting stimulated Raman scattering in the sample.

Along optical path 221 is a variable optical delay 203, whose timing is controlled by timing control means 217, prior to reaching irradiation means 200b and delivery optics 207 and irradiation element 210. The variable optical delay 203 may comprise, for example, a mirror or a reflector (not shown), or any optical elements or combination thereof for providing the delay as will be known to one of ordinary skill in the art. It should be noted that the delay can be implemented, for example, by manipulating the light of optical path 221 which is folded 90 degrees by a mirror disposed along optical path 221, folded 180 degrees by a reflector, and finally brought back to the initial optical path 221 by another mirror disposed in the optical path 221 to create the delay. The reflector is disposed on a movable stage so that the optical length of the optical path 221 along which the probe light travels can be changed.

Along optical path 222 are a pump optical pulse train generation means 200a comprising a multiple optical pulse generator 204 controlled by rate control means 216 and dispersion compensator (DC) 205 shown for generating the optical pulse train (multiple optical pulses), the latter of which is disposed as required. The femtosecond pulse light guided to the optical path 222 is converted into an optical pulse train formed of femtosecond optical pulses (multiple optical pulses) having a pulse repetition rate in a range from the sub-terahertz band to the terahertz band, specifically, ranging from 0.1 to 20 terahertz, in the multiple optical pulse generator 204 disposed in the pump optical pulse train generation means 200a.

Output from dispersion compensator 205 is split by a splitter 206 into paths 223 and 224. One optical path 223 is coupled to delivery optics 208 and irradiation element 211 of block 200b, while optical path 224 is coupled to delivery optics 209 and irradiation element 212 of block 200b. As can be seen, Irradiation means 200b is shown comprising sets of delivery optics 207, 208, 209 and irradiation elements 210, 211, and 212 for the optical probes and pump signals.

In step 24 described in FIG. 1, a vibrational coherence signal from the object is detected in response to multiple optical pulses used to excite impulsive stimulated Raman scattering in the sample, which is irradiated with the probe light delayed from the excitation event (described later). In this process, any of the following temporal profiles may need to be measured: a temporal profile representing the change in the intensity of the diffracted probe light, the shift in the frequency of the probe light, and/or the rotation of the polarization of the probe light due to the interaction between the sample and the probe light. The temporal profile is measured by detection means 200c in combination with probe light timing control means 217. A spectrum acquisition means 200d in combination with a pump optical pulse train repetition rate control means 216 performs steps 26, 28 shown in FIG. 1, comprising measuring the frequency spectrum of the vibrational coherence signal from the sample for each of the repetition frequencies of the optical pulse train, and deriving and summing the frequency spectra from the sample for the repetition frequencies. The Raman spectrum derived from the sample over the measurement region is thus acquired.

Figure 2C:
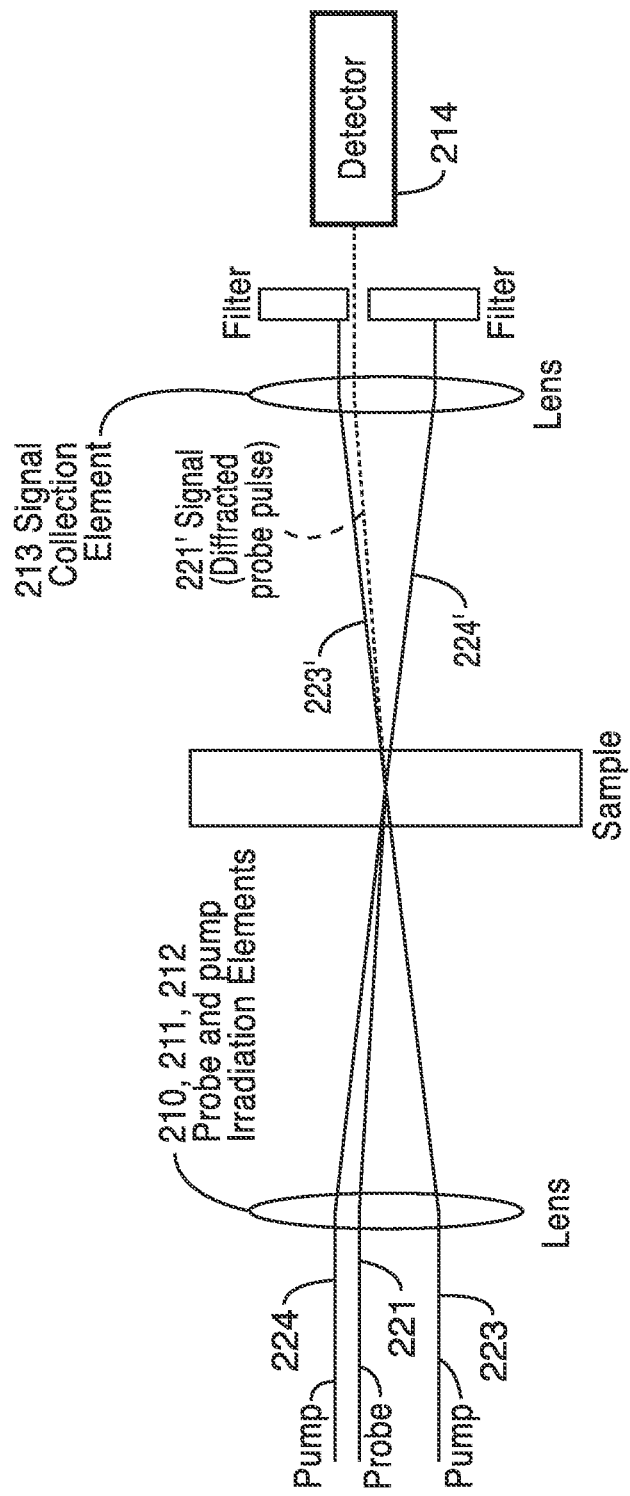
FIG. 2C and FIG. 2D are schematics of irradiating a sample with pump light and probe light for detecting signal light in the spectroscopic measurement apparatus according to an embodiment of the present invention.
Figure 2D:
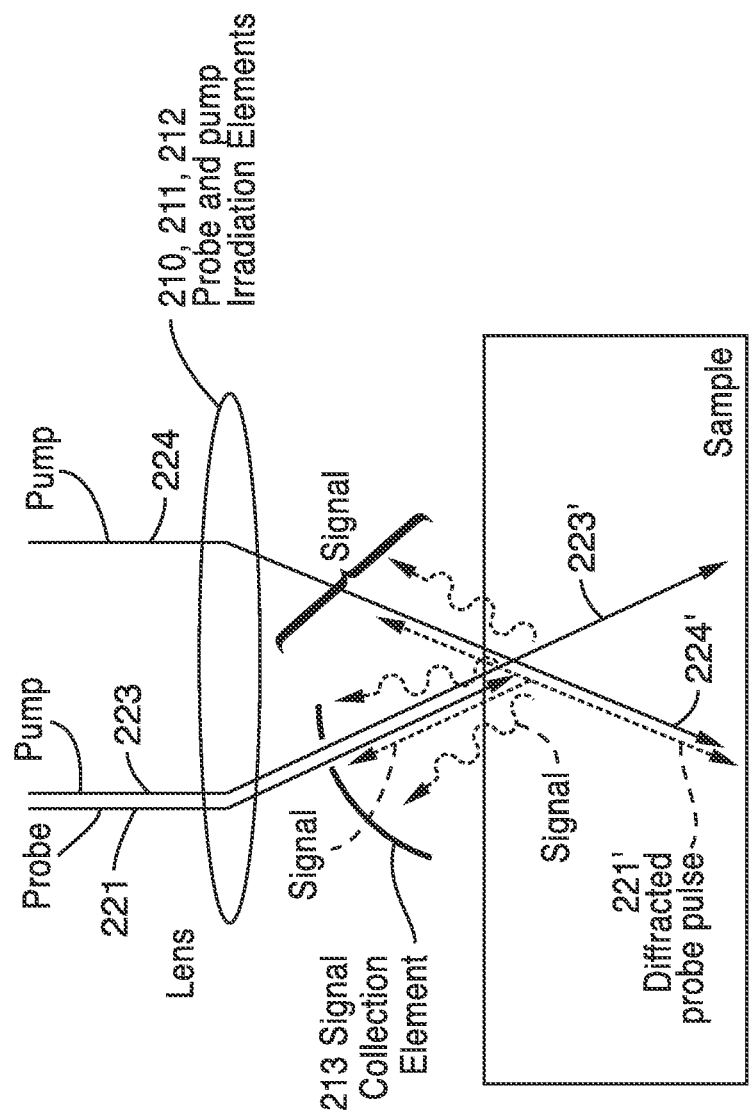

The ISRS signal shown in FIG. 2A and FIG. 2B comprises probe light diffracted by the transient grating as collected by a signal light collection element 213 and detected by an optical detector 214, which can be amplified 215 and detected by a converter, such as analog-to-digital converter 218 in combination with detector 245 within detection means 200c coupled to a spectral acquisition means 200d. It will be noted that sweep controller 237 is coupled to detector 245, spectral acquisition means 200d as well as to timing control means 217 and rate control means 216. FIG. 2C and FIG. 2D are described in a later section.

Figure 3A:
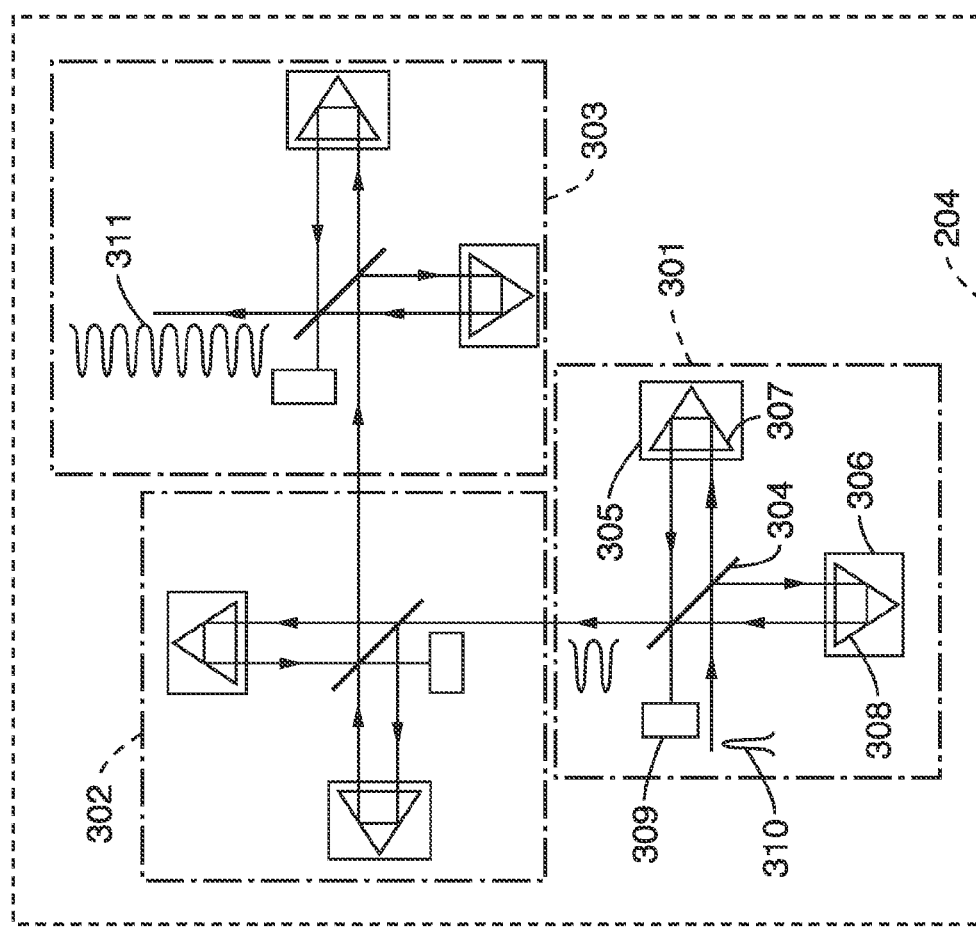
FIG. 3A and FIG. 3B are schematics of multiple optical pulse generators used in the spectroscopic measurement apparatus according to an embodiment of the present invention.

FIG. 3A exemplifies an optical arrangement of the multiple optical pulse generator 204 of FIG. 2A and FIG. 2B based on a Michelson interferometer 301. The Michelson interferometer 301 includes a beam splitter 304, translation stages 305 and 306, reflectors 307 and 308 disposed on the translation stages, and a beam damper 309. Each of the reflectors may be replaced with a pair of mirrors, and only one of the translation stages may be movable. In the Michelson interferometer, optical pulses created from an incident optical pulse 310 is split by beam splitter 304 into two whereby the optical path lengths before combination at the beam splitter can be set at different values. In the multiple optical pulse generator shown in FIG. 3A, the interferometer 301 and other two interferometers 302 and 303 are connected serially, and an optical pulse train 311 formed of eight optical pulses can be generated from the incident pulse light 310. In this case, when the differences in optical length between the two optical paths in the interferometers 301, 302, and 303 are set at, for example, 0.3 mm, 0.6 mm, and 1.2 mm, respectively, an optical pulse train having a repetition rate of 1 terahertz is generated. Similarly, when N interferometers of this type are connected serially, a pulse train formed of $2^N$ optical pulses can be generated.

Figure 3B:
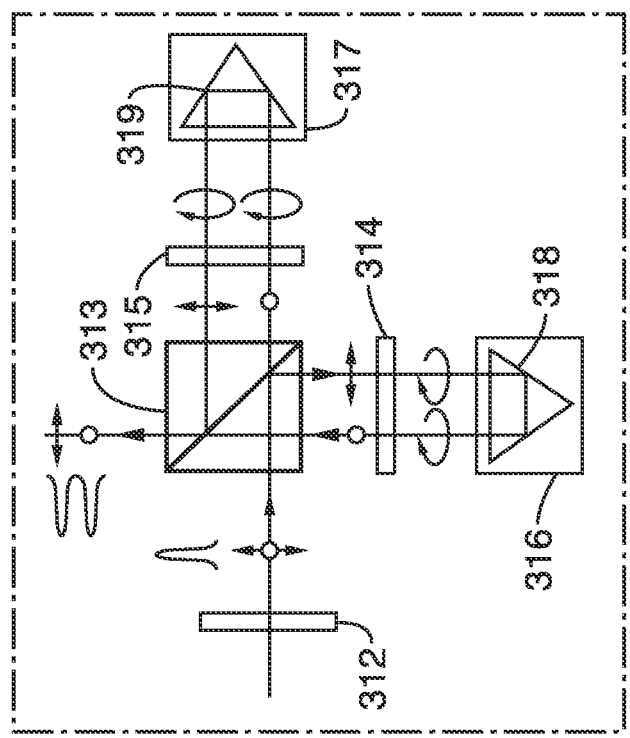

The device configuration shown in FIG. 3B is another form of the Michelson interferometer which can be used in the multiple optical pulse generator 204 of FIG. 2A and FIG. 2B. The interferometer, which is a combination of a polarization beam splitter 313, a half wave plate 312, and quarter wave plates 314 and 315, also functions as an optical isolator. Translation stages 316 and 317 are shown respectively with reflectors 318 and 319. Since no return light from the interferometer is produced in this configuration, light loss is minimal and interferometers can be cascaded. When N interferometers of this type are connected serially, a pulse train formed of $2^N$ optical pulses can be generated from an incident pulse light.

The repetition rate of the optical pulse train generated in the multiple optical pulse generator can be set at a desired value by the optical pulse train repetition rate control means 216 of FIG. 2A and FIG. 2B, which is now specifically described below. In each of the interferometers shown in FIG. 3A, the difference in optical length between the optical path along which one of the optical pulses (which are split at beam splitter 304) travels and the optical path along which the other optical pulse travels can be adjusted by translating the translation stage 305 or 306. The rate control means 216 shown in the embodiment of FIG. 2A and FIG. 2B is configured with the translation stages electrically connected to a sweep controller 237 and a computer 230 housed in the arithmetic and control device 243 via communication cables. Therefore, a control program loaded in computer 230 can instruct the sweep controller 237 to translate the translation stages. Further, rate control means 216 can rely on the control program to set the differences in optical length produced in the N interferometers in such a way that the temporal intervals between the $2^N$ optical pulses outputted from the multiple optical pulse generator are the same.

The dispersion compensator 205 may be disposed downstream of the multiple optical pulse generator 204 along optical path 222 to compensate for temporal width broadening of the optical pulses due to group velocity dispersion imparted over the optical path from the light source to the generator. By way of example, it will be appreciated that the dispersion compensator can be formed using any of a pair of chirp mirrors, a pair of gratings, or a pair of prisms.

Each of the multiple optical pulses is further split into two beams in a splitter 206, and the split optical pulses travel along respective optical paths 223 and 224. The multiple optical pulses traveling along optical path 223 are called excitation optical pulse 1, and the multiple optical pulses traveling along optical path 224 are called excitation optical pulse 2. The sample is irradiated with the probe light having passed through variable optical delay 203, the excitation optical pulse 1, and excitation optical pulse 2 through irradiation means 200b. Delivery optics 207, 208, and 209 and irradiation elements 210, 211, and 212 are all shown within irradiation means 200b. Each of the delivery optics comprises either spatial optics formed of a group of mirrors and lenses or a hollow fiber. The irradiation elements 211 and 212, each of which is formed of a mirror and (or) a lens, are arranged in such a way that a single area of the sample is irradiated with the excitation optical pulse 1 and the excitation optical pulse 2 relatively angled so that the two excitation optical pulses intersect in the sample and form a transient grating. On the other hand, the irradiation element 210, which is formed of a mirror and (or) a lens, is arranged in such a way that the area where the transient grating is formed is irradiated with the probe light with the Bragg condition satisfied. An example of the irradiation form using the two excitation pulse light fluxes and the probe light may be based on an optical arrangement typically called BOX-CARS.

FIG. 2C and FIG. 2D illustrate sample irradiation according to the present invention. The optical beams 221, 223 and 224 are shown from FIG. 2A and FIG. 2B distributed by irradiation element 210, 211 and 212 (e.g., a lens) and striking a sample. Resultant beams exiting the sample comprise optical beams 221', 223' and 224', subject to receipt by a collection element 213, a filter, and a detector 214.

When the sample is irradiated and excited with the excitation optical pulse 1 and the excitation optical pulse 2 so that impulsive stimulated Raman scattering occurs, a transient grating is formed in the sample. As previously described, the probe light diffracted by the transient grating is collected by a signal light collection element 213 and detected by an optical detector 214. The optical detector 214 is a photomultiplier or a photodiode. To efficiently collect the signal, the signal light collection element 213 is desirably disposed on the opposite side of the sample to the irradiation elements so that the probe light diffracted by the transient grating in the direction in which the Bragg condition is satisfied and passing through the sample is collected, as shown in FIG. 2C. Depending on the sample, however, the signal light collection element may be disposed on the side of the sample where the irradiation elements are disposed and the diffracted probe light reflected off or scattered by the sample is collected, as shown in FIG. 2D.

The signal representing the intensity of the diffracted probe light undergoes photoelectric conversion in the optical detection 214, is amplified by an amplifier 215, and is then captured by the computer 230 housed in the arithmetic and control device 243 via an A/D converter 218 also housed in the arithmetic and control device 243.

The femtosecond optical pulses, which form the multiple optical pulses (optical pulse train), coherently excite a plurality of vibrational states of a molecule contained in the sample. Since each of the coherently excited states (vibrational coherence) is a non-stationary state, it temporally develops and molecular vibration occurs accordingly. The vibrational coherence that temporally develops is maintained for a fixed time (vibrational phase relaxation time). A vibrational coherence signal from the sample derived from the molecular vibrations in the sample can be observed by using the method described below.

The intensity of the diffracted probe light described above reflects the change in the transient grating formed in the sample, that is, the transient spatial distribution of the refractive index. On the other hand, the vibrational coherence of the molecule in the sample produced in the impulsive stimulated Raman scattering process induced by the excitation pulse light modulates the transient change in the refractive index at the beat frequency corresponding to the difference in energy between the vibrational ground state and the vibrational excited state, in other words, the frequency of the vibrational mode. Therefore, sweeping the timing at which the sample is irradiated with the probe light relative to the excitation pulse light and recording the intensity of the diffracted probe light allows the recorded temporal profile of the diffraction intensity to reflect the vibrational coherence signal from the molecule.

Probe light timing control means 217 in this embodiment is configured for activating the translation stages, which are disposed in the variable optical delay 203 and on which a pair of reflectors or mirrors are disposed, and has a structure in which the translation stages, sweep controller 237, and computer 230 are electrically connected via communication cables. The control program running on computer 230 preferably operates the translation stages via sweep controller 237. Detection means 200c is formed of not only the program running on computer 230 and having functions of controlling the translation stages, performing arithmetic operations, and acquiring data, but also includes signal light collection element 213, optical detector 214, amplifier 215, and A/D converter 218. The detection means instructs probe light timing control means 217 to set the translation stages in variable optical delay 203 in predetermined positions. Optical detector 214 then detects the probe light diffracted in the sample, and the intensity of the probe light is captured from A/D converter 218 to computer 230 and stored therein. This process is iterated multiple times while the positions of the translation stages are swept. In this way, detection means 200c measures the vibrational coherence signal provided when the sample is excited at an arbitrary repetition rate of the optical pulse train so that impulsive stimulated Raman scattering occurs. Specifically, the temporal profile of the vibrational coherence signal can be measured at sufficiently fine temporal resolution by successively changing the amount of change in optical length of the optical path 221 produced in the variable optical delay 203 in increments of a fixed value ranging from one to several micrometers and recording the intensity of the diffracted probe light whenever the optical length is changed.

In addition, detection means 200c is configured for performing Fourier transform operations on the vibrational coherence signal produced in the sample in response to irradiation from the multiple optical pulses at the arbitrary repetition rate, whereby the frequency spectrum of the signal is provided.

Alternatively, when pulse light having a temporal width wider than the duration of the multiple optical pulses is used as the probe light, the frequency spectrum of the vibrational coherence signal can be measured without sweeping the positions of the translation stages in variable optical delay 203. An apparatus configuration that enables such measurement will be described later in detail.

It should be appreciated that in the vibrational coherence signal which is observed when the sample is excited by the multiple optical pulses, only the vibrational coherence component of the vibrational mode whose vibrational frequency coincides with the repetition rate of the optical pulse train is enhanced, whereas the vibrational coherence components of the vibrational modes having other vibrational frequencies are not enhanced. Therefore, the frequency spectrum described above only shows the Raman band corresponding to the vibrational mode whose vibrational frequency coincides with the repetition rate of the optical pulse train.

Therefore, to measure Raman spectra in a frequency width broad enough to observe a Raman band of a sample in an arbitrary region ranging from the sub-terahertz band to the terahertz band, the optical pulse train repetition rate control means 216 needs to sweep the repetition rate of the optical pulse train. The spectrum acquisition means 200d is the program running on computer 230 shown in FIG. 2A and FIG. 2B and having functions of controlling the translation stages, performing arithmetic operations, and acquiring data. The spectrum acquisition means can instruct optical pulse train repetition rate control means 216 to set the repetition rate of the optical pulse train at an arbitrary specific frequency, and then acquire the frequency spectrum of the vibrational coherence signal from the sample detected by detection means 200c. The spectrum acquisition means further has a function of iterating the process described above while sweeping the repetition rate of the optical pulse train, and acquiring the frequency spectrum of the vibrational coherence signal from the sample for each of the repetition frequencies of the optical pulse train.

The spectrum acquisition means 200d then calculates the band intensity of the Raman band that appears in the frequency spectrum of the vibrational coherence signal acquired for each of the repetition frequencies of the optical pulse train. Calculating the band intensity for all the swept repetition frequencies can produce the Raman spectra of the sample over the area across which the repetition rate is swept. It will be appreciated that the band intensity, the peak intensity of the Raman band or the intensity corresponding to the area of the band may be calculated.

The following describes how the Raman spectrum of the sample obtained by plotting the band intensity of the vibrational coherence signal measured from the sample for each of the different repetition frequencies of the optical pulse train described above is a Raman spectrum that reflects two types of vibrational mode information, vibrational frequency information and vibrational phase relaxation information, in the vibrational mode of a molecule in the sample. Another description will be made of an advantage of the method of the invention; Measuring Raman spectra of a mixed sample containing a plurality of different chemical components (molecules), such as a biological sample, in accordance with the method of the invention provides a Raman spectrum including extracted information on the bands of the molecules contained in the sample, unlike a Raman spectrum of the sample observed by using Raman spectroscopy of related art that has a broad shape and lacks any structure with reference to diagrammatic spectra shown in FIG. 4A through FIG. 4F.

Figure 4A:
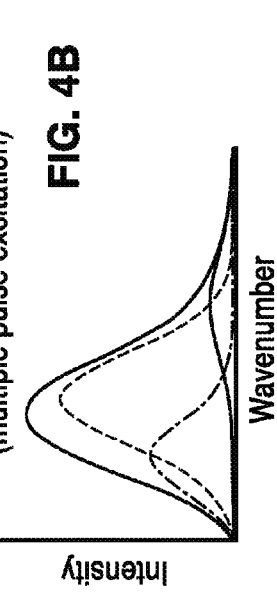
FIG. 4A through FIG. 4F are graphs of Raman spectra for a mixed sample containing a plurality of different kind of molecules generated by a spectroscopic measurement apparatus according to an embodiment of the present invention.
Figure 4C:
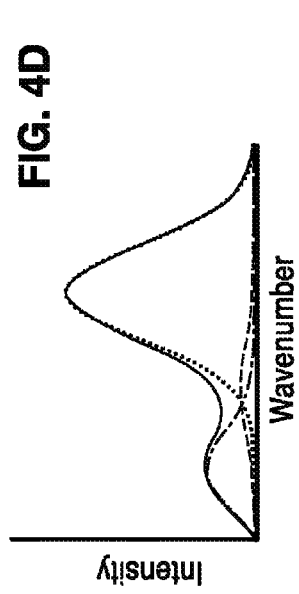
Figure 4E:
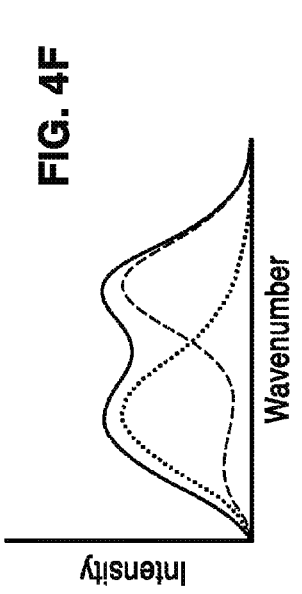

FIG. 4A, FIG. 4C, and FIG. 4E show diagrammatic Raman spectra observed by using Raman measurement as known in the art, more specifically, spontaneous Raman spectroscopy or impulsive stimulated Raman scattering spectroscopy based on single optical pulse excitation. The spontaneous Raman scattering spectroscopy and the impulsive stimulated Raman scattering spectroscopy based on single optical pulse excitation are known to provide Raman spectrum information equivalent to each other. In FIG. 4A, the spectrum indicated by the solid line represents a Raman spectrum derived from a molecule A. It is assumed that the Raman spectrum is formed of three different Raman bands of vibrational modes, modeA1 (dashed line), modeA2 (broken line), and modeA3 (dotted line). In FIG. 4C, the spectrum indicated by the solid line represents a Raman spectrum derived from a molecule B. It is assumed that the Raman spectrum is formed of three different Raman bands of vibrational modes, modeB1 (dashed line), modeB2 (broken line), and modeB3 (dotted line). In FIG. 4E, the spectrum indicated by the solid line represents a Raman spectrum of a mixed sample containing the molecules A and B, and the dotted line and the broken line indicate Raman spectra derived from the molecules A and B, respectively, which contribute to the Raman spectrum of the mixed sample.

As seen from the figures, the Raman spectra observed by using Raman spectroscopy provide a less characteristic spectra because Raman bands of the plurality of molecules contained in the mixed sample are overlapped.

It will be appreciated that a Raman spectrum of a mixed sample obtained by using the present method reflects two types of vibrational mode information, vibrational frequency information and vibrational phase relaxation information, in the vibrational mode of a molecule in the sample.

It is known that in general, when multiple optical pulses having a predetermined single repetition rate are used to excite impulsive stimulated Raman scattering in a pure substance formed of one type of chemical component (molecule), and a vibrational mode whose frequency coincides with the repetition rate of the multiple optical pulse train is present in the pure substance, the selectivity of the vibrational coherence signal in the vibrational mode produced in the impulsive stimulated Raman scattering process is improved (see article by A. M. Weiner et al. "Femtosecond multiple pulse impulsive stimulated Raman scattering spectroscopy" J. Opt. Soc. Am. B, Vol. 8 1264 (1991)). The selectivity is determined by considering the relationship between the vibrational phase relaxation time in the vibrational mode and the irradiation time of the multiple optical pulse train. Specifically, when the vibrational phase relaxation time in the vibrational mode is longer than the irradiation time of the multiple optical pulse train, the vibrational coherence signal in the vibrational mode is enhanced when the multiple optical pulse train excites impulsive stimulated Raman scattering, whereas when the vibrational phase relaxation time in the mode is much shorter than the irradiation time of the multiple pulse train, the vibrational coherence signal is not enhanced. That is, it is shown that the method described above allows the magnitude of the vibrational coherence to relatively increases or decreases in accordance with the vibrational phase relaxation time of the vibrational mode.

However, the method only advantageously enhances the vibrational mode of a pure substance, but cannot extract information on characteristic bands having broad frequency widths (vibrational frequency information) of a plurality of different molecules, to which the invention is directed, in a mixed sample, such as a biological sample. In the invention, the repetition rate of the multiple pulse train is changed in correspondence with the information on the bands (vibrational frequency information) of the plurality of different molecules to individually increase or decrease the band information so that it can be extracted as a discriminable feature.

It has been ascertained that the vibrational phase relaxation time in a vibrational mode of a biological macromolecule, such as a protein, not only varies due to intramolecular and intermolecular interaction in a plurality of chemical substances that form the biological macromolecule, but also varies due to the viscosity, the temperature, or any other physical environments. It can thus be understood that when multiple optical pulses having a variable repetition rate are used to excite a mixed sample containing biological macromolecule to provide impulsive stimulated Raman scattering as described above, not only does the vibrational phase relaxation time of a plurality of molecules contained in the sample vary in accordance with intramolecular and intermolecular interaction in the molecules and physical environment thereof, but also the increase or decrease in the vibrational coherence signal in the vibrational mode of each of the molecules varies. As a result, different Raman bands reflecting the variances described above, specifically reflecting the two types of vibrational mode information including vibrational frequency information and vibrational phase relaxation information, appear in the frequency spectrum of the vibrational coherence signal. Therefore, even when frequency of the vibrational mode of each of different kind of molecules in the sample degenerates and is hence cannot provide molecular discrimination, the use of vibrational phase relaxation time information generated according to the invention allows the plurality of vibrational modes to be properly discriminated from one another.

Figure 4B:
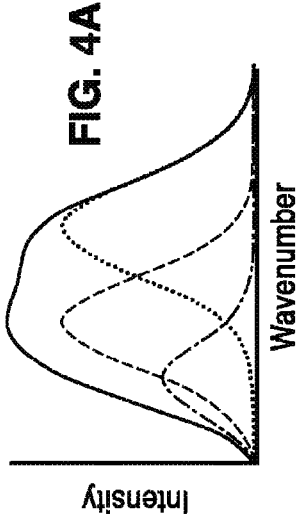
Figure 4D:
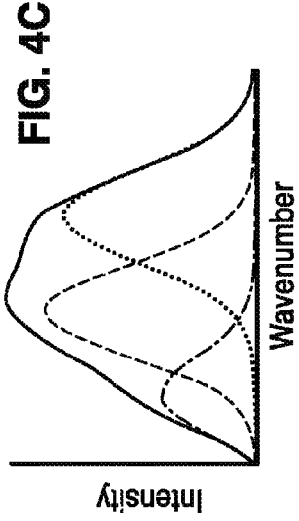
Figure 4F:
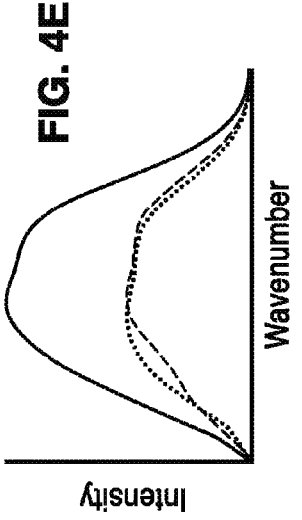

FIG. 4B, FIG. 4D and FIG. 4F illustrate an advantageous effect provided when the spectroscopic measurement apparatus according to the invention is used to observe a Raman spectrum of a mixed sample containing a plurality of different molecules. It is assumed in the description that the molecules are proteins or any other biological molecules contained in a biological sample. FIG. 4B, FIG. 4D and FIG. 4F depict Raman spectra obtained when multiple optical pulses excite the sample containing the molecule A, the sample containing the molecule B, and the mixed sample containing the molecules A and B, respectively. It is assumed that the vibrational phase relaxation time in modeA3, one of the vibrational modes of the molecule A, is sufficiently shorter than the irradiation time of the multiple optical pulses and the vibrational phase relaxation time in any of the other vibrational modes is longer than the irradiation time of the multiple optical pulses. In this case, the Raman spectrum of the molecule A indicated by the solid line in FIG. 4B has reduced contribution of the Raman band of modeA3 but is characterized by the Raman bands of modeA1 and modeA2. On the other hand, it is assumed in the molecule B that the vibrational phase relaxation time in modeB2 is sufficiently shorter than the irradiation time of the multiple optical pulses and the vibrational phase relaxation time in any of the other modes is longer than the irradiation time of the multiple optical pulses. In this case, the Raman spectrum of the molecule B indicated by the solid line in FIG. 4D has reduced contribution of the Raman band of modeB2 but is characterized by the Raman bands of modeB1 and modeB3. As described above, the spectra shown in FIG. 4B and FIG. 4D contain the information on the frequency of molecular vibration modes (Raman bands of modeA1, modeA2, modeA3, modeB1, modeB2, and modeB3) and the vibrational phase relaxation information (increase or decrease of the bands in accordance with the vibrational phase relaxation time in the vibrational modes), whereby the information on the Raman bands of the molecules uniquely appears in the spectra.

The Raman spectrum of the mixed sample containing the molecules A and B is the linear sum of the Raman spectra of the molecules, and is indicated by the solid line shown in FIG. 4F. The Raman spectrum of the mixed sample also contains the information on the frequency of the vibrational modes of the molecules (Raman bands of modeA1, modeA2, modeA3, modeB1, modeB2, and modeB3) and the vibrational phase relaxation information (increase or decrease of the bands in accordance with the vibrational phase relaxation time in the vibrational modes), whereby the information on the bands of the molecules A and B is clearly shown. Comparing the Raman spectrum of the mixed sample shown in FIG. 4F measured by using the method according to the invention with the Raman spectrum shown in FIG. 4E acquired by the Raman measurement of relate art, it is clear that the present measurement method allows observation of a Raman spectrum showing the information on the bands of the molecules A and B extracted from the featureless broad Raman spectrum of the mixed sample. Further, measuring the Raman spectra of the molecules A and B in advance, which are indicated by the solid lines in FIG. 4B and FIG. 4D, and storing the Raman spectra as known spectral information allow the information on the proportion of each of the chemical components contained in the mixed sample to be provided from the Raman spectrum of the mixed sample.

As described above, according to the spectroscopic measurement apparatus of the invention, when the multiple optical pulses having a variable repetition rate are used to excite impulsive stimulated Raman scattering in a specimen, the information on the frequency of the vibrational modes of the molecules in the sample and the information on the phase relaxation time of the vibrational modes can be used to discriminate the vibrational modes, whereby a Raman spectrum of the mixed sample including extracted information on the bands of the molecules can be measured. In this way, precise analysis of the chemical components (molecules) in the mixed sample is advantageously made, as compared to analysis using a Raman spectrum of the sample obtained by Raman spectroscopic measurement of related art, such as spontaneous Raman scattering spectroscopy or impulsive stimulated Raman scattering spectroscopy based on single pulse excitation.

Figure 5:
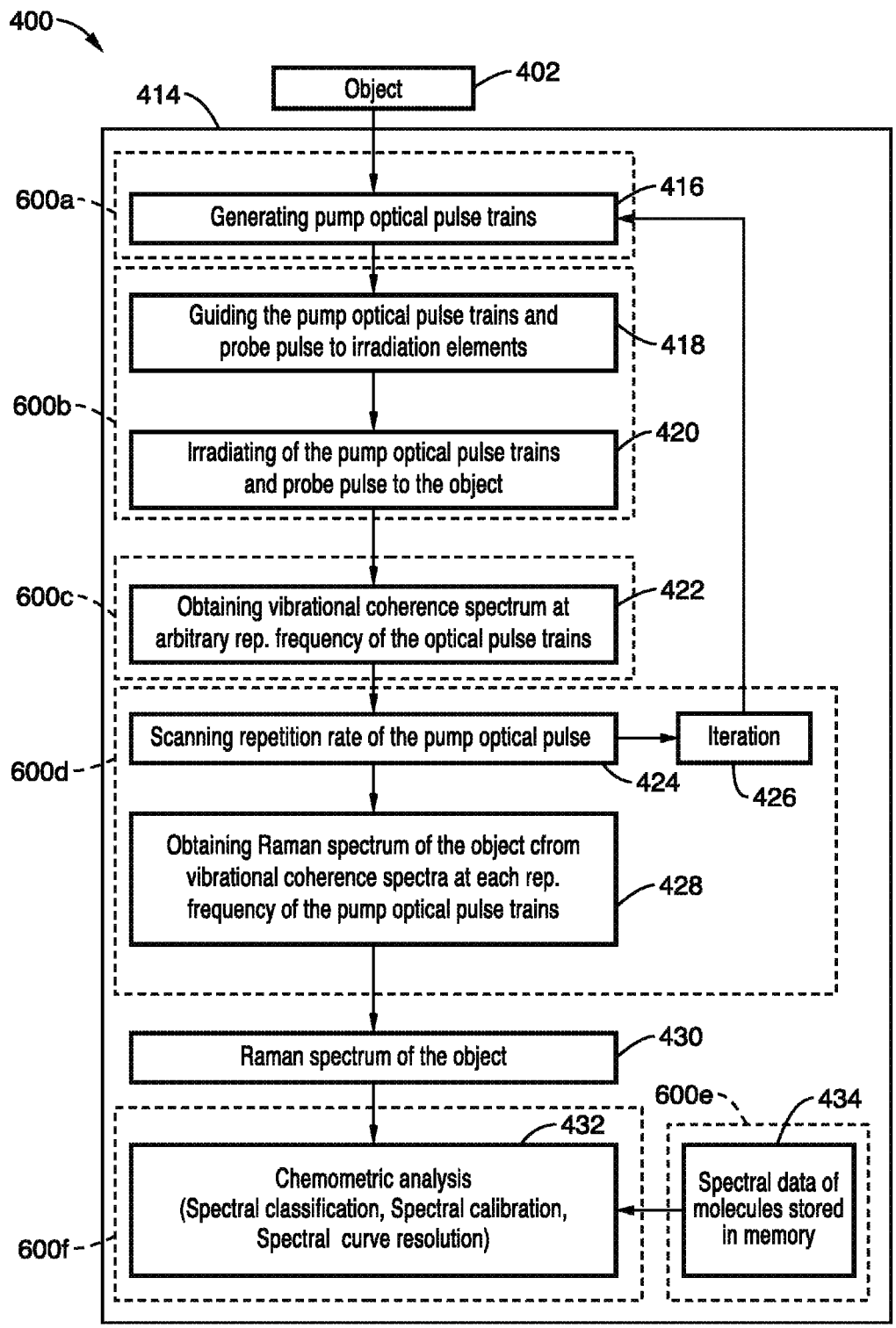
FIG. 5 is a flowchart of performing chromometrics analysis within a spectroscopic measurement apparatus according to an embodiment of the present invention.
Figure 6A:
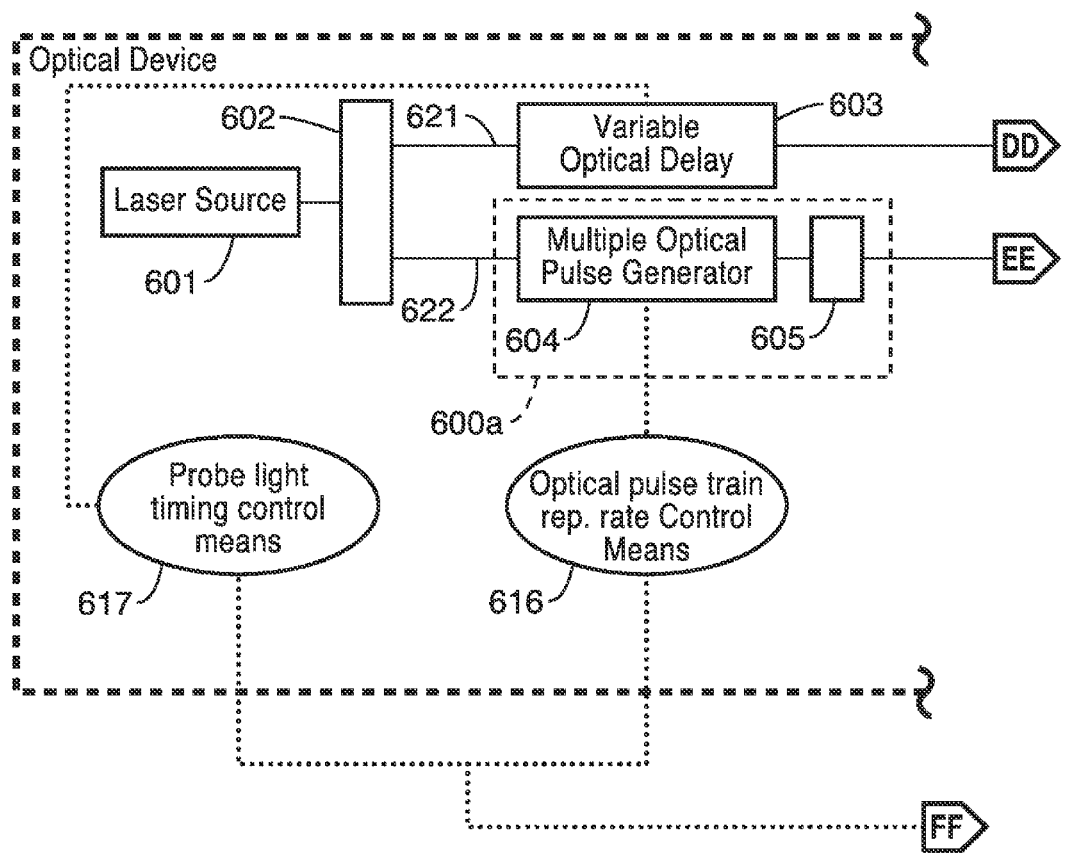
FIG. 6A and FIG. 6B are schematics of a spectroscopic measurement apparatus according to an embodiment of the present invention.
Figure 6B:
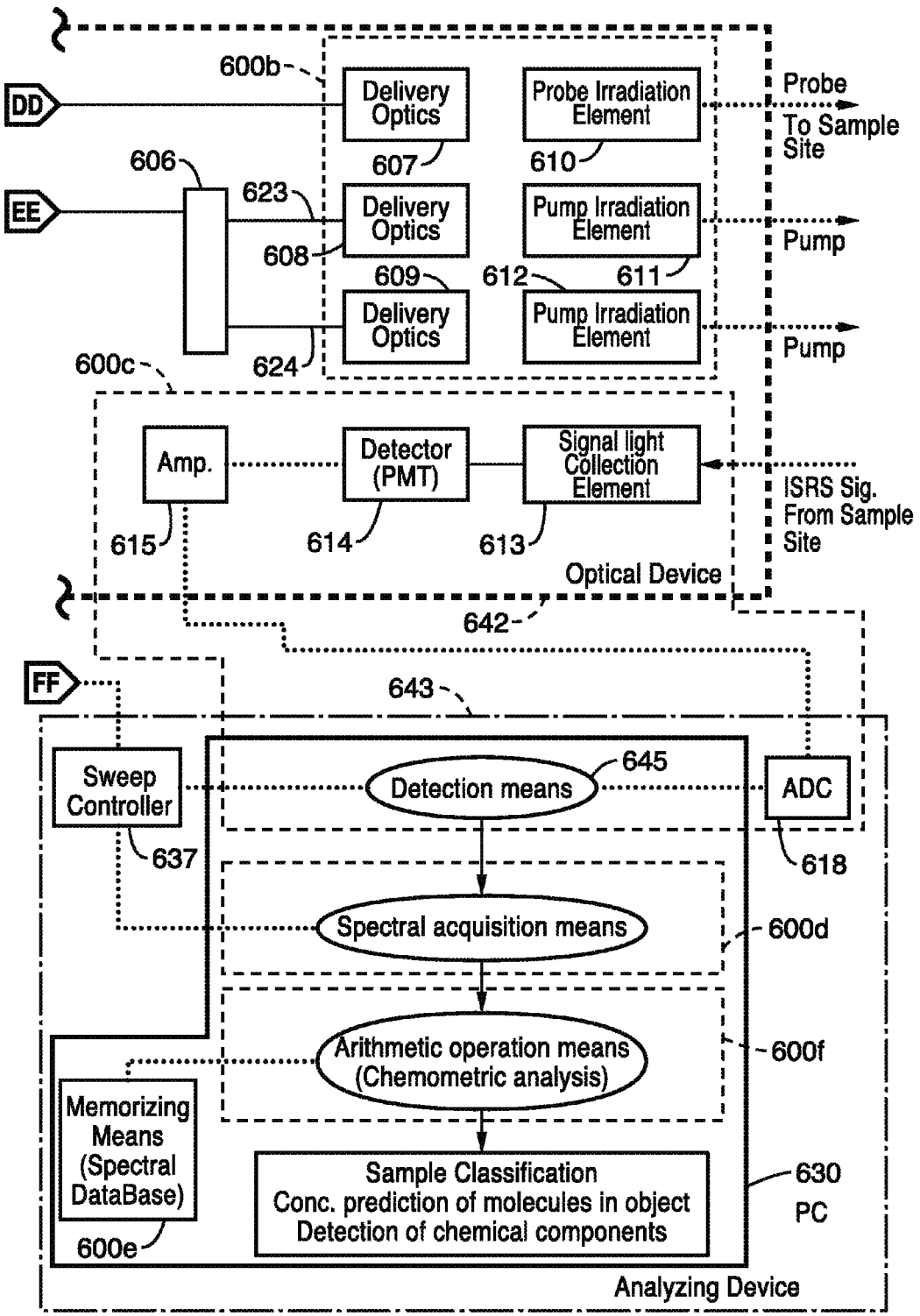

FIG. 5, FIG. 6A, and FIG. 6B illustrate an example embodiment 400 of the steps performed by a spectroscopic measurement apparatus 414 according to the present invention that measures a Raman spectrum of a sample 402 and analyzes the sample based on the acquired Raman spectrum of the sample. FIG. 6A and FIG. 6B schematically illustrate the configuration of an embodied apparatus. By way of example and not limitation, the following description assumes that the sample is a biological sample.

The apparatus is formed of an optical device 642 and an analyzing device 643 as shown in FIG. 6A and FIG. 6B. The optical device 642 can be the same as optical device 242 described in FIG. 2A and FIG. 2B above. The steps of the analyzing process include major blocks 600a through 600f as seen in FIG. 5, FIG. 6A and FIG. 6B, with steps 416, 418, 420, 422, 424, 426, 428, 430, 432 and 434 shown in FIG. 5. Accordingly, the apparatus as shown in FIG. 5, FIG. 6A and FIG. 6B, includes pump optical pulse train generating means 600a and irradiation means 600b, which can be the same as the pump optical pulse train generating means 200a and the irradiation means 200b described in relation to FIG. 2A and FIG. 2B. The optical device 642 as seen in FIG. 6A and FIG. 6B, can alternatively be replaced with a device corresponding to any of the variations of the optical device 242, as seen in FIG. 2A and FIG. 2B, which will be described later. The analyzing device 643 includes detection means 600c, spectrum acquisition means 600d, and arithmetic operation means 600f. The analyzing device further includes a sweep controller 637, which can be implemented in the same manner as sweep controller 237 described in regards to FIG. 2A and FIG. 2B. The detection means 600c and the spectrum acquisition means 600d, which can be the same as detection means 200c of FIG. 2A and FIG. 2B, and the spectrum acquisition means 200d described above, acquire the frequency spectrum of the vibrational coherence signal observed for each repetition rate of multiple optical pulses to produce a Raman spectrum of the sample, as described above.

The arithmetic operation means 600f preferably comprises a program executing from a memory on a computer 630 that performs chemometric analysis on the Raman spectrum of the sample. The chemometric analysis performed in the operating means is specifically spectral classification, spectral calibration, and spectral curve resolution, or any other suitable method contained in a typical chemometric analysis software package. According to the spectroscopic measurement apparatus of the present embodiment, a Raman spectrum of the sample is measured by carrying out the steps shown in FIG. 5, in particular 416, 418, 420, 422, 424, 426, 428, 430 and 432 which are categorized by the dotted lines into elements 600a-600f. The Raman spectrum is analyzed by the arithmetic operation means 600f in accordance with the flowchart of FIG. 5. The steps of FIG. 5 comprise 416 generating pump optical pulse trains, 418 guiding the pump optical pulse trains and the probe pulse to the irradiation elements, 420 irradiating of the object, 422 obtaining vibrational coherence spectrum at the arbitrary frequency of the pulse trains, 424 scanning the repetition rate of the pump optical pulse trains, 426 performing iterations of 416, 418, 420, 422 and 424, obtaining 428 Raman spectrum of the object from vibrational coherence data to arrive at Raman spectrum 430 which is analyzed in step 432 in response to spectral data 434 which is stored on molecules.

According to the method for analyzing a Raman spectrum of a biological sample performed in the arithmetic operation means 600f, the sample may be diagnosed by performing principle component analysis on a plurality of Raman spectra of the sample to produce a plot of scores of the principle component and classifying the spectra of the sample based on the distribution of the plot, or by performing cluster analysis on a plurality of Raman spectra of the sample and classifying the Raman spectra based on calculated spectral distances between Raman spectra of the sample.

Another method for analyzing a Raman spectrum of a biological sample by using the arithmetic operation means 600f involves memorizing Raman spectra of a plurality of different biological molecules in advance in memorizing means 600e. The memorizing means is a memory coupled to, or associated with (e.g., internal or external memory), computer 630. A Raman spectrum of each of the biological molecules reflects at least two types of vibrational mode information, the vibrational frequency information and the vibrational phase relaxation information obtained from the molecule, observed by the spectroscopic measurement apparatus of the invention. The Raman spectrum may further reflect information on the tensor components in third-order nonlinear susceptibility for each vibrational mode as well as the two types of vibrational mode information.

The Raman spectral data derived from the plurality of biological molecules and stored (e.g., memorized) in the memorizing means 600e are used to design a spectroscopic mode, also referred to as a calibration model or a training set used in the chemometric analysis, and spectral calibration such as based on Principle Component Regression (PCR) or Partial Least Square Fitting (PLS) is performed on a Raman spectrum of the sample to be measured. The concentration of any of the molecules in the biological sample can thus be predicted. In this case, the sample can be diagnosed for a molecule included in the thus designed spectroscopic model based on the predicted concentration of the molecule present in the sample. Alternatively, the Raman spectrum of the molecule whose concentration has been predicted by the spectral calibration is used to reproduce the Raman spectrum of the biological sample, and the difference spectrum between the observed Raman spectrum of the sample and the reproduced spectrum can be determined. The difference spectrum is an extracted Raman spectrum of a molecule or a group of molecules that is not included in the spectroscopic model. The specimen may be diagnosed based on the difference spectrum.

Referring to FIG. 6A and FIG. 6B, as similarly described in FIG. 2A and FIG. 2B, a single laser source 601 can be used, and is shown coupled to a splitter 602 from which optical paths 621 and 622 derive. Along optical path 621 is a variable optical delay 603, whose timing is controlled by timing control means 617, prior to reaching irradiation means 600b and delivery optics 607 and irradiation element 610. Along optical path 622 are a pump optical pulse train generation means 600a comprising a multiple optical pulse generator 604 controlled by rate control means 616 and dispersion compensator (DC) 605 shown for generating the optical pulse train (multiple optical pulses), the latter of which is disposed as required. Output from dispersion compensator 605 is split by a splitter 606 into paths 623 and 624. One optical path 623 is coupled to delivery optics 608 and irradiation element 611 of block 600b, while optical path 624 is coupled to delivery optics 609 and irradiation element 612 of block 200b. As can be seen, Irradiation means 200b is shown comprising sets of delivery optics 607, 608, 609 and irradiation elements 610, 611, and 612 for the optical probes and pump signals. The ISRS signal is collected by a signal light collection element 613 and detected by an optical detector 614, which can be amplified 615, converted to a digital signal, such as by using an analog-to-digital converter 618, whose output is detected within detection means 600c by a detector 645.

Another method for analyzing a Raman spectrum of a biological sample by using the arithmetic operation means 600f involves measuring a plurality of Raman spectra of the biological sample. Thereafter, self modeling curve resolution may be performed on the group of Raman spectra to calculate component spectra that form the Raman spectra. Further, comparing the components spectra with the Raman spectra derived from the biological molecules and memorized in the memorizing means 600e allows a molecule present in the biological sample to be identified.

The configuration of the multiple optical pulse generator 204 is not limited to the configuration described in regards to FIG. 2A and FIG. 2B above, but a variety of elements can be employed.

Figure 7A:
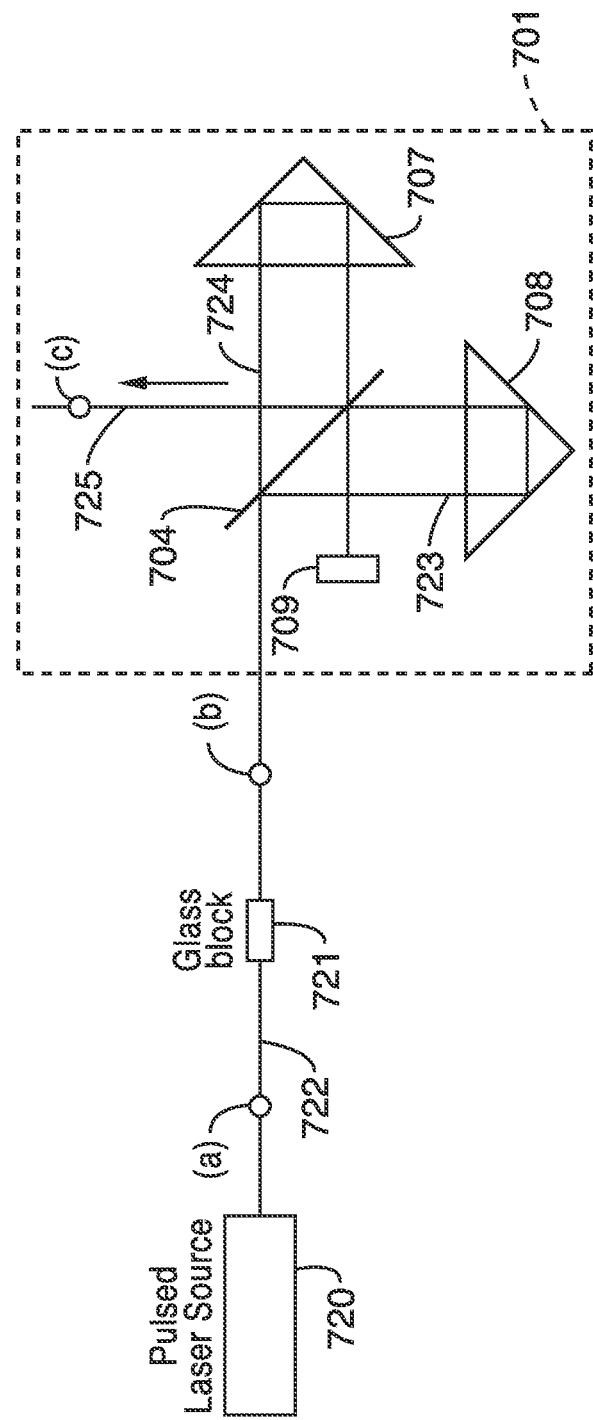
FIG. 7A is a schematic of a multiple optical pulse generator within the spectroscopic measurement apparatus according to an embodiment of the present invention.

FIG. 7A illustrates the configuration of an example generator in which the optical pulses undergo spectral amplitude modulation. The generator includes a laser source 720 generating signal 722 which is received by a frequency dispersion element 721 that imparts positive group velocity dispersion and an optical delay circuit disposed downstream of the laser source 720. By way of example and not limitation, the frequency dispersion element could comprise a glass block. The optical delay circuit 701, having reflectors 707, 708, and damper 709, is as described regarding the Michelson interferometer 301 described above. In the delay circuit a beam splitter 704 splits an optical pulse into two with optical pulses traveling along respective optical paths 723 and 724, and a relative delay time T is produced between the pulses and output on path 725.

Figure 7B:
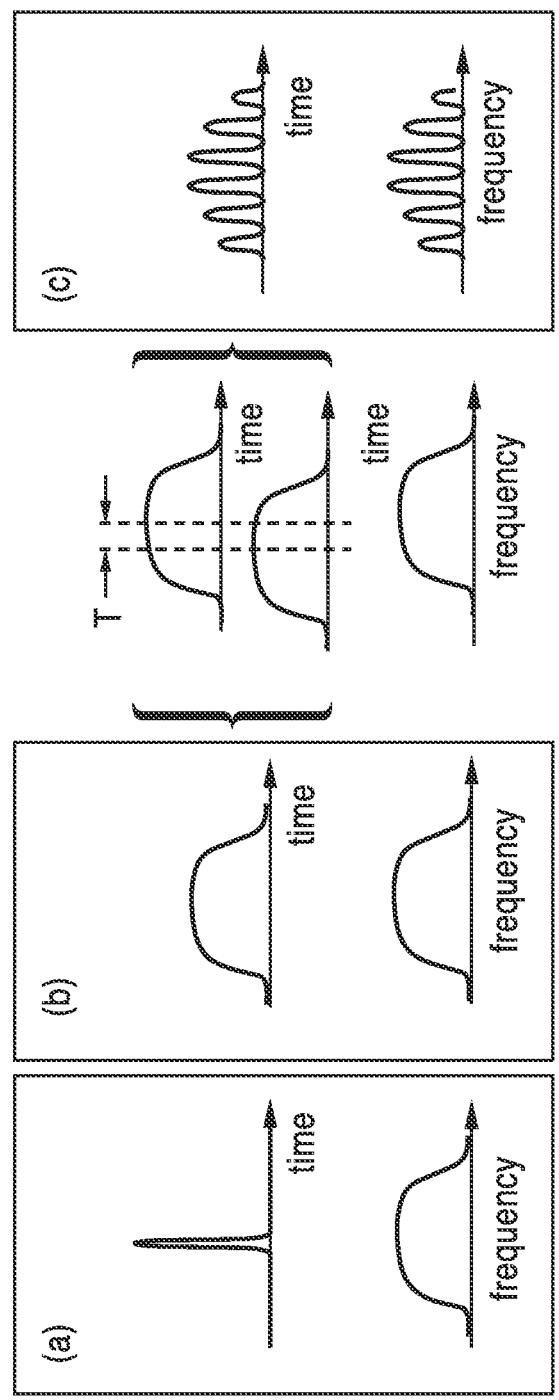
FIG. 7B are graphs depicting temporal profiles and frequency spectra of the optical pulse(s) in the generator of the spectroscopic measurement apparatus according to an embodiment of the present invention.

FIG. 7B depicts the spectra of the optical pulse(s) as well as the temporal profiles at points (a) and (b) on an optical path 722 and a point (c) on an optical path 725 with respect to FIG. 7A.

A TL pulse incident on the frequency dispersion element 721 is positively chirped by the element. The panel (b) of FIG. 7B shows the frequency spectrum and the temporal profile at the point (b). When the relative delay time T is produced between the split chirped pulses in the interferometer, the combined waveform at the point (c) forms a pulse train formed of optical pulses shown in the panel (c) of FIG. 7B. More specifically, the waveform representing the intensities of the optical pulses at the point (c) is determined by the following calculation: First, let τ be the temporal width of the chirped optical pulse at the point (b) and C be the chirp rate, and assume that the influence of dispersion between the point (b) and the point (c) is negligible. The temporal profile E1 representing the electric field of the optical pulses traveling one of the optical paths, the optical path 723, in the interferometer at the point (c) is expressed by the following equation:

$$E1 = E_0 \times \exp\left(-\left(\frac{t}{\tau}\right)^2\right) \times \exp(iCt^2) \times \exp(i\omega_0 t) + c.c$$

where $E_0$ represents the amplitude. The instantaneous waveform of each of the pulses has a Gaussian shape.

The waveform E2 representing the electric field of the optical pulses to which the relative delay time T has been imparted is as follows:

$$E2 = E_0 \times \exp\left(-\left(\frac{t-T}{\tau}\right)^2\right) \times \exp(iC(t-T)^2) \times \exp(i\omega_0(t-T)) + c.c$$

The waveform E representing the electric field of the optical pulses at the point (c) is expressed as follows:

$$E = E1 + E2 = E_0 \exp\left(-\left(\frac{t}{\tau}\right)^2\right) \times \exp\{i(Ct^2 + \omega_0 t)\} + E_0 \exp\left(-\left(\frac{t-T}{\tau}\right)^2\right) \times \exp\{i(C(t-T)^2 + \omega_0(t-T))\} + c.c$$

The waveform representing the intensity of the optical pulses at the point (c) is expressed as follows:

$$|E|^2 = (E1+E2) \times (E1+E2)^* = |E1|^2 + |E2|^2 + E2 \times E1^* + E1 \times E2^*$$

The third and fourth terms of the above equation are calculated as follows:

$$E2 \times E1^* + E1 \times E2^* = 2E_0^2 \exp\left(-\left(\frac{t}{\tau}\right)^2 - \left(\frac{t-T}{\tau}\right)^2\right) \times \cos(2CTt - CT^2 + \omega_0 T)$$

Therefore, the following equation is obtained:

$$|E|^2 = E_0^2 \left[ \begin{array}{l} \exp\left(-2\left(\frac{t}{\tau}\right)^2\right) + \exp\left(-2\left(\frac{t-T}{\tau}\right)^2\right) + \\ 2\exp\left(-\left(\frac{t}{\tau}\right)^2 - \left(\frac{t-T}{\tau}\right)^2\right) \times \cos(2CTt - CT^2 + \omega_0 T) \end{array} \right]$$

Since the temporal width τ of the optical pulse is much greater than the relative delay time T, the temporal profile representing the intensity of the optical pulses at the point (c) can be approximated by the following equation:

$$|E|^2 \approx 2E_0^2 \exp\left(-2\left(\frac{t}{\tau}\right)^2\right)\{1 + \cos(2CTt - CT^2 + \omega_0 T)\}$$

Therefore, the repetition rate of the optical pulse train at the point (c) is proportional to the product of the delay time T and the chirp rate C. Using the optical pulse train repetition rate control means 616 to adjust the relative delay time T produced in the optical delay circuit (interferometer) allows an optical pulse train having a desired repetition rate to be provided within the temporal width of the chirped pulse.

It should be appreciated that the number of optical pulses can be increased with the repetition rate remaining unchanged by increasing the amount of group velocity dispersion imparted in the frequency dispersion element 721 to expand the temporal profile of the pulse and reducing the relative delay time T.

According to this configuration of the multiple optical pulse generator, the temporal intervals between optical pulses can be readily and precisely changed only by changing the inter-pulse relative delay time T produced in the optical delay circuit (interferometer), whereby a high-resolution spectroscopic spectrum can be readily measured. Further, only a single interferometer is required to produce the delay time, whereby the configuration of the multiple optical pulse generator can be simplified.

Further, according to this configuration of the multiple optical pulse generator, supercontinuum (SC) light may be used as the pulse light to be incident on the generator. In this case, a picosecond or nanosecond laser may be used as laser source 720 and the output from the laser may be incident on a photonic crystal fiber (PCF) to produce SC light, which is then used as the incident pulse light. A generator capable of producing an optical pulse train having a high repetition rate can thus be configured at low cost.

Figure 7C:
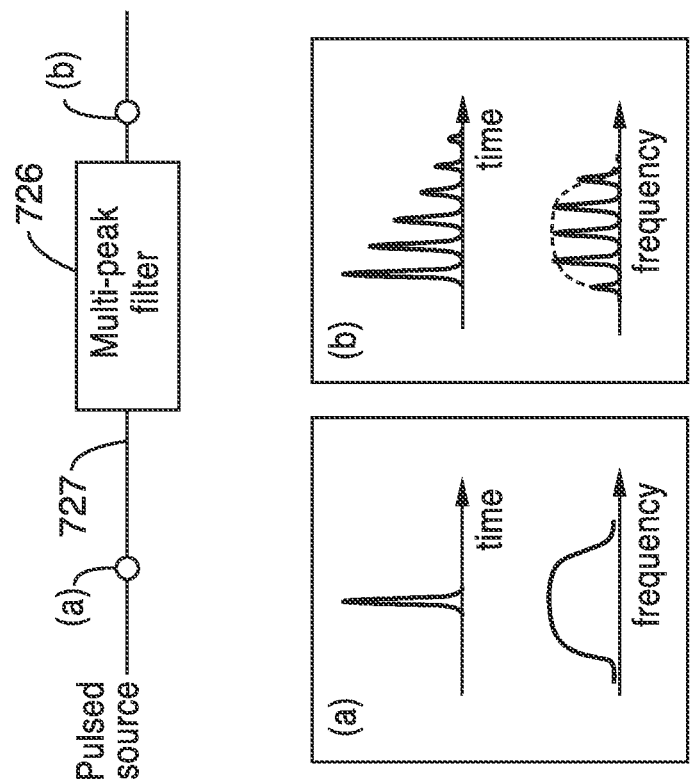
FIG. 7C is a schematic of a multiple optical pulse generator including a multi-peak filter and graphs of temporal profiles and frequency spectra of the optical pulse(s) in the generator according to an element of the present invention.

FIG. 7C illustrates another example configuration of the multiple optical pulse generator in which the optical pulses undergo spectral intensity modulation. The figure also depicts the spectra and temporal profiles of the optical pulse(s) at points (a) and (b) on an optical path 727 in the above configuration. In this configuration, a multi-peak filter 726 amplitude-modulates the spectrum of the incident optical pulse, and an optical pulse train (b) is produced along the temporal axis. The multi-peak filter may be a Fabry-Perot wavelength tunable filter or a fiber Bragg grating wavelength tunable filter.

Figure 7D:
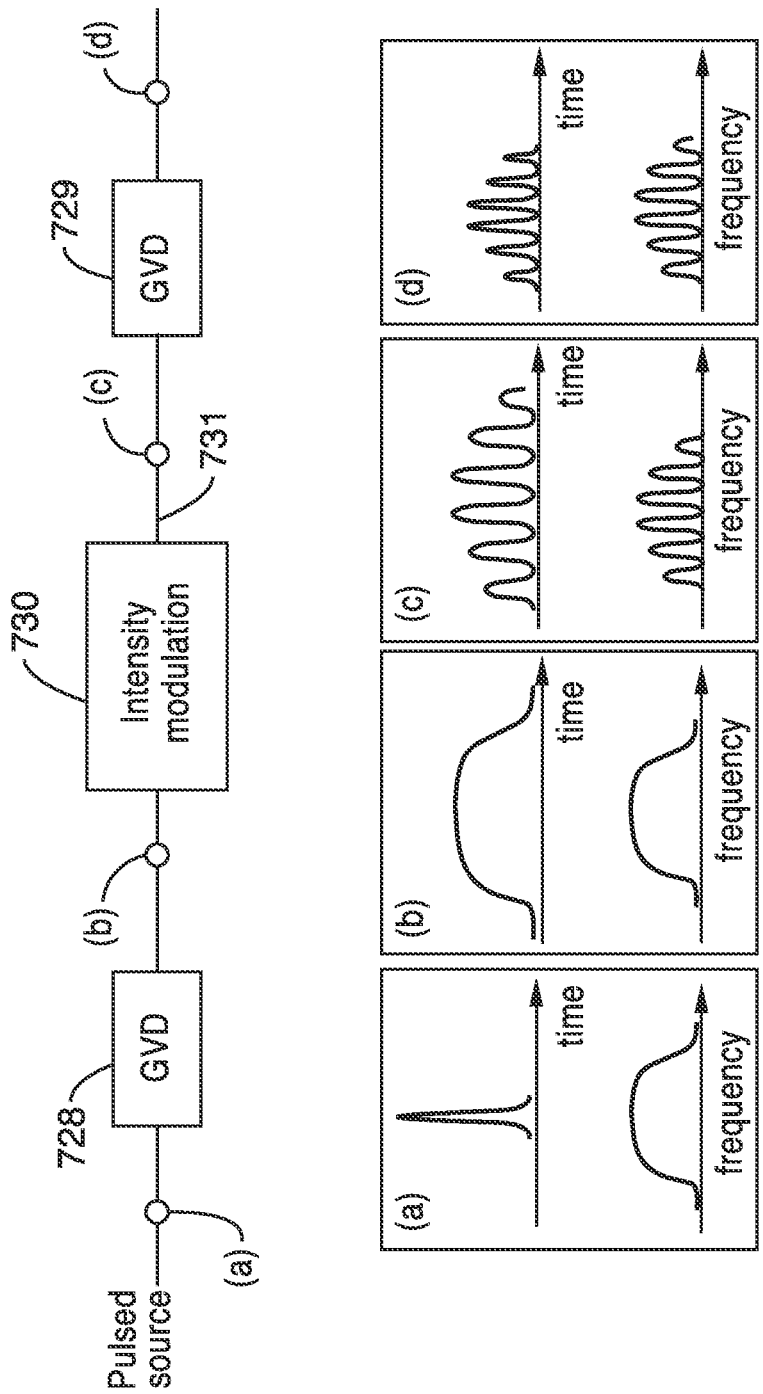
FIG. 7D is a schematic of a multiple optical pulse generator including an intensity modulation element using spectral intensity modulation to produce an optical pulse train, with graphs of temporal profiles and frequency spectra according to an embodiment of the present invention.

FIG. 7D shows another configuration of the multiple optical pulse generator in which the optical pulses undergo spectral intensity modulation. FIG. 7D also shows the spectra and temporal profiles of the optical pulse(s) at points (a), (b), (c), and (d) on an optical path 731 in the above configuration. The configuration is formed of a frequency dispersion element 728 that imparts group velocity dispersion to the output from a pulsed source, a frequency dispersion element 729 that imparts group velocity dispersion that is the reverse of the group velocity dispersion produced in the dispersion element 728, and an intensity modulation element 730 disposed between the two frequency dispersion elements. An optical pulse incident on the generator is chirped by a large amount due to the effect of the frequency dispersion element 728, whereby the temporal profile shown in the panel (b) of FIG. 7D is produced and the optical spectrum information is mapped along the temporal axis. Thereafter, the optical pulses (c) whose spectral amplitude has been temporally modulated by the intensity modulation element undergo temporal profile compression under the effect of frequency dispersion element 729, and the optical pulse train shown in panel (d) is produced.

Figure 7E:
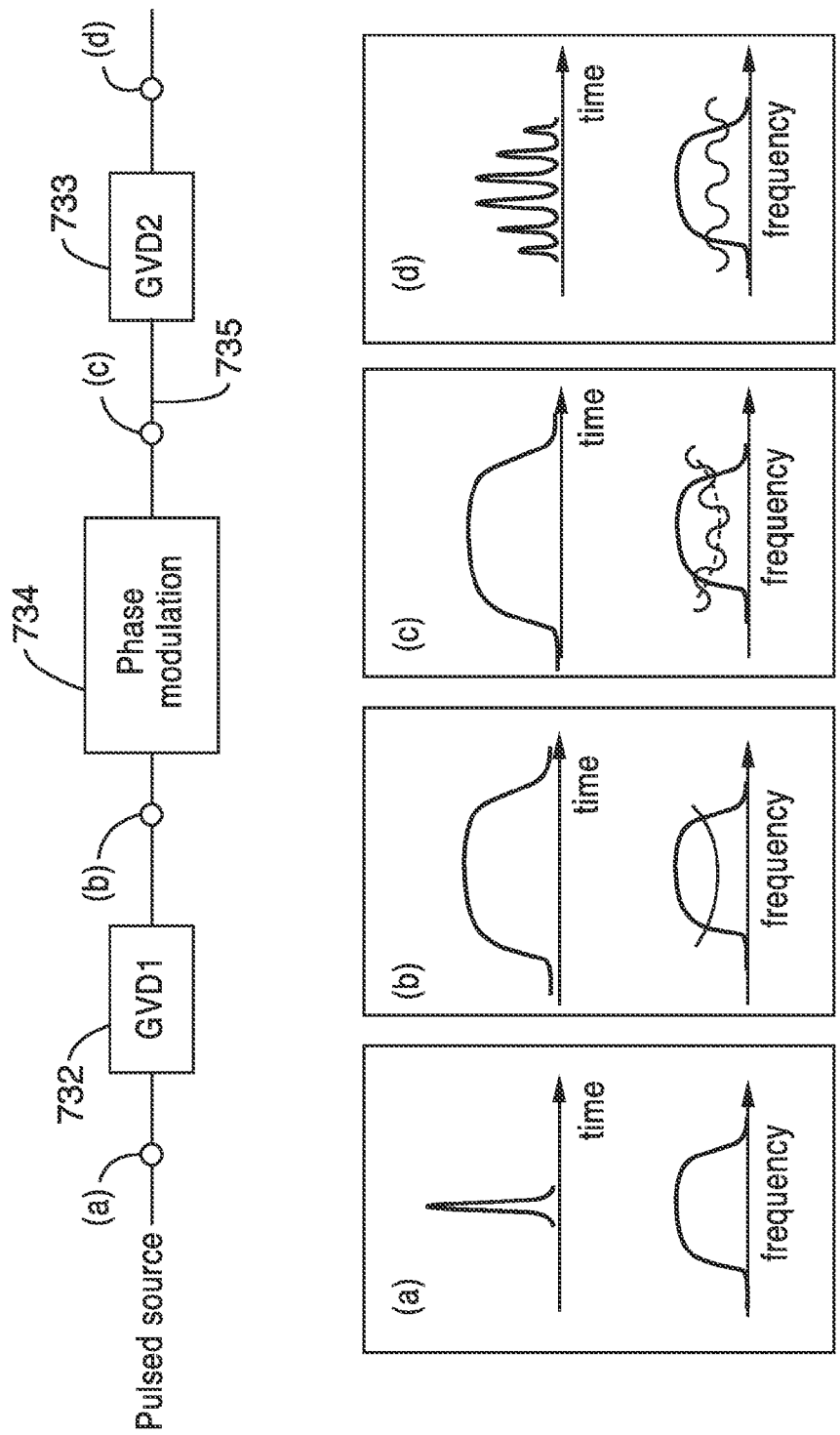
FIG. 7E is a schematic and graphs of a multiple optical pulse generator producing an optical pulse train according to an element of the present invention.

FIG. 7E illustrates an example configuration for a multiple optical pulse generator in which the optical pulses undergo spectral phase modulation. FIG. 7E also shows spectra and temporal profiles of the optical pulse(s) at points (a), (b), (c), and (d) on an optical path 735 in the above configuration. The configuration is formed of a frequency dispersion element 732 that imparts group velocity dispersion to the output from a pulsed source, a frequency dispersion element 733 that imparts group velocity dispersion that is the reverse of the group velocity dispersion produced in the dispersion element 732, and a phase modulation element 734 disposed between the two frequency dispersion elements. In the generator, group velocity dispersion is first imparted to incident pulse light to expand the temporal profile of the pulse by a large amount. That is, the optical pulse is chirped by a large amount, and the optical spectrum information is mapped along the temporal axis. The phase modulation element then temporally modulates the phase of the optical pulse. At the same time, the spectral phase of the light is also modulated. Thereafter, the chirped optical pulse having undergone the phase modulation passes through frequency dispersion element 733, where the temporal profile of the optical pulse is compressed. The operation described above allows the spectral phase of the optical pulse to be modulated periodically, whereby an optical pulse train can be provided along the temporal axis. The frequency at which the optical spectrum is modulated is determined by the amount of change in phase due to the group velocity dispersion and the cycle at which the phase modulation element modulated the phase.

Figure 7F:
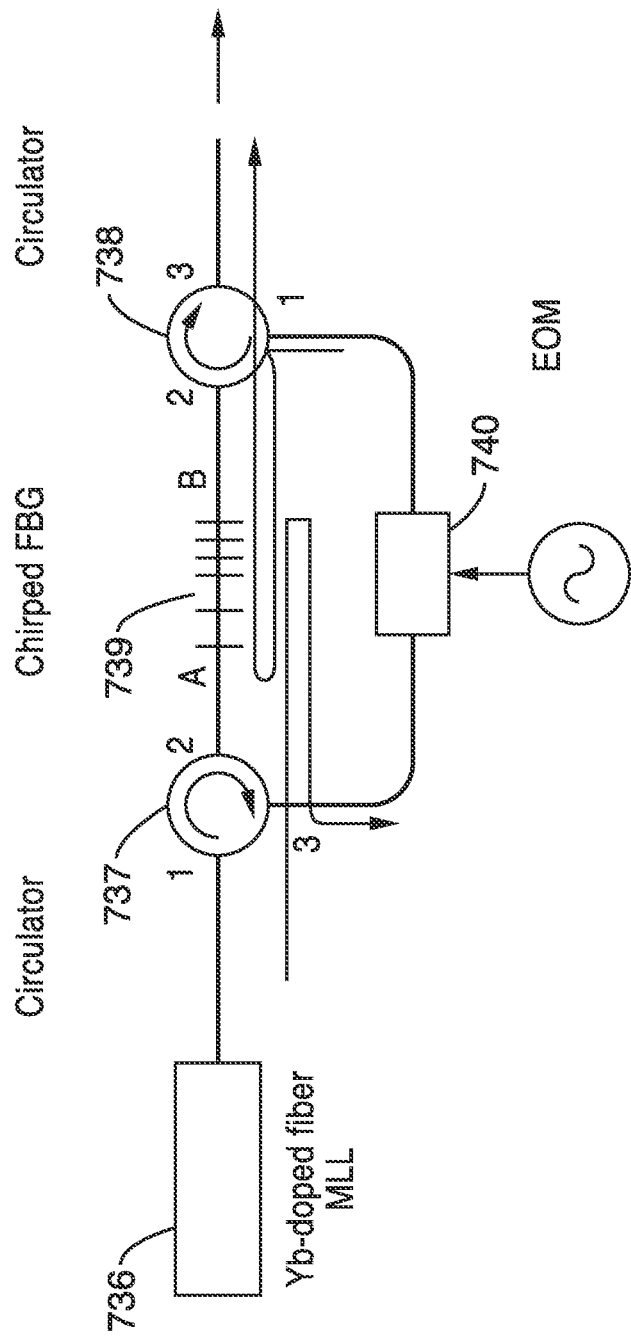
FIG. 7F is a schematic of a multiple optical pulse generator according to an element of the present invention.

FIG. 7F shows a specific configuration of a multiple optical pulse generator using spectral phase modulation. A Yb-doped Mode locked laser (MLL) 736 outputs a short pulse close to Fourier transform limit (TL), and the output light is inputted to a port 1 of a circulator 737. The light output through port 2 of circulator 737 is input to side A of a chirped FBG 739. The chirped FBG imparts a group velocity dispersion of +β2_FBG to the optical pulse. The optical pulses reflected off the chirped FBG are preferably substantially linearly chirped and have a sufficiently broadened temporal width. The light reflected off the chirped FBG is input to port 2 of the circulator 737 and output through a port 3 of the circulator 737. The light output through port 3 of circulator 737 is input to an Electro Optic Modulator (EOM) 740. The EOM performs phase modulation on the light input at a fixed cycle. The light pulse having undergone the phase modulation in the EOM is input to a port 1 of circulator 738. The light input to port 1 of circulator 738 is output through port 2 and input to a side B of chirped FBG 739. The chirped FBG imparts a GVD of −β2_FBG to the optical pulse. The optical pulses reflected off the chirped FBG form an optical pulse train with linear chirp compensated. The light reflected off the chirped FBG is input to port 2 of circulator 738 and output through port 3 of circulator 738.

Compared with the generator configured to use optical spectrum amplitude modulation, the present generator can produce an optical pulse train having a desired repetition rate with a small amount of loss. Further, the repetition rate of the optical pulse train can be precisely changed by changing the modulation cycle of the phase modulation element. Since no mechanically movable part is used, the failure rate can be reduced. Therefore, an optical spectrum can be advantageously acquired in a stable, easy, and precise manner.

The spectroscopic measurement apparatus according to the invention has been described with reference to the apparatus configuration, such as shown in FIG. 2A and FIG. 2B and elsewhere. In the apparatus configuration, the portion corresponding to the optical device 242 of FIG. 2A and FIG. 2B may be differently configured, as described. Other examples of the apparatus configuration will be described below. It is noted that in the following variations of the configuration of the spectroscopic measurement apparatus according to the invention, the portion corresponding to arithmetic and control device 243 has the same configuration and functions, and no redundant description thereof will be particularly made below. Further, the configuration of any of a variety of elements of the optical device, which will be described below, may be combined with analyzing device 643 to form an apparatus that measures a Raman spectrum of a sample and analyzes the spectrum. In addition, it will be appreciated that various combinations between the embodiments described herein would be obvious in view of the teachings of the present invention.

Figure 8:
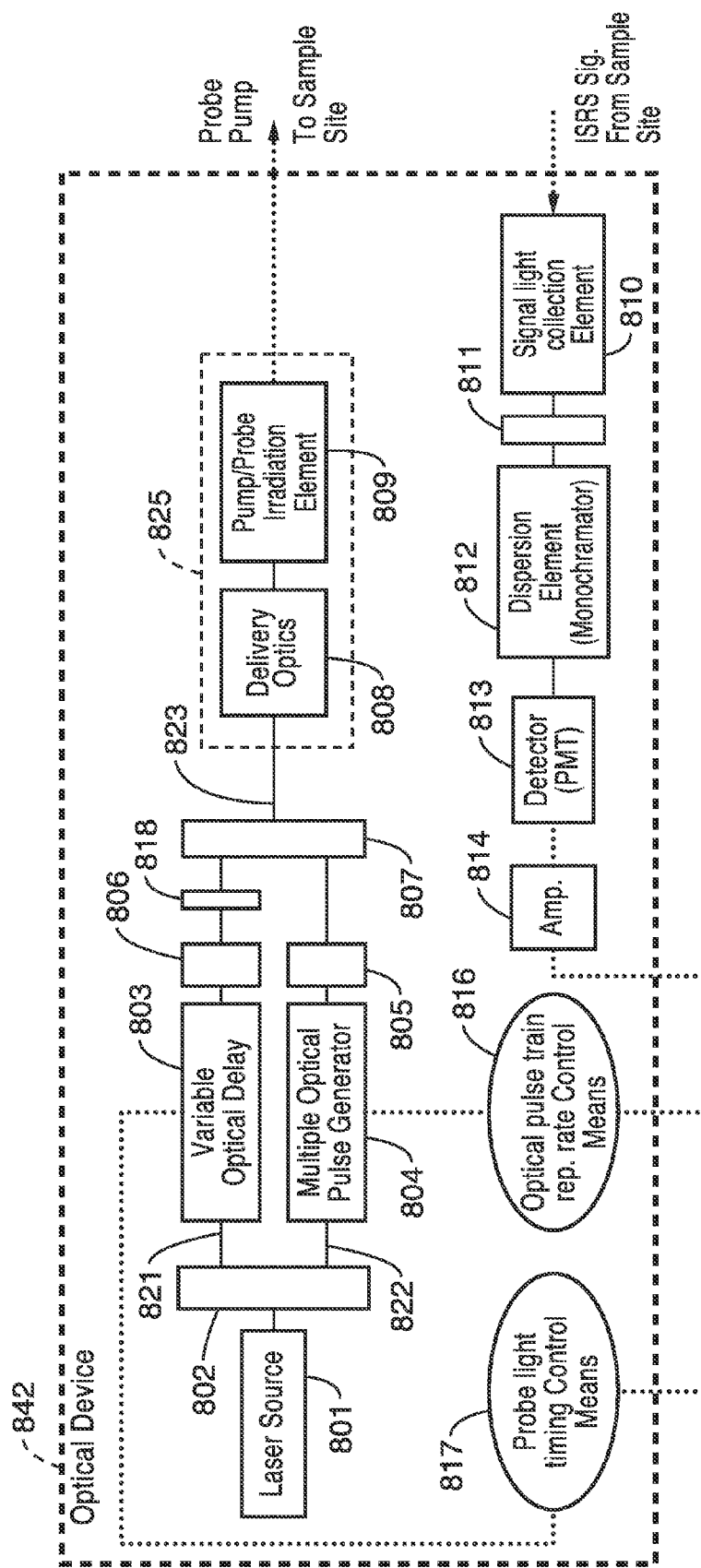
FIG. 8 is a schematic of an optical device in the spectroscopic measurement apparatus according to an element of the present invention.

FIG. 8 illustrates another example element of an optical device 842 according to the present invention. A single laser source 801 can be used, and is shown coupled to a splitter 802 from which arise optical paths 821 and 822. Along optical path 821 is a variable optical delay 803, whose timing is controlled by timing control means 817. Along optical path 822 are a pump optical pulse train generation means comprising a multiple optical pulse generator 804 controlled by rate control means 816 and dispersion compensator (DC) 805 In this configuration of optical device 842, a wavelength conversion element 806 and an optical filter 818 are disposed in an optical path 821, where the wavelength of the probe light is converted into a wavelength shorter than the wavelength of the multiple optical pulses (excitation pulse light) and the fundamental component is optically removed. Examples of wavelength conversion element 806 include a Raman shifter, a nonlinear optical crystal, or similar optical elements or combinations known in the art. The probe light traveling along optical path 821 is combined with the multiple optical pulses traveling along an optical path 822 in a combiner 807, and the combined light travels along a common optical path 823. Irradiation means 825 formed of delivery optics 808 and an irradiation element 809 irradiates a sample with the probe light and the multiple optical pulses in a substantially coaxial manner.

In a desirable optical arrangement, a signal light collection element 810 is disposed on the opposite side of the sample to irradiation element 809 and collects the probe light passing through the sample. In an alternative arrangement, signal light collection element 810 can be disposed on the side of the sample where the irradiation element is disposed and the probe light reflected off or scattered by the sample is collected. The probe light and the excitation pulse light collected by signal light collection element 810 pass through an optical filter (high-pass filter) 811, where only the excitation pulse light is removed. The probe light then undergoes wavelength dispersion in a monochromator 812, and the dispersed light is detected by an optical detector 813 disposed at an exit slit of the monochromator. The optical detector 813 may be a photomultiplier, a photodiode, or a CCD detector, which is shown being amplified at amplifier 814.

The frequency of the probe light is shifted in accordance with the change in the refractive index of the sample in the impulsive stimulated Raman scattering process, and the temporal profile representing the frequency shift is modulated at the beat frequency of the vibrational coherence signal. Therefore, the vibrational coherence signal of the sample can be obtained by causing the signal light to undergo wavelength dispersion in the monochromator 812 and observing the temporal profile of the probe light intensity at a specific wavelength. A Raman spectrum of the sample can be acquired by using multiple optical pulse train repetition rate adjustment means 816 to sweep the repetition rate of the multiple optical pulse train and calculating the frequency spectrum of the vibrational coherence signal observed for each repetition rate.

Since the optical device 842 of the present embodiment allows the sample to be irradiated with the probe light and the multiple optical pulses in a substantially coaxial manner, the irradiation means 825 can be simplified. Further, filter 811 can provide for removing the excitation light having passed through the sample or having been scattered by the sample. In addition to this, since the wavelength of the probe light is shorter than that of the excitation light, any fluorescence from the sample produced when the sample is irradiated with the excitation light will not affect the probe light. A satisfactory Raman spectrum with reduced effect of the background light can thus be acquired.

Figure 9:
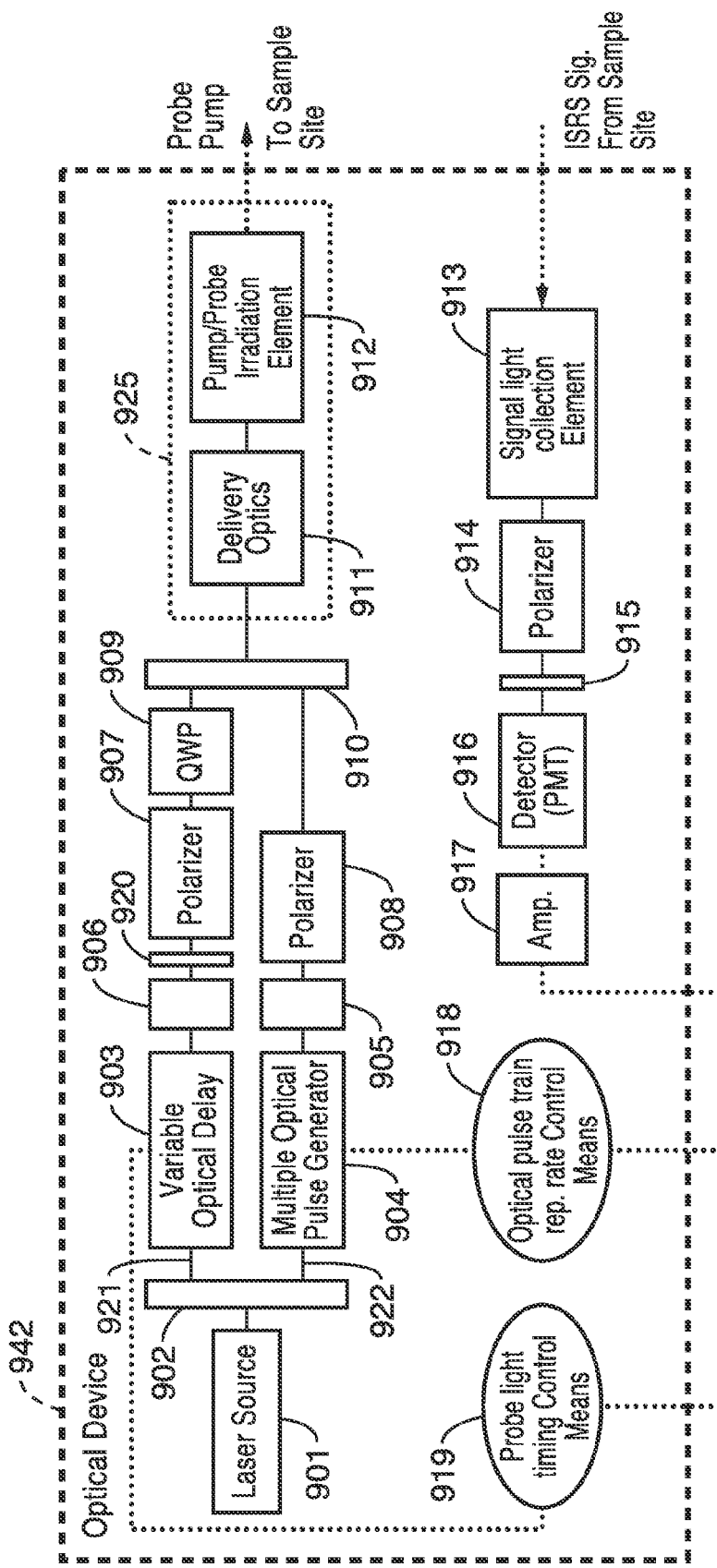
FIG. 9 is a schematic of an optical device in the spectroscopic measurement according to an element of the present invention.

FIG. 9 illustrates an example embodiment of optical device 942 in the spectroscopic measurement apparatus of the invention. Again it will be seen that output is from a single laser source 901 which is split by a splitter 902 onto optical paths 921 and 922. Output along one path, represented as path 921 is subject to a variable optical delay 903, such as control by a probe light timing control means 919. Along the path 922 is seen the MOPG 904 followed by a dispersion compensator 905. In the configuration of an optical device 942, a wavelength conversion element 906 and an optical filter 920 are disposed in an optical path 921, where the wavelength of the probe light is converted into a wavelength shorter than the wavelength of the multiple optical pulses (excitation light) and the fundamental component is optically removed. Examples of the wavelength conversion element 906 may be a Raman shifter and a nonlinear optical crystal. Polarizers 907 and 908 are disposed in the optical paths 921 and 922, and set in such a way that the polarized probe light is inclined to the polarized multiple optical pulses by 45 degrees. A quarter wave plate 909 is disposed downstream of the polarizer 907 with the transmission axis of the quarter wave plate 909 slightly inclined to the polarization direction of the probe light so that the linearly polarized probe light is converted into a slightly elliptically polarized light. The probe light is combined with the multiple optical pulses in a combiner 910, and irradiation means 925 formed of delivery optics 911 and an irradiation element 912 irradiates a sample with the combined probe light and multiple optical pulses in a substantially coaxial manner.

In a desirable optical arrangement, a signal light collection element 913 is disposed on the opposite side of the sample to irradiation element 912 and collects probe light passing through the sample. In an alternative arrangement, signal light collection element 913 can be disposed on the side of the sample where the irradiation element is disposed and the probe light reflected off or scattered by the sample is collected. The probe light and the excitation light (multiple optical pulses) collected by signal light collection element 913 pass through an optical filter (high-pass filter) 915, where only the excitation pulse light is removed.

A polarizer 914 is disposed upstream of the optical filter 915. The polarizer 914 is disposed in such a way that the transmission axis thereof is inclined to the polarization direction of the multiple optical pulses by 45 degrees away from the polarization direction of the probe light. In other words, the transmission axis is perpendicular to the polarized probe light. Therefore, when the sample is not irradiated with the excitation light, part of the elliptically polarized probe light produced by the quarter wave plate 909, that is, only the component passing though the polarizer 914, is detected by an optical detector 916, which is preferably followed by an amplifier 917.

When the multiple optical pulses excite the sample so that impulsive stimulated Raman scattering occurs, refractive index anisotropy is induced in the sample, and the polarized probe light is rotated. This process newly produces a probe light component that passes through polarizer 914. Since the refractive index anisotropy of the sample is modulated at the beat frequency of the vibrational coherence signal, the vibrational coherence signal of the sample is obtained by using optical detector 916 to detect the temporal profile of the probe light passing through polarizer 914. A Raman spectrum of the sample can be acquired by using multiple optical pulse train repetition rate control means 918 to sweep the repetition rate of the multiple optical pulses and calculating the frequency spectrum of the vibrational coherence signal for each repetition rate.

Since the optical device 942 of the present embodiment can irradiate the sample with the probe light and the multiple optical pulses in a substantially coaxial manner, the delivery optics and the optics in the irradiation element can be simplified. Further, the optical filter 915 can remove the excitation light having passed through the sample or having been scattered by the sample. In addition to this, since the wavelength of the probe light is shorter than that of the excitation light, any fluorescence from the sample produced when the sample is irradiated with the excitation light will not affect the probe light. A satisfactory Raman spectrum with reduced effect of the background light can thus be acquired.

Further, in the present embodiment, optical heterodyne detection in which the component of the probe light that passes through polarizer 914 is used as local oscillator allows a vibrational coherence signal linearly proportional to third-order nonlinear susceptibility to be obtained. In this case, since the Raman spectrum intensity is proportional to the molecular concentration, the heterodyne detection enables more sensitive measurement than that based on homodyne detection in applications in which a relatively low-concentration molecule contained in a biological sample is observed.

Further, a positive or negative Raman band is observed in the frequency spectrum in accordance with the magnitude of the depolarization ratio of a vibrational mode, more specifically, depending on whether the depolarization ratio of the mode is greater or smaller than 0.33. It is therefore possible to observe not only vibrational mode information including the frequency and the vibrational phase relaxation time of a molecule but also Raman spectrum information reflecting the depolarization ratio of the vibrational mode, which is further advantageous in extracting band information that characterizes the structure of a molecule or a group of molecules from a structureless Raman spectrum.

Figure 10A:
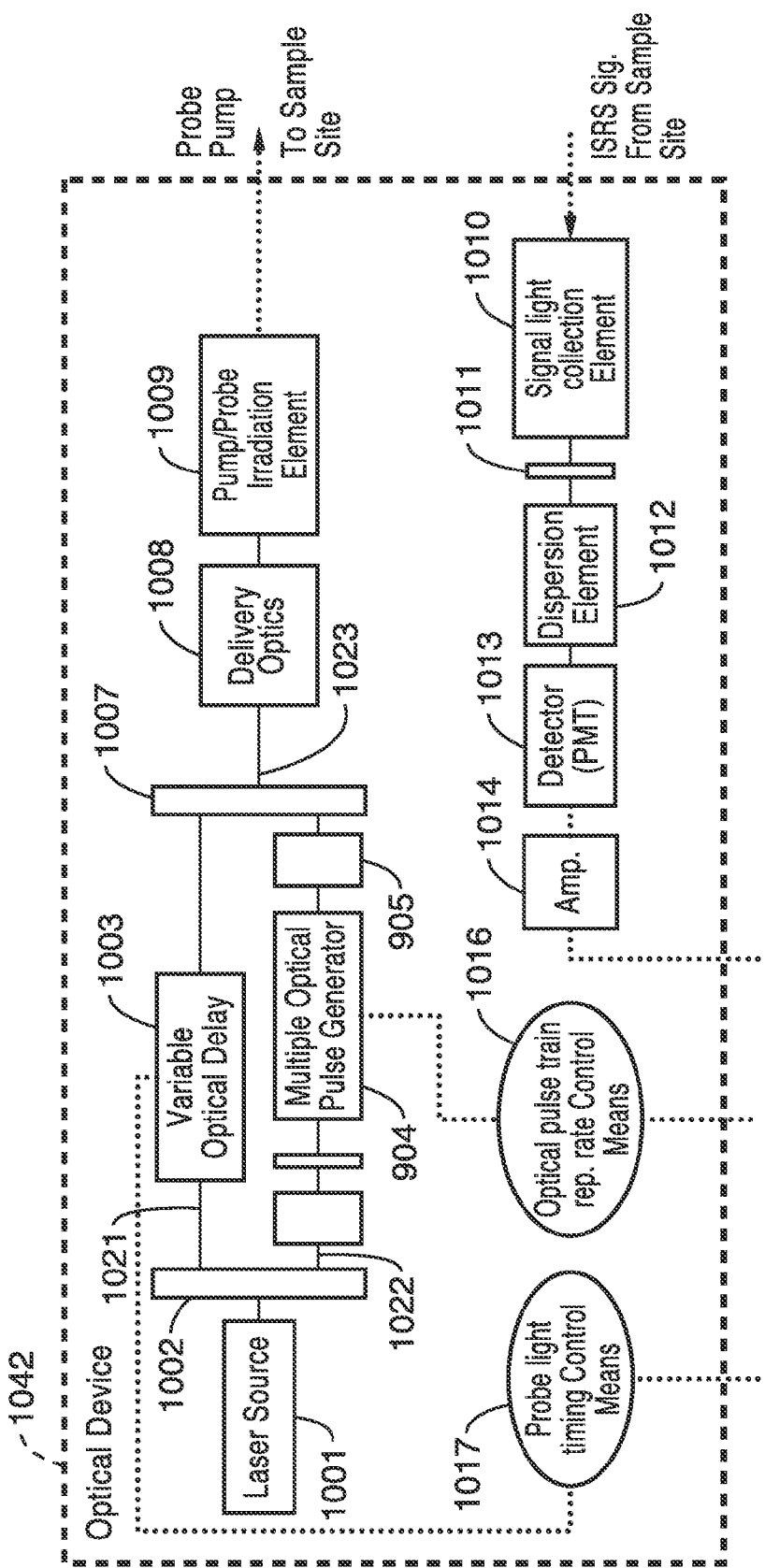
FIG. 10A is a schematic of an optical device in the spectroscopic measurement apparatus according to an element of the present invention.

FIG. 10A shows the configuration of another element of the optical device 242 as was earlier described in FIG. 2A and FIG. 2B in the spectroscopic measurement apparatus of the invention. An optical device 1042 of the present embodiment has a form similar to those of optical devices 842 and 942, each of which irradiates the sample with the multiple optical pulses and the probe light in a substantially coaxial manner, but is characterized in that a nonlinear optical crystal 1006 is disposed in an optical path 1022 in which the multiple optical pulse generator is disposed.

In a manner as previously described a laser source 1001 is shown being split by a splitter 1002 onto optical paths 1021 and 1022. Output along one path, represented as path 1021 is subject to a variable optical delay 1003 controlled in response to a probe light timing control means 1017, such as control by a probe light timing control means 1019. Along the path 1022 is seen a non-linear optical crystal 1006, filter 1015, multiple optical pulse generator (MOPG) 1004 controlled by an optical pulse train repetition rate control means 1016, and a dispersion compensator 1005. Paths 1021 and 1022 are combined at combiner 1007 to produce signal 1023 received within delivery optics 1008 and pump/probe irradiation elements 1009. In the present embodiment, for example, the nonlinear optical crystal 1006 produces a second harmonic or third harmonic wave of the fundamental wave from a laser source 1001 (titanium-sapphire laser), and multiple optical pulses (excitation light) are produced from the harmonic wave. On the other hand, the fundamental wave from the titanium-sapphire laser is used as the probe light.

Figure 10D:
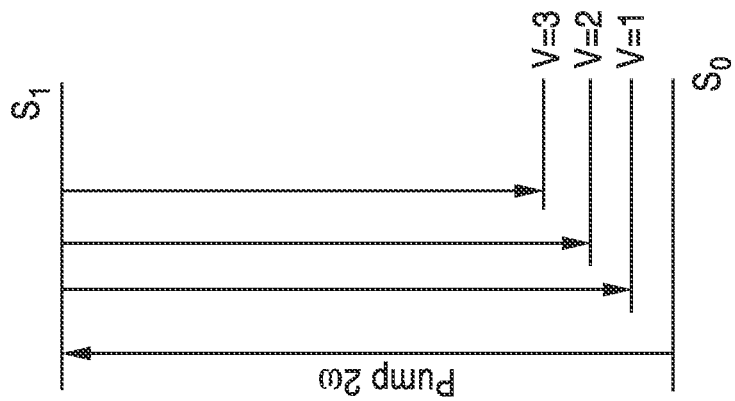
FIG. 10B through FIG. 10D are graphs of stimulated Raman scattering and vibrational states according to the embodiment of the present invention shown in FIG. 10A.
Figure 10C:
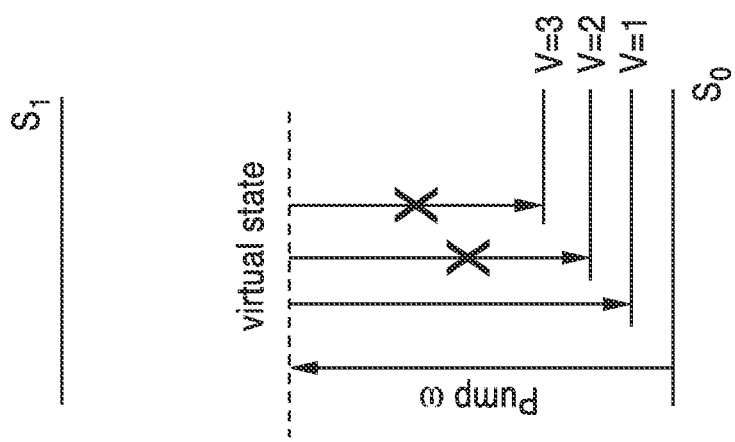
Figure 10B:
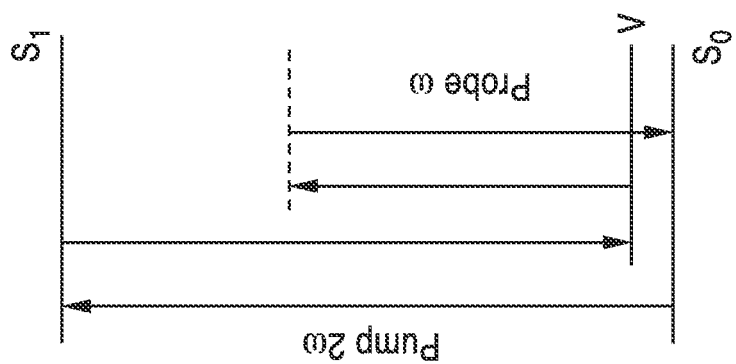

FIG. 10B depicts that according to the present embodiment, when the energy of the excitation light resonate with an electronic excited state (S1 excited state, for example) of a molecule in the sample, the stimulated Raman scattering process shown in the energy diagram of the figure is used to observe a vibrational coherence signal of the molecule. Further, the probe light and the excitation light collected by a signal light collection element 1010 pass through a long-pass filter 1011, where only the excitation light is removed, followed by dispersion element 1012, detector 1013 and amplifier 1014.

The transition probability R in a Raman scattering process is expressed by the Kramers-Heisenberg-Dirac (KHD) dispersion formula. According to the formula, the transition probability R in the following two Raman scattering processes, (1) a Raman scattering process involving no electronic excited state of the molecule and (2) a Raman scattering process involving an electronic excited state of the molecule, for example, the S1 state, is proportional to the following values:

Raman transition probability provided when no electronic excited state is involved $$R \propto \langle v'|Q|v''\rangle^2 \quad (1)$$

Raman transition probability provided when an electronic excited state is involved $$R \propto \left(\sum_V \langle v'|v\rangle\langle v|v''\rangle\right)^2 \quad (2)$$

where Q represents the coordinates of the atomic nucleus in a certain vibrational mode; v″ represents the initial vibrational state; v′ represents the final vibrational state; and v represents an intermediate vibrational state in the Raman transition.

FIG. 10C depicts that according to Eq. (1), an acceptable process is only that process in which the difference in the number of vibrational quanta between the initial state v″ and the final state v′ in the Raman scattering process is +1, is as shown in the figure. On the other hand, Eq. (2) depicts a factor representing the degree of overlap of vibrational wave functions (e.g., such as using a Frank Condon product), and the factor is in general not zero in a harmonic tone transition or an overtone transition.

FIG. 10D depicts that the impulsive stimulated Raman scattering involving an electronic excited state excites not only has the fundamental mode but also higher-order vibrational modes present in the energy band of the excitation pulse light, as shown in the figure.

Figure 10E:
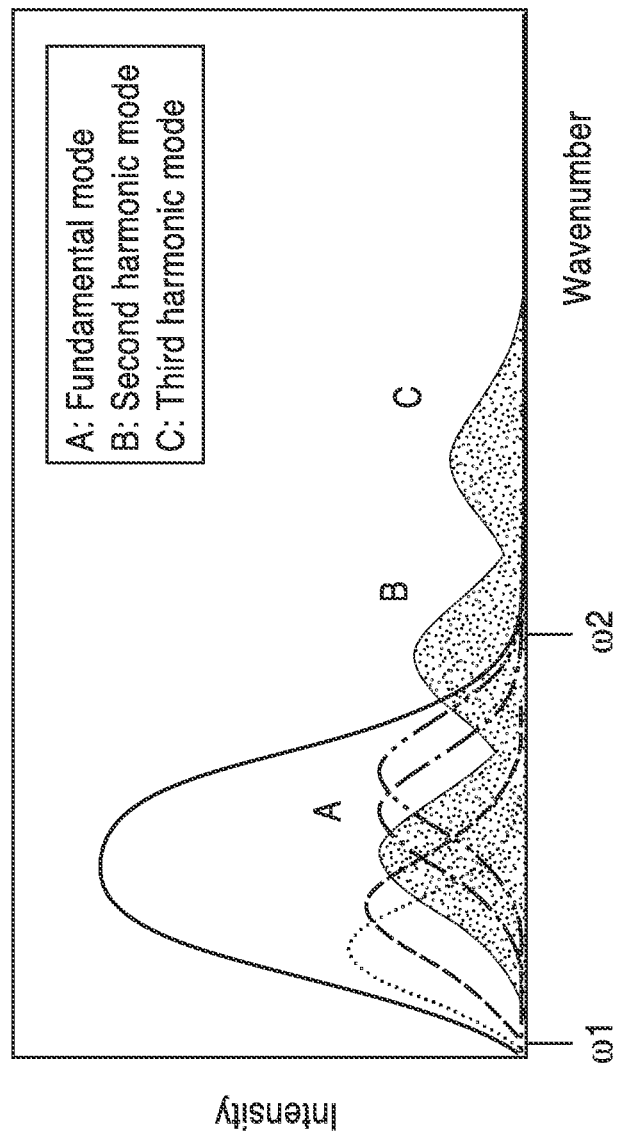
FIG. 10E is a graph of Raman spectrum for a mixed sample containing a plurality of different molecules generated according to the embodiment of the present invention shown in FIG. 10A.

FIG. 10E depicts an advantageous effect provided when a mixed sample is observed through impulse stimulated Raman scattering involving the electronic excited states described above. In FIG. 10E, the dotted line, the broken line, the dashed line, the double-dashed line, and the shaded band labeled with the character A represent fundamental mode bands derived from different types of molecules. The shaded bands labeled with the characters B and C represent the second harmonic mode and the third harmonic mode of the band A, respectively. Raman transition involving no electronic excited state is first described. When the repetition rate of the multiple optical pulses is swept from ω1 to ω2, and the vibrational phase relaxation time for each mode is shorter than the duration of the multiple optical pulses or the vibrational phase relaxation time does not differ from each other among the modes, the spectrum indicated by the solid line, in which all the bands are superimposed, is observed. In this case, molecular information that provides the band A is lost in the spectrum indicated by the solid line. Raman transition involving an electronic excited state is next described. It is now assumed that the carrier frequency of the multiple optical pulses resonates only with the electronic excited state of the molecule responsible for the shaded bands. In this case, when repetition rate of the multiple optical pulses is swept from ω1 to ω2, not only the spectrum indicated by the solid line but also the bands B and C, which are the overtones of the shaded band A, are observed. Since the frequencies of the bands B and C greatly differ from the repetition rate of the multiple optical pulses, the bands B and C do not overlap with the bands derived from the other molecules in the spectrum.

Therefore, according to the present embodiment, irradiating a biological sample with multiple optical pulses that resonate with the energy of an electronic excited state of a specific molecule contained in the biological sample advantageously allows information only on a Raman spectrum of the molecule to be extracted and observed.

In the present embodiment, when the multiple optical pulses are produced from the second harmonic of the titanium-sapphire laser light, the central wavelength of the second harmonic wave ranges from 390 to 430 nm. In this case, a Raman spectrum of a protein containing heme, flavin adenine dinucleotide (FAD), or other cofactors can be selectively observed from a biological sample. When the third harmonic of the titanium-sapphire laser light is used, the central wavelength thereof ranges from 260 to 285 nm. In this case, Raman spectra of deoxyribonucleic acid and ribonucleic acid can be selectively observed from a biological sample.

Figure 11A:
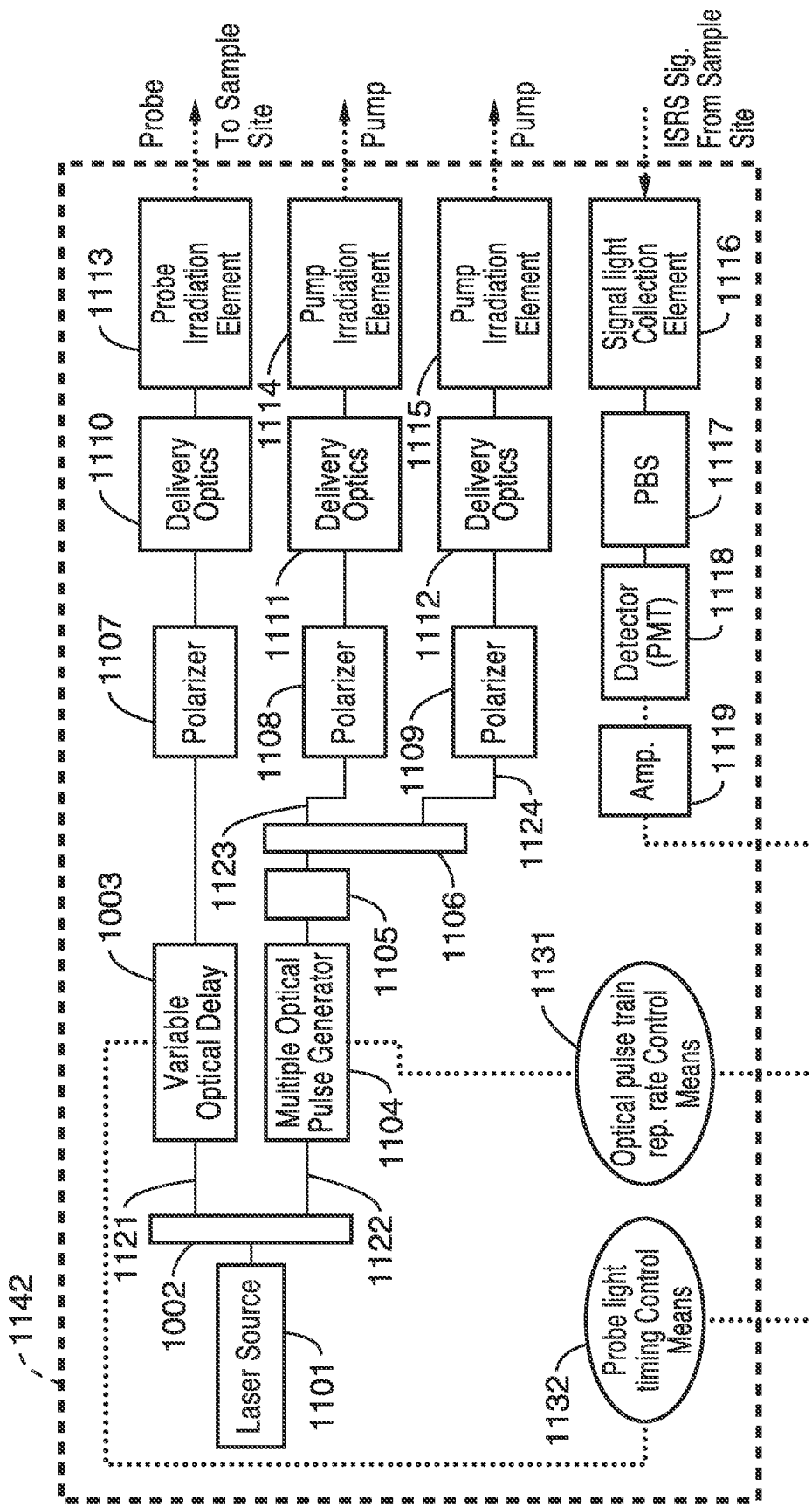
FIG. 11A and FIG. 11B are schematics of alternative optical devices in the spectroscopic measurement apparatus according to elements of the present invention.
Figure 11B:
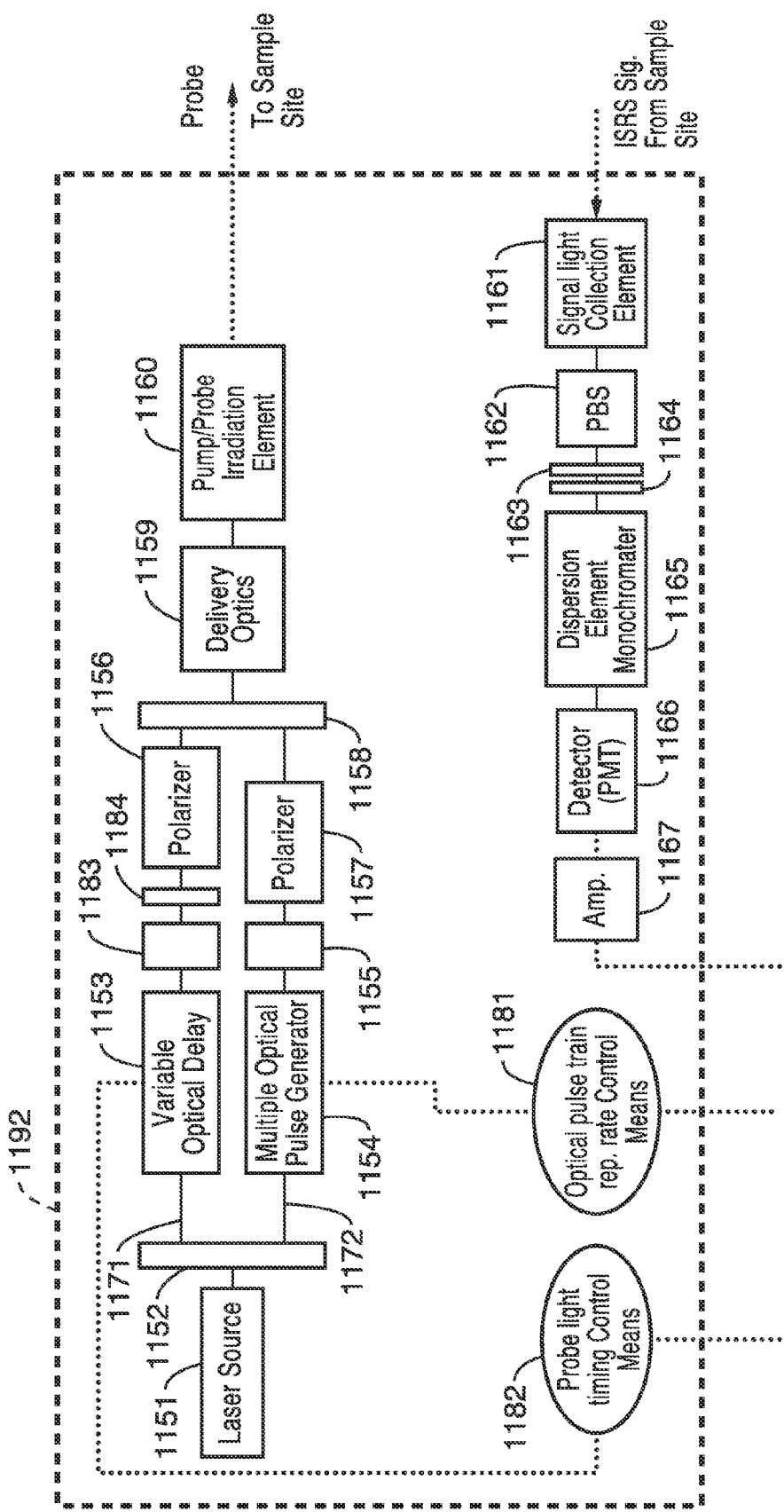

FIG. 11A and FIG. 11B illustrate another example embodiment of optical device 242 described earlier in relation to FIG. 2A and FIG. 2B, in the spectroscopic measurement apparatus of the invention. In the present embodiment, the configuration of an optical device 1142 that irradiates a sample with the multiple optical pulses and the probe light that intersect each other is employed, or the configuration of an optical device 1192 that irradiates a sample with the multiple optical pulses and the probe light in a substantially coaxial manner. The configuration of the optical device 1142 is first described.

As with the other embodiments, only a single laser source 1101 is required and its output is directed to splitter 1102 from which optical paths 1121 and 1122 proceed. Along one of the paths, path 1121, is a variable optical delay 1103 controlled by control means 1132. Along the second path is a multiple optical pulse generator 1104 controlled by rate control mechanism 1131, followed by a dispersion compensator 1105. The configuration is based on that of the optical device 242 but differs therefrom in that polarizers 1107, 1108, and 1109 are disposed in an optical path 1121 and optical paths 1123 and 1124 created by splitting an optical path 1122 by a separator 1106 so that the probe light and the multiple optical pulses can be polarized in desired directions. Following the polarizers are the sets of delivery optics 1110, 1111, 1112 along with irradiation elements 1113, 1114, and 1115. A polarization element 1117 is further disposed downstream of a signal light collection element 1116. The polarization element 1117 can comprise a Rochon prism, a Wollaston prism, or any other suitable polarization beam splitter. After the diffracted probe light, which is spatially separated from the multiple optical pulses, is collected by the signal light collection element 1116, the diffracted probe light passes the polarization element, where two pulse light whose polarization directions are perpendicular to each other are produced. The pulse light are detected by an optical detector 1118, before being amplified by amplifier 1119.

By contrast to the above, the configuration of the optical device 1192 in FIG. 11B is based on that of the optical device 842 shown in FIG. 8 but differs therefrom in that polarizers 1156 and 1157 are disposed in optical paths 1171 and 1172 in such a way that the probe light and the multiple optical pulses can be polarized in desired directions. Further, a polarization element 1162 is disposed downstream of a signal light collection element 1161, and depolarizers 1163, 1164 are disposed upstream of a monochromator 1165. The polarization element 1162 is a Rochon prism, a Wollaston prism, or any other suitable polarization beam splitter, and splits the diffracted probe light into two pulse light fluxes whose polarization directions are perpendicular to each other. Following the monochromator are a detector 1166 and amplifier 1167.

Optical device 1192 is shown with a similar single laser source 1151 output to splitter 1152 from which optical paths 1171 and 1172 proceed. Along one of the paths, path 1171, is a variable optical delay 1153 controlled by control means 1182, and followed by a wave length conversion element 1183 and an optical filter 1184 prior to a polarizer 1156. Along the second path is a multiple optical pulse generator 1154 controlled by rate control mechanism 1181, followed by a dispersion compensator 1155. Optical paths 1156 and 1157 are combined by combiner 1158 before reaching delivery optics 1159 and irradiation element 1160.

Figure 11C:
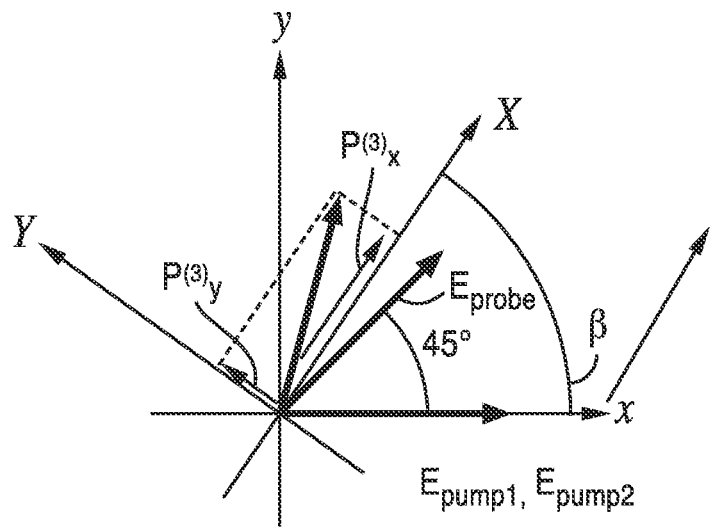
FIG. 11C is a graph of angular relationships among polarized multiple optical pulses (excitation light), polarized probe light, and third-order nonlinear polarization according to the element of the present invention shown in FIG. 11A and FIG. 11B.

FIG. 11C shows the relationship among the polarization directions of the multiple optical pulses and the probe light, the two orthogonal optical axes X and Y of a polarization beam splitter used as the polarization element 1162, and the orientation of third-order nonlinear polarization $P^{(3)}$ induced by the light irradiation in the optical device 1142 or 1192. In FIG. 11C, Epump1 and Epump2 represent the direction of the polarization of the multiple optical pulses, that is, the polarized excitation light, and are parallel to the x-axis direction. Eprobe represents the direction of the polarization of the probe light. The direction of the polarization of the excitation light and the direction of the polarization of the probe light are set in such a way that they are inclined to each other by 45 degrees. One of the optical axes of the polarization beam splitter, the optical axis X, is inclined to the direction of the polarization of the excitation light by a variable angle $\beta$.

Now, let $\chi^{(3)R}_{1111}$ and $\chi^{(3)R}_{2211}$ be the tensor components of the third-order nonlinear susceptibility of a vibrational mode R, and $P^{(3)x}$, $P^{(3)y}$, $P^{(3)X}$, and $P^{(3)Y}$ be third-order nonlinear polarization produced in the x direction, the y direction, the X direction, and the Y direction shown in FIG. 11C, respectively. The following relationship is established:

$$P^{(3)}_x = 1/\sqrt{2}\chi^{(3)R}_{1111} \times E_{pump1} E_{pump2} {}^* E_{probe}$$

$$P^{(3)}_y = 1/\sqrt{2}\chi^{(3)R}_{2112} \times E_{pump1} E_{pump2} {}^* E_{probe}$$

$$P^{(3)}_X = (1/\sqrt{2}\chi^{(3)R}_{1111} \cos\beta + 1/\sqrt{2}\chi^{(3)R}_{2112} \sin\beta) \times E_{pump1} E_{pump2} {}^* E_{probe}$$

$$P^{(3)}_Y = (-1/\sqrt{2}\chi^{(3)R}_{1111} \sin\beta + 1/\sqrt{2}\chi^{(3)R}_{2112} \cos\beta) \times E_{pump1} E_{pump2} {}^* E_{probe}$$

When the sample is isotropic, the following relationship is established by introducing a depolarization ratio $\rho^R$ of the vibrational mode R:

$$\chi^{(3)R}_{1111} = \chi^{(3)R}_{1122} + \chi^{(3)R}_{1212} + \chi^{(3)R}_{1221}, \chi^{(3)}_{1221}{}^R = \chi^{(3)R}_{2112}$$

$$\chi^{(3)R}_{2112} = (1 - 2\rho^R)\chi^{(3)R}_{1111}$$

Therefore, the X-direction component of the third-order nonlinear polarization is expressed as follows:

$$P^{(3)}_x = \sqrt{\frac{(\chi^{(3)R}_{1111})^2 + (\chi^{(3)R}_{2112})^2}{2}} \sin\left(\beta + \arctan\left(\frac{1}{1 - 2\rho^R}\right)\right) \quad (*)$$

Therefore, when part of the probe light having exited from the polarization beam splitter and having polarization directions perpendicular to each other, that is, the component parallel to the X-axis direction shown in FIG. 11C, is observed, the signal intensity under observation is proportional to the square of the third-order nonlinear polarization $P_X^{(3)}(*)$, which is the term described above, and dependent on the tensor component $\chi^{(3)R}_{1111}$ of the third-order nonlinear susceptibility, the depolarization ratio $\rho^R$ of the vibrational mode, and the angle of rotation $\beta$ of the optical axis of the polarization beam splitter.

Figure 11D:
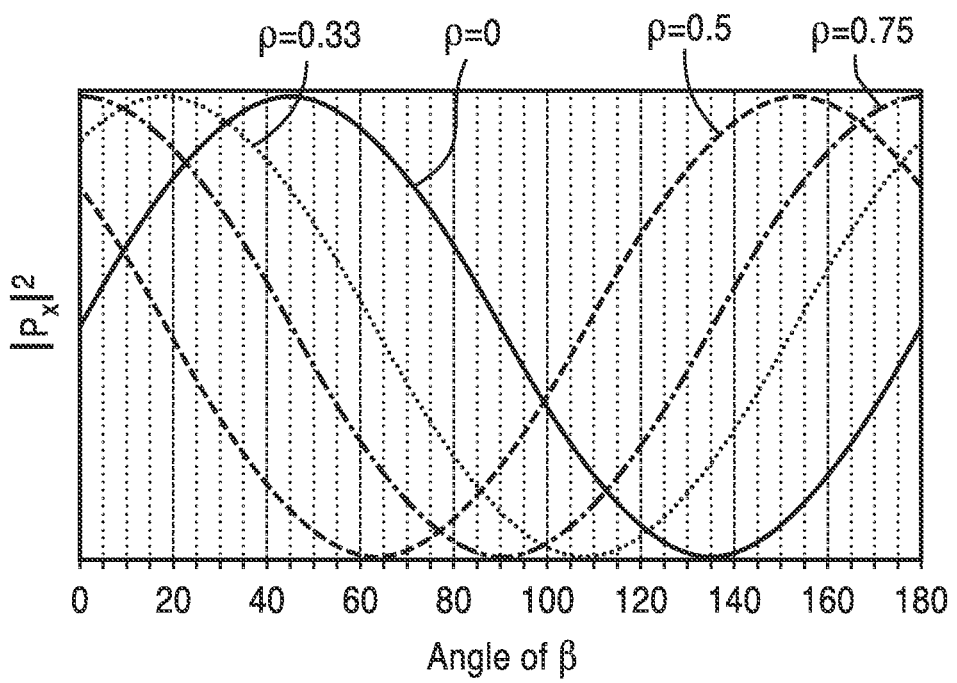
FIG. 11D is a graph of vibrational band intensity in response to polarizer rotation angle according to the element of the present invention shown in FIG. 11A and FIG. 11B.

FIG. 11D depicts curves plotted of the observed signal light intensity versus the angle of rotation $\beta$ for several depolarization ratios of the vibrational mode. The amplitude of each of the curves is proportional to the tensor component $\chi^{(3)R}_{1111}$ of the third-order nonlinear susceptibility in each mode, but normalized in FIG. 11D. The relationship between the signal intensity and the angle of rotation $\beta$ shows that the signal resulted from depolarized Raman mode can be eliminated by setting the angle of rotation $\beta$ at a value close to 90 degrees, and the signal resulted from totally polarized Raman mode can be eliminated by setting the angle of rotation $\beta$ at a value close to 135 degrees. As described above, appropriately configuring the polarization element 1117 or 1162 allows the contribution of a mode having a specific depolarization ratio to be minimized in the Raman spectrum.

Further, the signal component derived from an instantaneous response of electrons can be removed when the third-order nonlinear polarization is induced in the molecule, by setting the angle of rotation $\beta$ at 108 degrees. In this way, only the vibrational coherence signal derived from the atomic nucleus can be detected, and a Raman spectrum of the sample can be precisely measured.

As described above, the optical device 1142 or 1192 of the present embodiment allows observation of not only mode information including the frequency and the vibrational phase relaxation time of a molecule but also Raman spectrum information reflecting the information on the third-order nonlinear susceptibility tensor components in the vibrational mode, which is further advantageous in extracting band information that characterizes the structure of a molecule or a group of molecules from a structureless Raman spectrum.

Figure 12A:
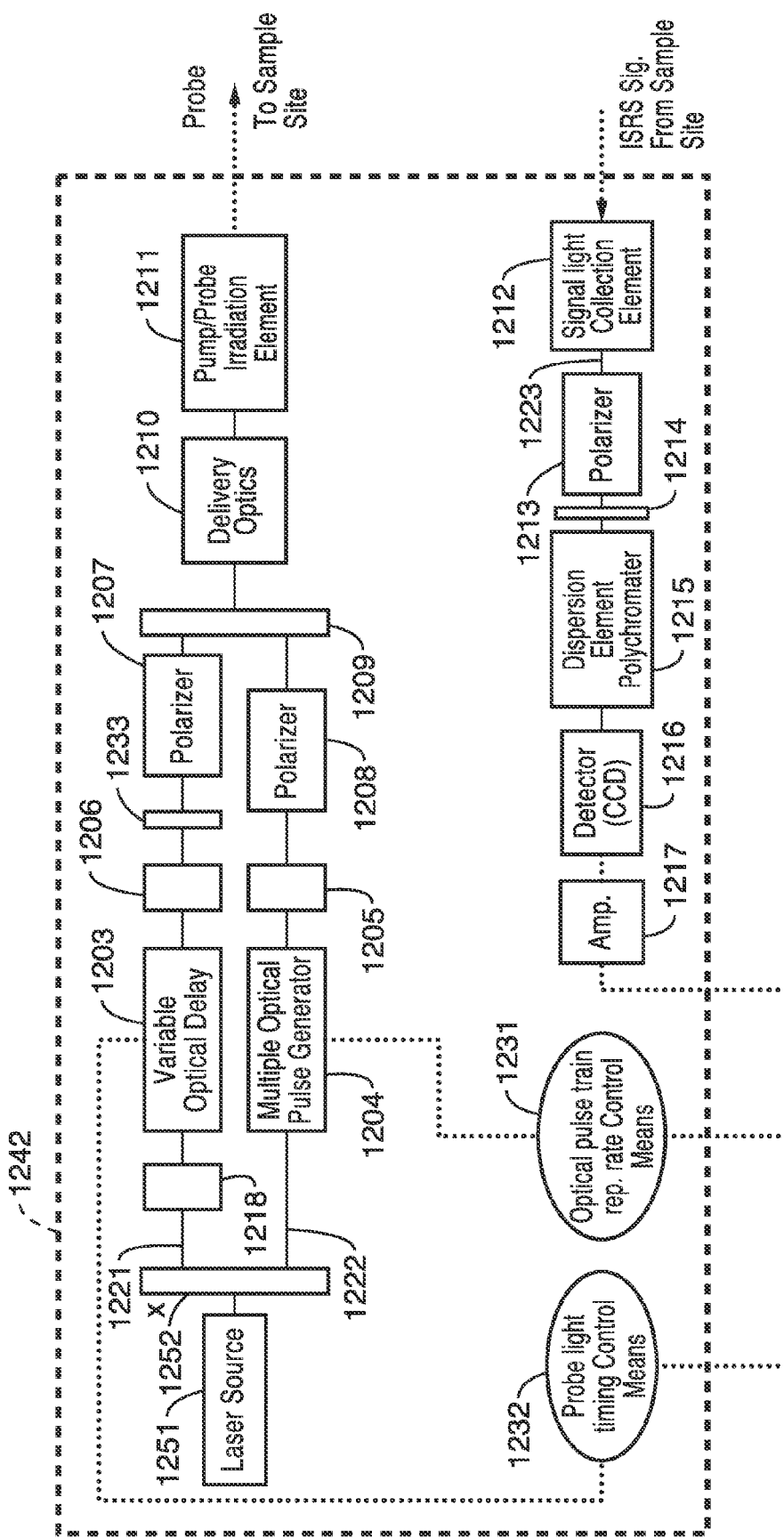
FIG. 12A and FIG. 12B are schematics of alternate embodiments of optical devices in the spectroscopic measurement apparatus according to elements of the present invention.
Figure 12B:
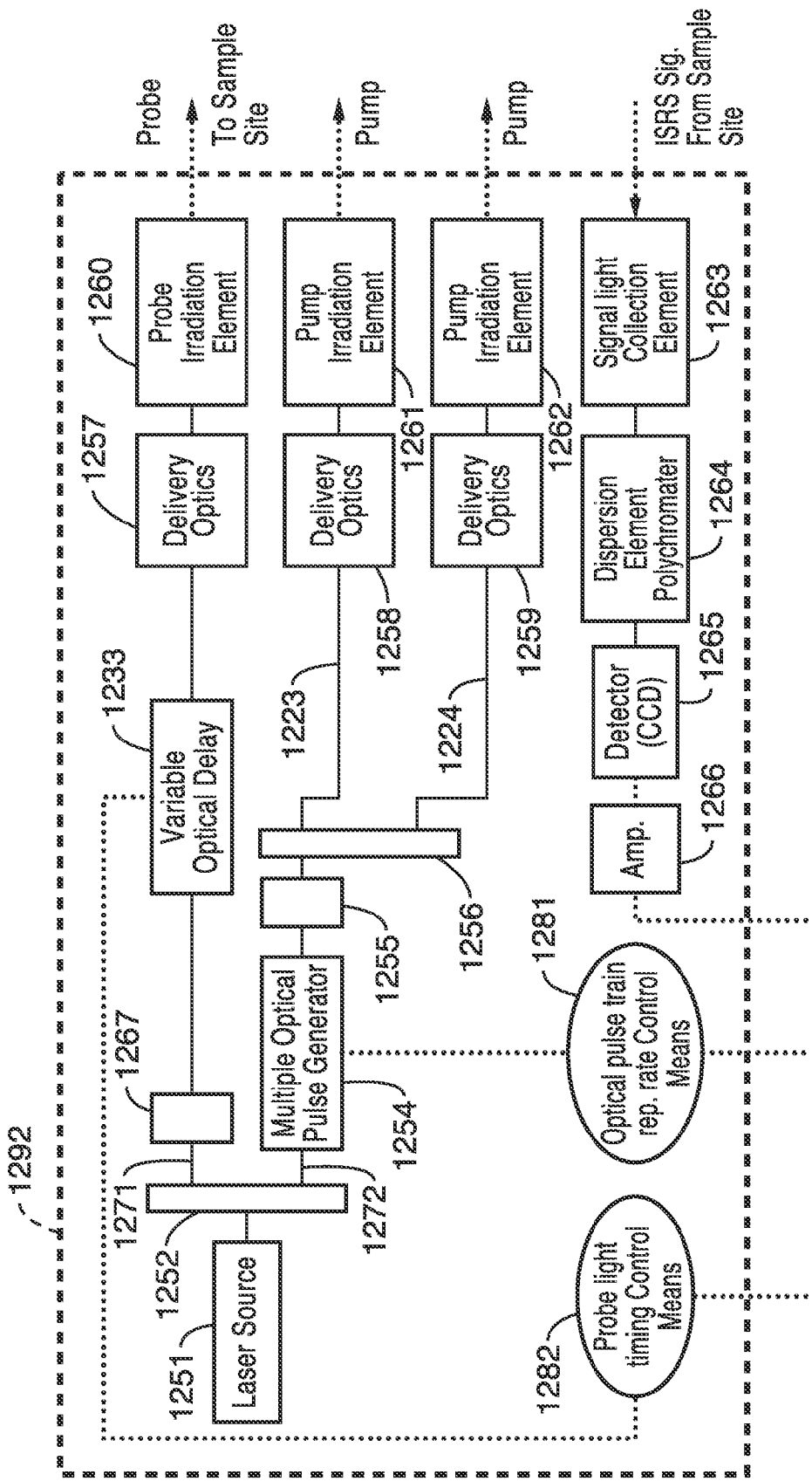

FIG. 12A illustrates an example embodiment of an optical device 1242 based on the configuration of the optical device 942 previously shown that irradiates a sample with the multiple optical pulses (excitation light) and the probe light in a coaxial manner. In contrast to this embodiment, the configuration of an optical device 1292 shown in FIG. 12B is based on the configuration of the optical device 242 previously shown that irradiates a sample with the excitation light and the probe light in a non-coaxial manner. As with the other embodiments, only a single laser source 1251 is required and its output is directed to splitter 1252 from which optical paths 1221 and 1222 proceed in FIG. 12A and paths 1271 and 1272 in FIG. 12B. In FIG. 12A along path 1221 is a narrow-band filter 1218 and a variable optical delay 1203 controlled by control means 1232, followed by a wavelength conversion element 1206, an optical filter 1233 and polarizer 1207. Along the second path in FIG. 12A is a multiple optical pulse generator 1204 controlled by rate control mechanism 1231, followed by a dispersion compensator 1205 and polarizer 1208. The two paths 1221 and 1222 are combined at combiner 1209 and directed through delivery optics 1210 and irradiation element 1211. In FIG. 12B along path 1271 is a narrow-band filter 1267 and a variable optical delay 1253 controlled by control means 1282, followed by delivery optics 1257 and irradiation element 1260 for the probe. Along the second path in FIG. 12B is a multiple optical pulse generator 1254 controlled by rate control mechanism 1281, followed by a dispersion compensator 1255 and another splitter 1256 generating two paths 1223 and 1224 directed through delivery optics 1258, 1259 and irradiation elements 1261 and 1262 respectively.

The ISRS signal in FIG. 12A is collected at collection element 1212 into signal 1223, passed through a polarizer 1213, and through an optical filter 1214, into dispersion element 1215, detector 1216 and amplifier 1217. The ISRS signal in FIG. 12B is collected at collection element 1263 into dispersion element 1264, detector 1265 and amplified in amplifier 1266.

In the above configurations, narrow-band filters 1218 and 1267 are disposed in optical paths 1221 and 1271, respectively, along which the probe light travels. In this way, narrow line width probe light can be produced from femtosecond pulse light. The temporal width of the pulsed probe light may be any value that is longer than the duration of the pulse train formed of the multiple optical pulses, for example, approximately several picoseconds. Optical detectors 1216 and 1265 are attached to polychromators 1215 and 1264, respectively, to detect signal light having undergone wavelength dispersion in the polychromators.

Figure 13A:
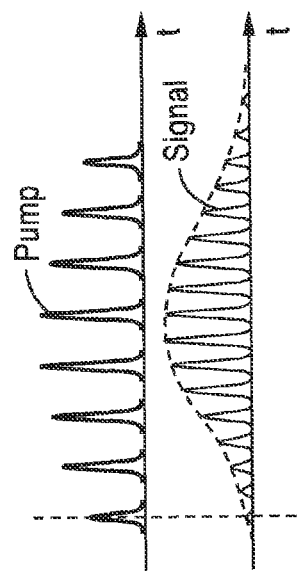
FIG. 13A through FIG. 13E are graphs of signal waveforms illustrating measuring a Raman spectrum of a sample in a spectroscopic diagnosis apparatus according to the elements of the present invention shown in FIG. 12A and FIG. 12B.
Figure 13B:
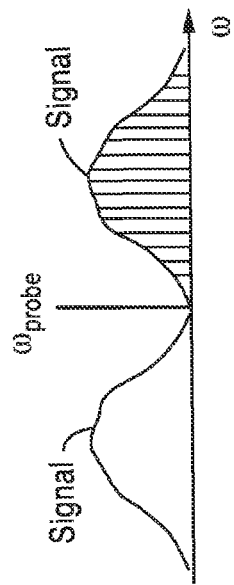
Figure 13C:
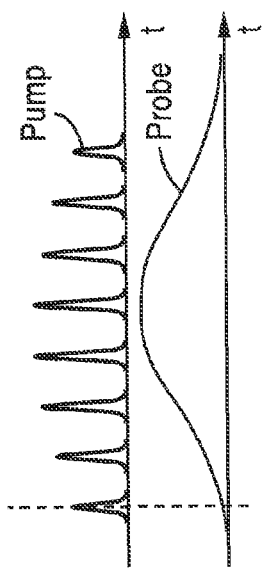
Figure 13D:
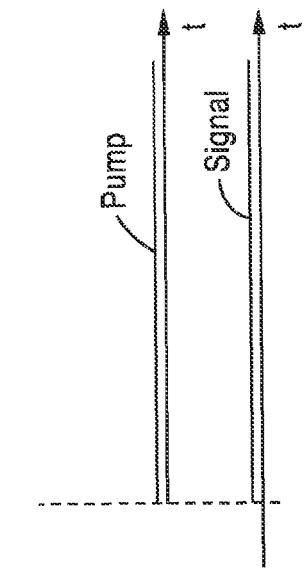
Figure 13E:
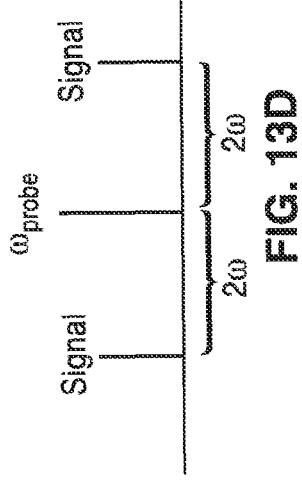

FIG. 13A through FIG. 13E describe elements of the principles upon which optical device 1242 measures a Raman spectrum of a sample in relation to FIG. 12A. FIG. 13A shows the relationship between the time profile of the multiple optical pulses (excitation pulse light) and that of the probe light. To adjust the timing at which the sample is irradiated with each pulse light, probe light timing control means 1232 may be used to adjust the amount of change in the optical length of the optical path 1221 that is produced in variable delay optics 1203. The transmission axis of a polarizer 1207 disposed in the optical path 1221 is set to be perpendicular to the transmission axis of a polarizer 1213 disposed in an optical path 1223. Therefore, when the sample is not irradiated with the excitation pulse light, the probe light does not pass through the polarizer 1213. In this case, the time profile of the excitation pulse light with which the sample is irradiated and the time profile of the probe light that passes through the polarizer 1213 have a value of zero, as shown in FIG. 13B. On the other hand, when the sample is irradiated with the excitation light, vibrational coherence is induced in the sample in an impulsive stimulated Raman scattering process, and transient refractive index anisotropy induced in the sample rotates the polarized probe light, which then passes through the polarizer 1213. Since the polarized probe light is rotated in accordance with the temporal time profile of the vibrational coherence signal and the frequency thereof coincides with the repetition rate of the multiple optical pulses, the probe light passing through the polarizer 1213 has a frequency twice as high as the repetition rate of the multiple pulse train. Therefore, the observed signal light corresponds to the original probe light that undergoes intensity modulation at a frequency twice as high as the repetition rate of the multiple pulse train, as shown in FIG. 13C. Since the probe light is the carrier wave of the vibrational coherence signal, the probe light band having a frequency ωprobe in the frequency spectrum shown in FIG. 13D is accompanied with side bands each having a frequency shifted from the frequency ωprobe by the frequency twice as high as the vibrational frequency ω of a molecule. The spectrum shown in FIG. 13D is the one acquired when the repetition rate of the excitation light is fixed at a specific value, and the Raman spectrum of the sample shown in FIG. 13E is acquired by incrementing the repetition rate and plotting the spectral intensity.

The method for observing a Raman spectrum described above can be performed under the condition that the intensity of narrow line width probe light undergoes intensity modulation at the beat frequency of coherent vibration. The method is therefore applicable to the configuration of optical device 242 of FIG. 2A and FIG. 2B, which detects the probe light diffracted by the transient grating produced in a sample. The method can also be performed in the configuration of the optical device 842 of FIG. 8, which is different example configurations of the optical device of the present invention.

Since the spectroscopic measurement apparatus according to the present embodiment observes the frequency spectrum of the probe light that undergoes intensity modulation at the frequency of vibrational coherence of a molecule in a biological sample, it is not necessary to sweep the timing at which the sample is irradiated with the probe light with respect to the excitation pulse light. In addition to this, the frequency spectrum of the vibrational coherence signal can be determined without having to perform Fourier transform on the signal. Therefore, the time required to acquire a Raman spectrum of the sample can be advantageously reduced. Further, since the amount of change in the optical length does not need to be adjusted precisely in the variable delay optics 1203 or 1253, whereby the optical device is advantageously simplified.

Another element of the spectroscopic measurement apparatus according to the present embodiment that measures a Raman spectrum of a biological sample and analyzes the sample based on the Raman spectrum includes another type of excitation means. That is, when the analysis shows that a specific molecule is present in the sample, the excitation means excites a specific vibrational band having a frequency in the sub-terahertz band or the terahertz band in the specific molecule so that impulsive stimulated Raman scattering occurs.

Figure 14:
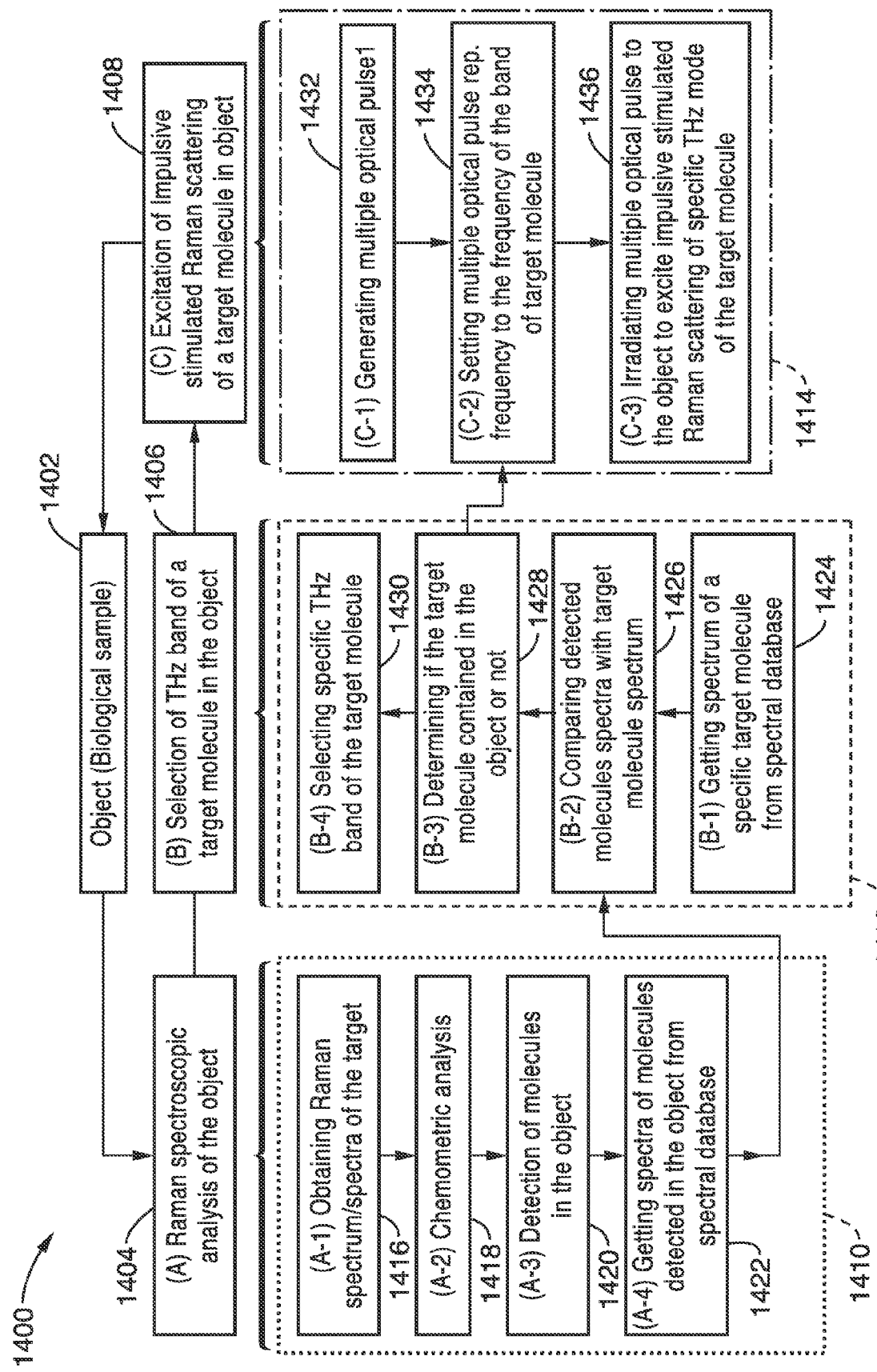
FIG. 14 is a flowchart of performing a spectroscopic measurement according to an embodiment of the present invention.

FIG. 14 illustrates an example embodiment 1400 of the operation of a spectroscopic measurement apparatus according to the present invention which excites a specific vibrational band in a specific molecule in a sample 1402 so that impulsive stimulated Raman scattering occurs. The three principles steps (A) 1404, (B) 1406, and (C) 1408 are shown being carried out, and which are more specifically described later.

A. Perform Raman spectroscopic analysis on a sample.

B. Judge whether a target molecule is present in the sample and select a terahertz vibrational band of the target molecule.

C. Irradiate the specimen with multiple optical pulses to excite the target molecule so that impulsive stimulated Raman scattering occurs.

Figure 15A:
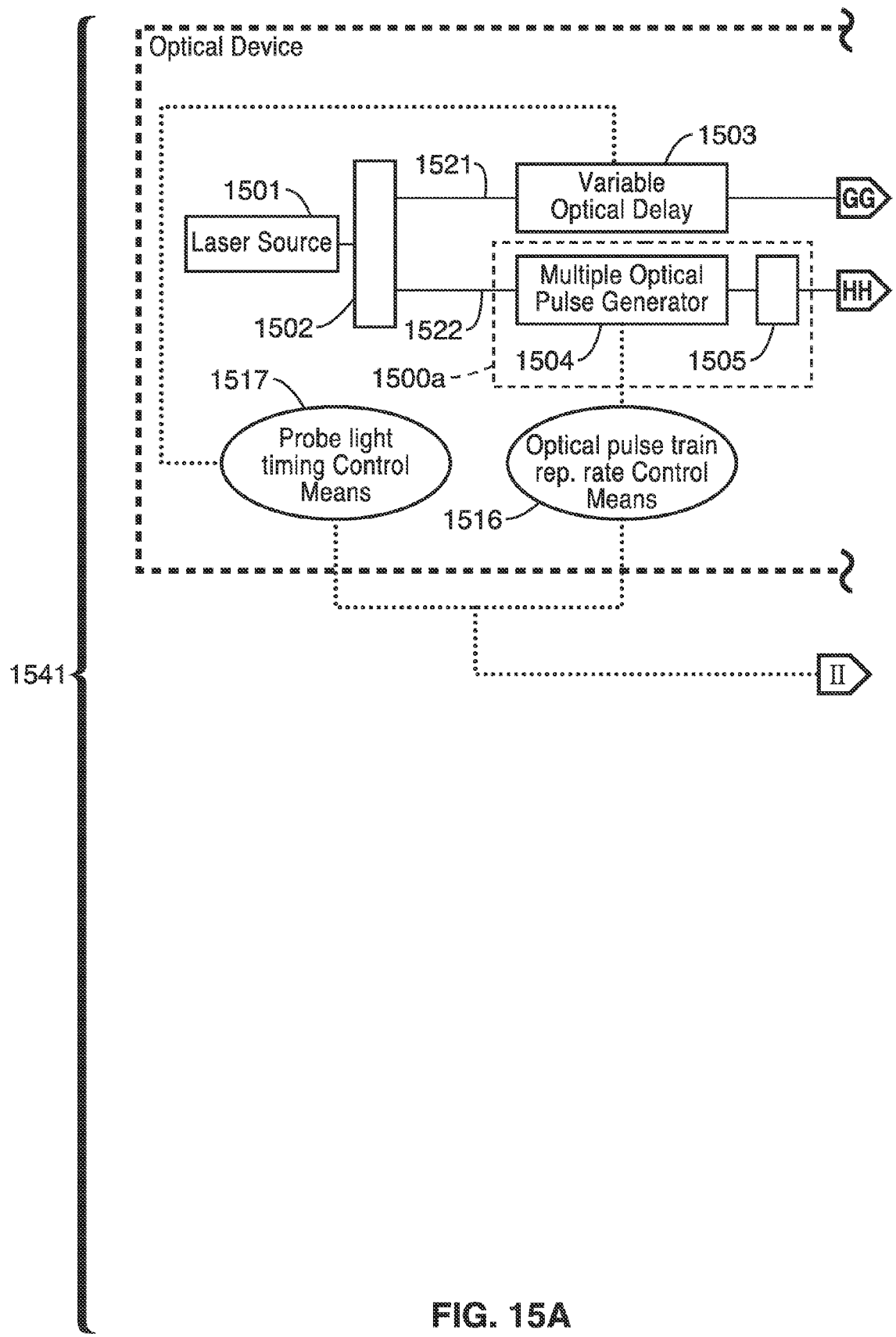
FIG. 15A and FIG. 15B is a schematic of a spectroscopic measurement apparatus according to an embodiment of the present invention, which measures Raman sample spectrum of a sample in response to exciting a terahertz vibrational mode of a specific molecule.
Figure 15B:
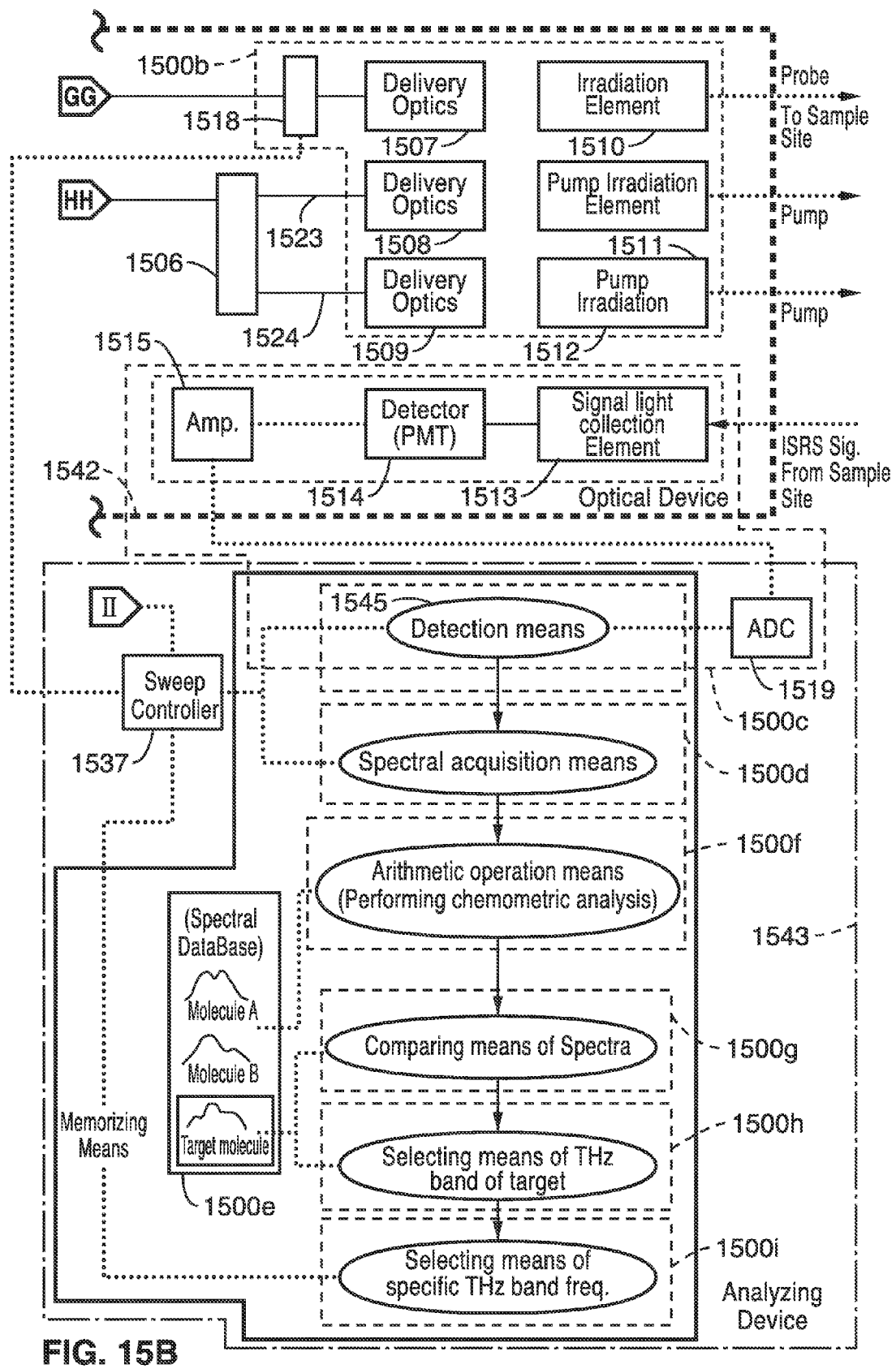

FIG. 15A and FIG. 15B illustrate a schematic example of a configuration of the apparatus that carries out the processes in the flowchart. Each of the method substeps of the spectroscopic measurement apparatus shown in FIG. 14 are described as being carried out in the schematic block diagram of the FIG. 15A and FIG. 15B.

A spectroscopic measurement apparatus 1541 according to the present embodiment includes an optical device 1542 and an analyzing device 1543. While the configuration of optical device 1542 in FIG. 15A and FIG. 15B is the same as that of the optical device 242 of FIG. 2A and FIG. 2B, any of the configurations described above as the variations of the configuration of the optical device may be employed. A single laser source 1501 is depicted coupled to a splitter 1502 from which are optical paths 1521 and 1522 derived. Along first path 1521 is a shutter 1518 and a variable optical delay 1503 prior to reaching irradiation means 1500b and delivery optics 1507 and irradiation element 1510. Along second path 1522 is a pulse train generator 1500a comprising a multiple optical pulse generator 1504 controlled by rate control means 1516 and dispersion compensator (DC) 1505 shown for generating the optical pulse train (multiple optical pulses), the latter of which is disposed as required. Output from pulse train generator is split by a splitter 1506 into paths 1523 and 1524. First path 1523 is coupled to delivery optics 1508 and irradiation element 1511 of block 200b, while the second path 1524 is coupled to delivery optics 1509 and irradiation element 1512 of block 1500b.

It should be appreciated that the configuration of the apparatus in the present embodiment includes a shutter 1518 disposed in an optical path 1521, whereby the optical path 1521 can be blocked as required and the sample can be irradiated only with the multiple optical pulses. The analyzing device 1543 includes detection means 1500c, spectrum acquisition means 1500d, memorizing means 1500e, arithmetic operation means 1500F, spectrum comparing means 1500G, frequency selecting means 1500H, frequency setting means 1500I, and a sweep controller 1537. The detection means 1500c is formed of a program running on a computer 1530, a signal light collection element 1513, an optical detector 1514, an amplifier 1515, and an A/D converter 1519 whose output is directed to detector 1545 within detection means 1500c. The spectrum acquisition means 1500d is a program running on the computer 1530. The detection means and the spectrum acquisition means are the same as the detection means 200c and the spectrum acquisition means 200d described above. The sweep controller 1537 can be the same as the sweep controller 237 described in FIG. 2A and FIG. 2B. As in the method for acquiring a spectrum of a sample performed by using the detection means 200c and the spectrum acquisition means 200d described previously with regard to FIG. 1, FIG. 2A and FIG. 2B, the detection means 1500c and the spectrum acquisition means 1500d determine the frequency spectrum of the vibrational coherence signal acquired at each repetition rate of the multiple optical pulses. A Raman spectrum of the biological sample is then acquired from the frequency spectra for the repetition frequencies. The arithmetic operation means 1500F has the operation function performed by the arithmetic operation means 600f described in regard to FIG. 5 and FIG. 6, and can perform chemometric analysis on the acquired Raman spectrum of the biological sample.

The Raman spectrum analyzing means in the arithmetic operation means 1500F involves performing chemometric analysis to judge whether or not a specific biological molecule is present in the sample. A specific example of the method will be described below. The memorizing means 1500e memorizes a spectral database that stores Raman spectra of a large number of different biological molecules that are expected to form the sample under measurement. The memorizing means may be a memory built in the computer 1530 or an external memorizing device. Each of the Raman spectra of the biological molecules reflects at least two types of vibrational mode information, the vibrational frequency information and the vibrational phase relaxation information. Each of the Raman spectra may also reflect the information on the tensor components of the third-order nonlinear susceptibility for each vibrational mode as well as the two types of vibrational mode information described above. The spectral database is used to build a spectroscopic model (calibration model), and then spectral calibration based on Principle Component Regression (PCR) or Partial Least Square Fitting (PLS) is performed to determine the concentration of a molecule in the sample.

The Raman spectra of the molecules whose concentrations have been predicted by the spectral calibration are used to establish a Raman spectrum of the sample. When an uncalibrated molecule is present, one that is not included in the spectroscopic model, such as a molecule that is not considered as a spectrum calibration candidate, the difference spectrum between the acquired Raman spectrum of the sample and the established Raman spectrum of the sample is determined. The difference spectrum is the Raman spectrum of the molecule or the group of molecules that are not included in the spectroscopic model. A molecule present in the sample may alternatively be detected by successively comparing the Raman spectrum corresponding to the difference spectrum with the Raman spectra of the biological molecules memorized in the memorizing means 1500e.

According to another spectrum analysis method using the arithmetic operation means 1500F, the spectroscopic measurement apparatus of the present embodiment is used to measure a plurality of Raman spectra of a biological sample, and then self modeling curve resolution calculation is performed on the plurality of spectra to determine the constituent spectra that form the Raman spectra. In this case, a molecule present in the sample may alternatively be detected by comparing the constituent spectra with the spectral data of the biological molecules memorized in the memorizing means 1500e.

In a spectrum of a sample observed by the spectroscopic measurement apparatus of the present embodiment, when an isolated vibrational band with a small amount of overlap with other vibrational bands in the spectrum is present, the corresponding molecule may be identified not by performing chemometric analysis but only by comparing the spectrum of the sample with the waveform patterns of the spectra stored in the spectral database.

In FIG. 14 the steps subsumed under step 1404 (A) of the spectroscopic measurement apparatus according to the invention is used to measure in step 1416 (A-1) a Raman spectrum of a sample that reflects at least two types of vibrational mode information, the vibrational frequency and the vibrational phase relaxation time of a molecule. Then according to step 1418 (A-2) chemometric analysis is performed based on the acquired Raman spectrum of the sample. In step 1420 (A-3) the Raman spectrum of a molecule is detected in the sample based on the chemometric analysis and is compared in step 1422 (A-4) with the Raman spectrum of a desired target molecule selected in advance to judge whether or not the target molecule is present in the sample. When the desired target molecule is present in the sample, a specific vibrational band having a frequency in the sub-terahertz band or the terahertz band in the target molecule is selected. Examples of the desired target molecule include an enzyme that catalyzes a biochemical reaction that is not preferable to an organism and a transcription factor protein. The sample is irradiated with the multiple optical pulses after the repetition rate of the optical pulse train is synchronized with the vibrational band frequency of the selected target molecule.

After the Raman spectrum analyzing means described above is used to detect a plurality of different molecules in the sample, the steps 1424 (B-1), 1426 (B-2), 1428 (B-3), and 1430 (B-4) are performed which are shown in the boxed area subsumed under block 1406 (B) of FIG. 14. In step 1424 (B-1) a Raman spectrum is acquired of a target molecule from the spectral database, and a comparison is performed in step 1426 (B-2) for the Raman spectra of the detected molecules in the sample with the Raman spectrum of the target molecules. In step 1428 (B-3) it is determined whether or not the target molecule is present in the sample. Then in step 1430 (B-4) a specific Raman band is selected in the sub-terahertz or the terahertz band of the target molecule.

Carrying out the steps described above allows the selection of a vibrational mode of the target molecule in the sample that will be irradiated with multiple optical pulses so that impulsive stimulated Raman scattering is excited.

A method for carrying out the above steps will be specifically described below in relation to FIG. 15A and FIG. 15B. The database containing Raman spectra of biological molecules and memorized in the memorizing means 1500e should include a sub-terahertz band or terahertz band Raman spectrum of a desired molecule, which is a target molecule. The spectrum comparing means 1500G reads the Raman spectrum of the desired target molecule from the memorizing means 1500e. Similarly, the spectrum comparing means also reads the Raman spectra of a plurality of different molecules detected in the sample as a result of the chemometric analysis from the memorizing means 1500e. The spectrum comparing means 1500G is, for example, a program running on the computer 1530, compares the Raman spectra of a plurality of different molecules detected in the sample with the Raman spectrum of the target molecule, and determines the degree of similarity between the two spectra. In the comparing means, the difference in the spectral intensity between the two Raman spectra is squared for each vibrational frequency, and the squares of the intensity difference for the vibrational frequencies are summed. In this case, the similarity between the two Raman spectra is judged based on whether the sum is greater or smaller than a predetermined value. Alternatively, the difference in the peak frequency between the two Raman spectra for each Raman band may be calculated, and the spectra may be compared with each other in the same method described above. Still alternatively, the spectrum comparing means may display the two Raman spectra on a screen and let an operator visually compare the spectra. When the spectrum comparing means judges that the similarity between the Raman spectrum of any of the molecules detected in the sample and the Raman spectrum of the target molecule is high, it then judges that the target molecule is present in the sample.

The frequency selecting means 1500H is, for example, a program running on the computer 1530, and numerically detects the peak frequency of the Raman band that appears in the Raman spectrum of the target molecule having been judged to be present in the sample by the comparing means 1500G. Alternatively, the frequency selecting means may display the result of the comparing means 1500G's operation of comparing the Raman spectra on a screen and let the operator visually read the peak frequency of the Raman band. In this way, after the spectrum comparing means judges that the target molecule is present in the sample being measured, the frequency selecting means reads the peak frequency of the desired Raman band having a vibrational frequency in the sub-terahertz band or the terahertz band from the Raman spectrum of the target molecule.

After a specific Raman band frequency in the target molecule is acquired in the method described above, the steps 1432 (C-1), 1434 (C-2), and 1436 (C-3), shown surrounded by a dot-dashed line, subsumed under step 1408 (C) of FIG. 14 are then carried out. Optical pulse train repetition rate control means 1516 can be the same as the optical pulse train repetition rate control means 216 described previously in relation to FIG. 2A and FIG. 2B. The optical pulse train repetition rate control means 1516 can operate in combination with a control program loaded into computer 1530 that instructs sweep controller 1537 to set the repetition rate of the optical pulse train produced in multiple optical pulse generator 1504 at a desired value. The frequency setting means 1500I transfers the Raman band frequency of the target molecule read by the frequency selecting means 1500H as the repetition rate of the optical pulse train to be set to the control program. The means 1500I is a program running on computer 1530 or an interface that allows the operator to input the Raman band frequency of the target molecule to the control program. In this way, the repetition rate of the multiple optical pulses is synchronized with the Raman band frequency. At the same time, the shutter 1518 in the optical path 1521 is closed so that only the multiple optical pulses (but not the probe light) travel along the optical path 1523 and/or the optical path 1524 and the sample is irradiated with the multiple optical pulses via an irradiation element(s).

The biological sample is irradiated with the multiple optical pulses, and impulsive stimulated Raman scattering is excited in the molecules in the sample. In this process, only the vibrational mode of the target molecule that is equal to the preset repetition rate of the multiple optical pulses is excited more efficiently than other vibrational modes. When the target molecule is a biological molecule having a large molecular weight, such as a protein and a nucleic acid, the collective mode of the biological molecule can be excited as long as a terahertz vibrational band having an appropriate frequency is selected in the step B4 described above, that is, the step of determining the vibrational band of the target molecule.

An exemplary desirable form of the excitation of a molecule in a biological sample in the collective mode by using multiple optical pulse irradiation described above involves irradiating the biological sample with multiple optical pulses having a wavelength longer than that of near ultraviolet light to excite an impulsive stimulated Raman scattering process of a target molecule present in the sample via the S1 excited state (first electronic excited state) of the target molecule. In this case, since the Frank Condon factor is not zero as described above, a higher-order collective mode included in the band width of the multiple optical pulses is excited, whereby a large amplitude motion of the biological molecule is advantageously induced. The ISRS excitation described above is applicable when the target molecule is an enzyme protein containing heme, flavin adenine dinucleotide (FAD), NADH (nicotinamide adenine dinucleotide acid), or other cofactors.

In the spectroscopic measurement apparatus according to the present embodiment, ISRS can be used to excite only molecular vibration at a specific terahertz vibrational frequency in a biological sample. When the terahertz vibrational mode is the collective mode of a protein, and a higher-order vibrational mode is excited, change in a higher-order structure of the protein is possibly induced. Therefore, irradiating an organism with multiple optical pulses can inhibit the activity of an enzyme protein that catalyzes a biochemical reaction that is not desirable to the organism.

In the ISRS in which excitation is achieved by a single femtosecond optical pulse, vibrational modes excited in an enzyme protein to be inhibited disadvantageously include a vibrational mode which does not relate to any function and a vibrational mode of a molecule other than the enzyme molecule. Therefore, absence of mode selectivity in the vibrational excitation process not only causes inefficiency in terms of energy but also leads to excitation of the vibrational mode of a biological molecule that is not necessary to be disturbed. In this case, the biological sample may be adversely affected. Exciting a biological sample with a multiple optical pulse train provides advantageous effects of preventing damage of the biological sample resulting from the light irradiation and exciting vibrational modes of only a specific molecule or an extremely small number of different types of molecules.

From the foregoing description it will be appreciated that the present invention can be embodied in various ways, including but not limited to:

1. A spectroscopic measurement apparatus for measuring a Raman spectrum of an object volume containing a plurality of different molecules, comprising: pump optical pulse train generation means configured for generating a pump optical pulse train having an arbitrary repetition rate; irradiation means for irradiating a single location in an object volume to be measured with said pump optical pulse train and with a probe light to excite impulsive stimulated Raman scattering; detection means for detecting vibrational coherence information of the object volume in response to the probe light and excitation of impulsive stimulated Raman scattering by said pump optical pulse train; and spectrum acquisition means for acquiring a Raman spectrum of the object volume including at least vibrational frequency information and vibrational phase relaxation time information, in response to collecting vibrational coherence information from the object detected by said detection means for each of a plurality of different repetition frequencies of the pump optical pulse train.

2. The spectroscopic measurement apparatus as recited in embodiment 1, further comprising: memorizing means for memorizing Raman spectra of a plurality of different molecules, the Raman spectra reflecting at least two types of vibrational information including vibrational frequency information and vibrational phase relaxation time information; and operating means for performing chemometric analysis on the Raman spectrum of the object by using the Raman spectra memorized in the memorizing means.

3. The spectroscopic measurement apparatus as recited in embodiment 2, wherein said operating means further comprises a spectrum comparing means configured for comparing the Raman spectrum of a molecule detected in the object volume with a desired target molecule for which at least two types of information including vibrational frequency information and vibrational phase relaxation time information are known.

4. The spectroscopic measurement apparatus as recited in embodiment 3, further comprising: frequency selecting means configured for selecting a band frequency of a desired Raman band from the Raman spectrum of the target molecule based on the comparison result obtained by the spectrum comparing means; and frequency setting means for setting the repetition rate of the pump optical pulse train based on the comparison result; wherein a specific molecule vibration in the target molecule in the object is selectively excited.

5. The spectroscopic measurement apparatus as recited in embodiment 4, wherein the irradiation means irradiates the volume to be measured with the pump optical pulse train set by the frequency setting means but not with the probe light.

6. The spectroscopic measurement apparatus as recited in embodiment 1, wherein the pump optical pulse train is formed of femtosecond optical pulses and has an arbitrary repetition rate ranging from the sub-terahertz band to the terahertz band.

7. The spectroscopic measurement apparatus as recited in embodiment 1, wherein said spectrum acquisition means is configured for sweeping the repetition rate of the pump optical pulse train.

8. The spectroscopic measurement apparatus as recited in embodiment 1, further comprising: a laser source; a splitter coupled to said laser source for creating a first optical beam and a second optical beam; a variable optical delay configured for receiving said first optical beam and outputting a probe light; and a multiple optical pulse generator configured for receiving said second optical beam through multiple translation stages and outputting at least one said pump optical pulse train having an arbitrary repetition rate.

9. The spectroscopic measurement apparatus as recited in embodiment 8, wherein said laser source comprises a single femtosecond laser source that outputs Transform Limit (TL) pulses which each have a temporal width shorter than 100 femtoseconds.

10. The spectroscopic measurement apparatus as recited in embodiment 1, wherein said irradiation means comprises delivery optics for directing said probe light and said pump optical pulse train to an object volume containing a plurality of different molecules.

11. The spectroscopic measurement apparatus as recited in embodiment 1, wherein said detection means comprises: a light collection element configured for receiving light interacting with said object volume; and an optical detector configured for registering light collected by said light collection element.

12. The spectroscopic measurement apparatus as recited in embodiment 1, wherein said spectrum acquisition means comprises: a computer processor with associated memory, electrically coupled to said pump optical pulse train generation means, irradiation means, detection means; programming executable on said computer processor and memory for, performing sweeping of repetition rate of said pump optical pulse train generation means, controlling delay within said probe light, and determining a Raman spectrum of the object volume including at least vibrational frequency information and vibrational phase relaxation time information, in response to vibrational coherence information determined in response to registration of light by said detection means for each of a plurality of different repetition frequencies of the pump optical pulse train.

13. A spectroscopic measurement apparatus for measuring a Raman spectrum of an object volume containing a plurality of molecules, comprising: a laser source; a splitter coupled to said laser source for creating a first optical beam and a second optical beam; a variable optical delay configured for receiving said first optical beam and outputting an optical probe signal to excite impulsive stimulated Raman scattering; a multiple optical pulse generator configured for receiving said second optical beam through multiple translation stages and outputting at least one pump optical pulse train having an arbitrary repetition rate; delivery optics for directing said optical probe signal and at least one pump optical pulse train to an object volume containing a plurality of different molecules; a light collection element configured for receiving light interacting with said object volume; an optical detector configured for registering light collected by said light collection element; a computer processor, and associated memory, coupled to said variable optical delay, said multiple optical pulse generator, and said optical detector; and programming executable on said computer processor and memory for, performing sweeping of repetition rate of said pump optical pulse train and translating stages within said multiple optical pulse generator, controlling delay within said variable optical delay, determining a Raman spectrum of the object volume including at least vibrational frequency information and vibrational phase relaxation time information, in response to vibrational coherence information determined in response to registration of light by said optical detector for each of a plurality of different repetition frequencies of the pump optical pulse train.

14. The spectroscopic measurement apparatus as recited in embodiment 13, wherein said programming further comprises: storing Raman spectra of a plurality of different molecules, the Raman spectra reflecting at least two types of vibrational information including vibrational frequency information and vibrational phase relaxation time information; and performing chemometric analysis on the Raman spectrum of the object by using the stored Raman spectra.

15. The spectroscopic measurement apparatus as recited in embodiment 14, wherein said programming further comprises comparing the Raman spectrum of a molecule detected in the object volume with a desired target molecule for which at least two types of information including vibrational frequency information and vibrational phase relaxation time information are known.

16. The spectroscopic measurement apparatus as recited in embodiment 15, wherein said programming further comprises: selecting a band frequencies of a desired Raman band from the Raman spectrum of a target molecule based on the comparison result obtained when comparing the Raman spectrum; and setting of the repetition rate of the pump optical pulse train based on the result of comparing the Raman spectrum; wherein a specific molecule vibration in the target molecule in the object volume is selectively excited.

17. The spectroscopic measurement apparatus as recited in embodiment 13, wherein the pump optical pulse train comprises femtosecond optical pulses with an arbitrary repetition rate ranging from the sub-terahertz band to the terahertz band.

18. A method of performing spectroscopic measurements in response to light-molecule interaction on the molecules within an object, comprising the steps of: generating pump optical pulse trains from a laser source; generating a probe pulse; guiding the pump optical pulse trains and probe pulse to an object having molecular species being measured; obtaining vibrational coherence spectrum at arbitrary repetition frequency of the optical pulse trains; scanning repetition rate of the pump optical pulse trains; performing iterations of the above steps; and obtaining Raman spectrum of the target from vibrational coherence spectra.

19. A method as recited in embodiment 18, wherein said probe pulse and said pump optical pulse trains are generated from a single laser source.

20. A method as recited in embodiment 18, further comprising: storing Raman spectra of a plurality of different molecules, the Raman spectra reflecting at least two types of vibrational information including vibrational frequency information and vibrational phase relaxation time information; and performing chemometric analysis on the Raman spectrum of the object by using the stored Raman spectra.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A spectroscopic measurement apparatus for measuring a Raman spectrum of an object volume containing a plurality of different molecules, comprising:
    pump optical pulse train generation means configured for generating a pump optical pulse train having an arbitrary repetition rate;
    irradiation means for irradiating a single location in an object volume to be measured with said pump optical pulse train and with a probe light to excite impulsive stimulated Raman scattering;
    detection means for detecting vibrational coherence information of the object volume in response to the probe light and excitation of impulsive stimulated Raman scattering by said pump optical pulse train; and
    spectrum acquisition means for acquiring a Raman spectrum of the object volume including at least vibrational frequency information and vibrational phase relaxation time information, in response to collecting vibrational coherence information from the object detected by said detection means for each of a plurality of different repetition frequencies of the pump optical pulse train.

2. The spectroscopic measurement apparatus as recited in claim 1, further comprising:
    memorizing means for memorizing Raman spectra of a plurality of different molecules, the Raman spectra reflecting at least two types of vibrational information including vibrational frequency information and vibrational phase relaxation time information; and
    operating means for performing chemometric analysis on the Raman spectrum of the object by using the Raman spectra memorized in the memorizing means.

3. The spectroscopic measurement apparatus as recited in claim 2, wherein said operating means further comprises a spectrum comparing means configured for comparing the Raman spectrum of a molecule detected in the object volume with a desired target molecule for which at least two types of information including vibrational frequency information and vibrational phase relaxation time information are known.

4. The spectroscopic measurement apparatus as recited in claim 3, further comprising:
    frequency selecting means configured for selecting a band frequency of a desired Raman band from the Raman spectrum of the target molecule based on the comparison result obtained by the spectrum comparing means; and
    frequency setting means for setting the repetition rate of the pump optical pulse train based on the comparison result;
    wherein a specific molecule vibration in the target molecule in the object is selectively excited.

5. The spectroscopic measurement apparatus as recited in claim 4, wherein the irradiation means irradiates the volume to be measured with the pump optical pulse train set by the frequency setting means but not with the probe light.

6. The spectroscopic measurement apparatus as recited in claim 1, wherein the pump optical pulse train is formed of femtosecond optical pulses and has an arbitrary repetition rate ranging from the sub-terahertz band to the terahertz band.

7. The spectroscopic measurement apparatus as recited in claim 1, wherein said spectrum acquisition means is configured for sweeping the repetition rate of the pump optical pulse train.

8. The spectroscopic measurement apparatus as recited in claim 1, further comprising:
    a laser source;

a splitter coupled to said laser source for creating a first optical beam and a second optical beam;

a variable optical delay configured for receiving said first optical beam and outputting a probe light; and a multiple optical pulse generator configured for receiving said second optical beam through multiple translation stages and outputting at least one said pump optical pulse train having an arbitrary repetition rate.

9. The spectroscopic measurement apparatus as recited in claim 8, wherein said laser source comprises a single femtosecond laser source that outputs Transform Limit (TL) pulses which each have a temporal width shorter than 100 femtoseconds.

10. The spectroscopic measurement apparatus as recited in claim 1, wherein said irradiation means comprises delivery optics for directing said probe light and said pump optical pulse train to an object volume containing a plurality of different molecules.

11. The spectroscopic measurement apparatus as recited in claim 1, wherein said detection means comprises:

a light collection element configured for receiving light interacting with said object volume; and an optical detector configured for registering light collected by said light collection element.

12. The spectroscopic measurement apparatus as recited in claim 1, wherein said spectrum acquisition means comprises:

a computer processor with associated memory, electrically coupled to said pump optical pulse train generation means, irradiation means, detection means;

programming executable on said computer processor and memory for, performing sweeping of repetition rate of said pump optical pulse train generation means, controlling delay within said probe light, and determining a Raman spectrum of the object volume including at least vibrational frequency information and vibrational phase relaxation time information, in response to vibrational coherence information determined in response to registration of light by said detection means for each of a plurality of different repetition frequencies of the pump optical pulse train.

13. A spectroscopic measurement apparatus for measuring a Raman spectrum of an object volume containing a plurality of molecules, comprising:

a laser source;

a splitter coupled to said laser source for creating a first optical beam and a second optical beam;

a variable optical delay configured for receiving said first optical beam and outputting an optical probe signal to excite impulsive stimulated Raman scattering;

a multiple optical pulse generator configured for receiving said second optical beam through multiple translation stages and outputting at least one pump optical pulse train having an arbitrary repetition rate;

delivery optics for directing said optical probe signal and at least one pump optical pulse train to an object volume containing a plurality of different molecules;

a light collection element configured for receiving light interacting with said object volume;

an optical detector configured for registering light collected by said light collection element;

a computer processor, and associated memory, coupled to said variable optical delay, said multiple optical pulse generator, and said optical detector; and programming executable on said computer processor and memory for, performing sweeping of repetition rate of said pump optical pulse train and translating stages within said multiple optical pulse generator, controlling delay within said variable optical delay, determining a Raman spectrum of the object volume including at least vibrational frequency information and vibrational phase relaxation time information, in response to vibrational coherence information determined in response to registration of light by said optical detector for each of a plurality of different repetition frequencies of the pump optical pulse train.

14. The spectroscopic measurement apparatus as recited in claim 13, wherein said programming further comprises:

storing Raman spectra of a plurality of different molecules, the Raman spectra reflecting at least two types of vibrational information including vibrational frequency information and vibrational phase relaxation time information; and performing chemometric analysis on the Raman spectrum of the object by using the stored Raman spectra.

15. The spectroscopic measurement apparatus as recited in claim 14, wherein said programming further comprises comparing the Raman spectrum of a molecule detected in the object volume with a desired target molecule for which at least two types of information including vibrational frequency information and vibrational phase relaxation time information are known.

16. The spectroscopic measurement apparatus as recited in claim 15, wherein said programming further comprises:

selecting a band frequencies of a desired Raman band from the Raman spectrum of a target molecule based on the comparison result obtained when comparing the Raman spectrum; and setting of the repetition rate of the pump optical pulse train based on the result of comparing the Raman spectrum;

wherein a specific molecule vibration in the target molecule in the object volume is selectively excited.

17. The spectroscopic measurement apparatus as recited in claim 13, wherein the pump optical pulse train comprises femtosecond optical pulses with an arbitrary repetition rate ranging from the sub-terahertz band to the terahertz band.

18. A method of performing spectroscopic measurements in response to light-molecule interaction on the molecules within an object, comprising the steps of:

generating pump optical pulse trains from a laser source;

generating a probe pulse;

guiding the pump optical pulse trains and probe pulse to an object having molecular species being measured;

obtaining vibrational coherence spectrum at arbitrary repetition frequency of the optical pulse trains;

scanning repetition rate of the pump optical pulse trains;

performing iterations of the above steps; and obtaining Raman spectrum of the target from vibrational coherence spectra.

19. A method as recited in claim 18, wherein said probe pulse and said pump optical pulse trains are generated from a single laser source.

20. A method as recited in claim 18, further comprising:

storing Raman spectra of a plurality of different molecules, the Raman spectra reflecting at least two types of vibrational information including vibrational frequency information and vibrational phase relaxation time information; and performing chemometric analysis on the Raman spectrum of the object by using the stored Raman spectra.

* * * * *